US005703256A

United States Patent [19]
Cusumano et al.

[11] Patent Number: 5,703,256
[45] Date of Patent: Dec. 30, 1997

[54] FUNCTIONALIZATION OF POLYMERS BASED ON KOCH CHEMISTRY AND DERIVATIVES THEREOF

[75] Inventors: Joseph Victor Cusumano, Watchung; William Daniel Diana, Belle Mead, both of N.J.; Jacob Emert, Brooklyn, N.Y.; Keith Raymond Gorda, Little York, N.J.; Richard H. Schlosberg, Baton Rouge, La.; David A. Young, Seattle, Wash.; Albert I. Yezrielev, Houston, Tex.; William Bernard Eckstrom, Fanwood, N.J.; Edris Eileen Manry, Prairieville; Michael John Keenan, Baton Rouge, both of La.

[73] Assignee: Exxon Chemical Patents Inc., Linden, N.J.

[21] Appl. No.: 764,918

[22] Filed: Dec. 16, 1996

Related U.S. Application Data

[60] Continuation of Ser. No. 520,323, Aug. 28, 1995, abandoned, which is a division of Ser. No. 992,403, Dec. 17, 1992, abandoned.

[51] Int. Cl.$^6$ .................................................. C07C 63/00
[52] U.S. Cl. ................ 554/224; 252/51.5 A; 252/51.5 R
[58] Field of Search ........................ 554/224; 252/51.5 A, 252/51.5 R

[56] References Cited

U.S. PATENT DOCUMENTS

| | | | |
|---|---|---|---|
| Re. 26,433 | 8/1968 | Le Suer | 252/33.6 |
| 2,586,070 | 2/1952 | Luten, Jr. et al. | 260/624 |
| 2,831,877 | 4/1958 | Koch | 260/413 |
| 2,967,873 | 1/1961 | Koch et al. | 260/410.9 |
| 3,036,003 | 5/1962 | Verdol | 252/33.4 |
| 3,059,007 | 10/1962 | Vos et al. | 260/413 |
| 3,087,936 | 4/1963 | Le Suer | 260/326.3 |
| 3,167,585 | 1/1965 | Anderson et al. | 260/533 |
| 3,184,411 | 5/1965 | Lowe | 252/46.7 |
| 3,185,645 | 5/1965 | Clayton | 252/46.7 |
| 3,185,704 | 5/1965 | Kahn et al. | 260/326.3 |
| 3,200,107 | 8/1965 | Le Suer | 260/132 |
| 3,245,908 | 4/1966 | Lowe | 252/51.5 |
| 3,245,909 | 4/1966 | Lowe | 252/51.5 |
| 3,245,910 | 4/1966 | Lowe | 252/51.5 |
| 3,254,025 | 5/1966 | Le Suer | 252/32.7 |
| 3,256,185 | 6/1966 | Le Suer | 252/32.7 |
| 3,278,550 | 10/1966 | Norman et al. | 260/326.3 |
| 3,280,034 | 10/1966 | Anzenberger et al. | 252/51.5 |
| 3,281,428 | 10/1966 | Le Suer | 260/326.3 |
| 3,282,955 | 11/1966 | Le Suer | 260/326.3 |
| 3,284,410 | 11/1966 | Meinhardt | 252/49.6 |
| 3,306,908 | 2/1967 | Le Suer | 260/326.3 |
| 3,312,619 | 4/1967 | Vineyard | 252/47.5 |
| 3,331,776 | 7/1967 | Krukziener | 252/56 |
| 3,338,832 | 8/1967 | Le Suer | 252/47.5 |
| 3,344,069 | 9/1967 | Stuebe | 252/49.6 |
| 3,349,107 | 10/1967 | Pawlenko | 260/410.9 |
| 3,361,673 | 1/1968 | Stuart et al. | 252/51.5 |
| 3,366,569 | 1/1968 | Norman et al. | 252/51.5 |
| 3,367,943 | 2/1968 | Miller et al. | 260/326.3 |
| 3,369,021 | 2/1968 | Le Suer | 260/268 |
| 3,373,111 | 3/1968 | Le Suer et al. | 252/51.5 |
| 3,381,022 | 4/1968 | Le Suer | 260/404.8 |
| 3,390,086 | 6/1968 | O'Halloran | 252/47.5 |
| 3,401,118 | 9/1968 | Benoit, Jr. | 252/51.5 |
| 3,403,102 | 9/1968 | Le Suer | 252/49.8 |
| 3,415,750 | 12/1968 | Anzenberger | 252/51.5 |
| 3,428,561 | 2/1969 | Le Suer | 252/32.5 |
| 3,442,808 | 5/1969 | Traise et al. | 252/49.6 |
| 3,445,441 | 5/1969 | Rushton | 260/89.5 |
| 3,455,832 | 7/1969 | Davis | 252/51.5 |
| 3,458,530 | 7/1969 | Siegel et al. | 260/326.5 |
| 3,470,098 | 9/1969 | O'Halloran | 252/47.5 |

(List continued on next page.)

FOREIGN PATENT DOCUMENTS

| | | |
|---|---|---|
| 0 148 592 A2 | 7/1985 | European Pat. Off. |
| 0 129 368 A1 | 12/1985 | European Pat. Off. |
| 0 462 319 A1 | 12/1991 | European Pat. Off. |
| 62-164645 | 1/1986 | Japan |
| 62-192338 | 2/1986 | Japan |
| 4-15240 | 5/1990 | Japan |
| 51-41320 | 5/1990 | Japan |
| 984409 | 2/1965 | United Kingdom |
| 1085903 | 10/1967 | United Kingdom |
| 1162436 | 8/1969 | United Kingdom |
| 1188900 | 4/1970 | United Kingdom |

OTHER PUBLICATIONS

Billmeyer, J.R., Textbook of Polymer Sciences, 2nd Edition, J. Wiley, pp. 3–21 (1971).

N. Bahrmann, Chapter 5, Koch Reactions. "New Synthesis with Carbon Monoxide", Edited by J. Falbe; Springer-Verlag, New York, New York 1980.

Y. Komatsu et al., Maruzen Sekiyo Gihi 21, 51 (1976).

Ya Eidus et al., "Synthesis of Derivatives of Carboxylic Acids Under Acid Catalysis Conditions from Carbon Monoxide, Olefins, and Compounds being Acylated" Z. Org. Chem. 4 (3) 376 (1968).

Gushein, et al., "Investigation of the Reaction of Ozone with Phenols", Neftekhimiya, vol. 12, (No. 3) 383 (1972).

Wender, I., Organic Synthesis via Metal Carbonyls, vol. 2, pp. 233–296 1971.

Puzitskii et al., *Carbonylation of Olefins and Alcohols with Carbon Monoxide in the Presence of a Catalyst System: $BF_3H_2O$-Liquid $SO_2$*, Izvestiya Akademii Nauk SSSR, Seriya Khimicheskaya, No. 10, pp. 2331–2334, Oct. 1977.

Chemical Abstracts No. CA77 (12):76298p, 1972.

Chemischer informationdienst 41 (1972) A copy of this reference was not submitted in USSN 992,403 or here, because diligent efforts to obtain a copy have been unsuccessful.

*Primary Examiner*—Samuel Barts
*Attorney, Agent, or Firm*—K. R. Walton

[57] ABSTRACT

A Koch functionalized product which is the reaction product of at least one polymer having a number average molecular weight of at least 500 and at least ethylenic double bond per polymer chain, with carbon monoxide and a nucleophilic trapping agent. The invention includes functionalized polymer, derivatives thereof and methods of making the same.

14 Claims, No Drawings

U.S. PATENT DOCUMENTS

| | | | |
|---|---|---|---|
| 3,493,520 | 2/1970 | Verdol et al. | 252/51.5 |
| 3,502,677 | 3/1970 | Le Suer | 260/268 |
| 3,513,093 | 5/1970 | Le Suer | 252/32.5 |
| 3,522,179 | 7/1970 | Le Suer | 252/51.5 |
| 3,527,779 | 9/1970 | Paulis et al. | 260/413 |
| 3,533,945 | 10/1970 | Vogel | 252/49.6 |
| 3,539,633 | 11/1970 | Piasek et al. | 260/570.5 |
| 3,539,654 | 11/1970 | Pautrat et al. | 260/768 |
| 3,541,012 | 11/1970 | Stuebe | 252/51.5 |
| 3,542,680 | 11/1970 | Le Suer | 252/57 |
| 3,551,466 | 12/1970 | Gee et al. | 260/429 |
| 3,558,743 | 1/1971 | Verdol et al. | 260/848 |
| 3,573,205 | 3/1971 | Lowe et al. | 252/51.5 |
| 3,579,450 | 5/1971 | Le Suer | 252/56 |
| 3,595,942 | 7/1971 | Wald et al. | 260/880 |
| 3,600,372 | 8/1971 | Udelbefon | 260/132 |
| 3,639,242 | 2/1972 | Le Suer | 252/56 R |
| 3,649,659 | 3/1972 | Otto et al. | 260/429 R |
| 3,652,616 | 3/1972 | Watson et al. | 260/429 R |
| 3,681,415 | 8/1972 | Shell | 260/410.9 R |
| 3,692,681 | 9/1972 | Liston | 252/51.5 A |
| 3,697,428 | 10/1972 | Meinhardt et al. | 252/462 R |
| 3,703,536 | 11/1972 | Piasek et al. | 260/462 R |
| 3,708,522 | 1/1973 | Le Suer | 260/485 G |
| 3,711,406 | 1/1973 | Lowe | 252/33.4 |
| 3,715,313 | 2/1973 | Haseltine et al. | 252/52 |
| 3,718,663 | 2/1973 | Piasek et al. | 260/326.3 |
| 3,749,695 | 7/1973 | de Vries | 252/47.5 |
| 3,755,169 | 8/1973 | Adams et al. | 252/35 |
| 3,795,615 | 3/1974 | Pappas et al. | 252/59 |
| 3,859,318 | 1/1975 | Le Suer | 260/410.6 |
| 3,865,740 | 2/1975 | Goldschmidt | 252/46.7 |
| 3,865,813 | 2/1975 | Gergel | 260/239.3 R |
| 3,870,734 | 3/1975 | Onopchenko et al. | 260/413 |
| 3,903,003 | 9/1975 | Murphy et al. | 252/51.5 A |
| 3,910,963 | 10/1975 | Souma et al. | 260/343 |
| 3,954,639 | 5/1976 | Liston | 252/47.5 |
| 3,992,423 | 11/1976 | Massie | 260/410.6 |
| 4,073,737 | 2/1978 | Elliott | 252/51.5 A |
| 4,088,588 | 5/1978 | Pecoraro | 252/51.5 A |
| 4,102,798 | 7/1978 | Ryer et al. | 252/51.5 A |
| 4,108,945 | 8/1978 | Fetters et la. | 260/880 B |
| 4,113,639 | 9/1978 | Lonstrup et al. | 252/51.5 A |
| 4,116,876 | 9/1978 | Brois et al. | 252/49.6 |
| 4,156,128 | 5/1979 | Craven | 219/523 |
| 4,224,232 | 9/1980 | Onopchenko et al. | 260/413 |
| 4,234,435 | 11/1980 | Meinhardt et al. | 252/51.5 A |
| 4,256,913 | 3/1981 | Jung et al. | 562/521 |
| 4,262,138 | 4/1981 | Gelbein | 560/233 |
| 4,312,965 | 1/1982 | Jachimowicz et al. | 525/378 |
| 4,323,698 | 4/1982 | Haag et al. | 560/233 |
| 4,518,798 | 5/1985 | Kramer et al. | 560/233 |
| 4,539,654 | 9/1985 | Deyer | 364/900 |
| 4,611,086 | 9/1986 | Gueguen et al. | 568/897 |
| 4,665,174 | 5/1987 | Minai et al. | 544/59 |
| 4,668,834 | 5/1987 | Rim et al. | 585/12 |
| 4,681,707 | 7/1987 | Alper et al. | 260/410.9 R |
| 4,704,427 | 11/1987 | Kitahara et al. | 524/531 |
| 4,717,755 | 1/1988 | Doi et al. | 525/333.7 |
| 4,797,219 | 1/1989 | Gutierrez et al. | 252/56 D |
| 4,798,873 | 1/1989 | Meurer et al. | 525/333.7 |
| 4,857,217 | 8/1989 | Gutierrez et al. | 252/47 |
| 4,866,135 | 9/1989 | Gutierrez et al. | 525/285 |
| 4,866,139 | 9/1989 | Gutierrez et al. | 525/333.7 |
| 4,866,140 | 9/1989 | Gutierrez et al. | 525/333.7 |
| 4,866,141 | 9/1989 | Gutierrez et al. | 525/333.7 |
| 4,866,142 | 9/1989 | Gutierrez et al. | 525/333.7 |
| 4,902,822 | 2/1990 | Drent | 560/233 |
| 4,906,394 | 3/1990 | Gutierrez et al. | 252/51.5 A |
| 4,927,892 | 5/1990 | Drent et al. | 525/340 |
| 4,929,689 | 5/1990 | Meurer et al. | 525/333.9 |
| 4,952,739 | 8/1990 | Chen | 585/18 |
| 4,956,107 | 9/1990 | Gutierrez et al. | 252/47 |
| 4,963,275 | 10/1990 | Gutierrez et al. | 252/47 |
| 4,980,422 | 12/1990 | Willis | 525/370 |
| 5,017,199 | 5/1991 | Etchepare | 55/57 |
| 5,017,299 | 5/1991 | Gutierrez et al. | 252/51.5 R |
| 5,049,294 | 9/1991 | Van Zon et al. | 252/51.5 A |
| 5,070,131 | 12/1991 | Rhodes et al. | 524/484 |
| 5,084,534 | 1/1992 | Welborn, Jr. et al. | 526/160 |
| 5,102,566 | 4/1992 | Fetterman, Jr. et al. | 252/32.7 E |
| 5,229,022 | 7/1993 | Sing et al. | 256/56 |

FUNCTIONALIZATION OF POLYMERS BASED ON KOCH CHEMISTRY AND DERIVATIVES THEREOF

This is a continuation of application Ser. No. 08/520,323, filed Aug. 28, 1995 now abandoned, which is a division of application Ser. No. 07/992,403, filed Dec. 17, 1992 now abandoned.

BACKGROUND OF THE INVENTION

1. Field of the Invention

The present invention is directed to an improved polymer and method to make it, more particularly the invention relates to an polymer having at least one carbon-carbon double bond reacted, according to the Koch reaction mechanism, with carbon monoxide in the presence of an acidic catalyst to form a carbonyl or thiocarbonyl functional group, and derivatives thereof.

2. Description of Related Art

For the purpose of the present invention the term "polymer" is defined as a large molecule built up by the repetition of small, simple chemical units. (Billmeyer, J. R., Textbook of Polymer Sciences, 2nd Ed., J. Wiley p.3 (1971). Polymers are considered to be defined by average properties, and shall be considered to have a number average molecular weight of at least 500.

For the purpose of the present invention the term "hydrocarbon" refers to a compound comprising hydrogen and carbon which has specific or precise properties (i.e., molecular weight) in contradistinction to polymeric materials which have average properties such as average molecular weight. However, the term "hydrocarbon" is not intended to exclude mixtures of different materials which individually are characterized by such specific and precise properties. Both hydrocarbon compounds as well as polymeric compounds have been reacted to form carboxyl group containing compounds and their derivatives.

Carboxyl groups have the general formula

where R can be H, a hydrocarbyl group or a substituted hydrocarbyl group.

The synthesis of carboxyl group containing compounds from olefinic hydrocarbon compounds, carbon monoxide and water in the presence of metal carboxyls is disclosed in references such as N. Bahrmann, Chapter 5, Koch Reactions, of the text "New Synthesis with Carbon Monoxide" edited by J. Falbe; Springer-Verlag, New York, N.Y. 1980. In accordance with the disclosed Koch reactions, hydrocarbon compounds having olefinic double bonds are disclosed to react in two steps to form carboxylic acid-containing compounds. In the first step an olefin compound reacts with an acid catalyst and carbon monoxide in the absence of water. This is followed by a second step in which the intermediate formed during the first step undergoes hydrolysis or alcoholysis to form a carboxylic acid or ester. An advantage of the Koch reaction is that it can occur at moderate temperatures of −20° C. to +80° C., and pressures up to 100 bar.

Bahrmann et al. disclose a mechanism for a Koch reaction wherein an olefinic hydrocarbon compound is reacted with an acid catalyst and carbon monoxide. A hydrogen compound having the formula:

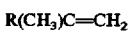

is reacted with an acid such as sulfuric acid and carbon monoxide. Initially, a carbenium ion forms having the formula:

The carbenium ion reacts with carbon monoxide (CO) to form an acylium cation having the formula:

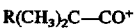

The acylium cation can then be hydrolyzed with an alcohol or water to form an ester or an acid having the formula:

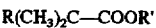

where R is a hydrocarbon and R' is H or a hydrocarbon.

The Koch reaction can occur at double bonds where at least one carbon of the double bond is di-substituted to form a "neo" acid or ester (i.e.

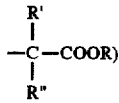

Bahrmann et al. discloses isobutylene converted to isobutyric acid via a Koch-type reaction. The Koch reaction can also occur when both carbons are monosubstituted or one is monosubstituted and one is unsubstituted to form an "iso" acid (i.e. $R_2HC-COOR$).

U.S. Pat. No. 2,831,877 discloses a multi-phase, acid catalyzed, two-step process for the carboxylation with carbon monoxide of olefins such as ethylene, propene, butene, isobutene or higher molecular weight olefins such as nonene, hexadecene and the like. This early reference points to considerations including yield and catalyst separation from the product. Disclosed catalysts include Broensted acids such as $H_2SO_4$, HF, $H_3PO_4$ as well as Broensted acids used in combination with Lewis acids. Useful Lewis acids include $BF_3$. It is disclosed that a system of $BF_3 \cdot H_2O$ and methanol usually requires around 100 bar and temperatures of 100° C. Milder conditions are reported with $H_2SO_4$ and $H_3PO_4$ (25/100 bar CO pressure and 20°/100° C.). Very mild conditions are disclosed with HF. Good yields are reported for methyl esters obtained in the presence of $BF_3 \cdot CH_3OH$. It is reported that depending on the weight ratio of $BF_3$ to $H_2O$ the system can be homogeneous (ratio 1:1) or heterogeneous (ratio 1:2). The heterogeneous system has been reported to exhibit higher activity.

U.S. Pat. No. 2,967,873 to Koch et al. is directed to a process for the production of aliphatic and cycloaliphatic monocarboxylic acid alkyl esters. The process entails the exposure of an olefin and carbon dioxide to the presence of a catalyst. The catalyst disclosed is a mixture of a hydroxy fluoroboric acid and an alkoxy fluoroboric acid. The background of this patent discloses that catalysts including monohydroxy fluoroboric acid as well as the hydronium salt of this acid have been used. The olefinic materials described include a variety of materials including 2-methylpent-1-ene, diisobutene, isododecene, isopentadecene, and isononene prepared by polymerization of propene, olefins from the cleavage of oil products, and also dimers produced by the process of K. Ziegler. Alcohols useful in the method disclosed include methanol, ethanol and then propanol.

Complexes of mineral acids in water with $BF_3$ have been studied to carboxylate olefins. U.S. Pat. No. 3,349,107 discloses processes which use less than a stoichiometric amount of acid as a catalyst. Examples of such complexes are $H_2O.BF_3.H_2O$, $H_3PO_4.BF_3.H_2O$ and $HF.BF_3.H_2O$.

Sulfuric acid is known to be used as a catalyst in Koch reactions as disclosed in Bahrmann, cited above. Bahrmann refers to Y. Komatsu et al., Maruzen Sekiyo Gihi 21, 51 (1976) regarding the use of 85% sulfuric acid as a catalyst for carboxylation of tertiary olefins in the presence of trichloroethylene as a solvent. Chlorinated solvents are used to isolate the neo acid in the acid mixture. Other disclosures using sulfuric acid include the use of mixtures of phosphoric and sulfuric acids as catalysts especially in the presence of copper salts, H. Kawasaki et al., J62164-645-A. The sulphonate which forms is disclosed to result in color, odor and acid quality problems and can be inhibited by the disclosed procedure. The presence of substantial quantity of phosphoric acid in the catalyst also induces phase separation in the product/catalyst recovery step.

Ya Eidus et al., Z. Org. Chem. 4 (3) 376 (1968) discloses the use of phosphoric acid as a catalyst system which permits phase separation of the reaction products. However, the application of pure $H_3PO_4$ compared to $H_2SO_4$ necessitates more severe reaction conditions (75/200 bar instead of 70/80 bar and 125°/150° C. instead of 10°/50° C.). Bahrmann discloses that $H_3PO_4/BF_3$ permits excellent separation of reaction products.

Hydrogen fluoride, HF, catalyst has been disclosed to be used in pure form as well as in an aqueous solution. Yields of greater than 95% have been obtained at high catalyst concentrations $HF:olefin:H_2O$ of 10:1:1. The low boiling point of hydrogen fluoride has been suggested to be an advantage for catalyst separation via pressure distillation. References such as U.S. Pat. No. 3,527,779 suggest that acid strength of the catalyst has a marked effect on the rate and selectivity of the Koch reaction. Examples of acid strength on the selectivity of pivalic acid are disclosed in the '779 patent. Strong acid catalysts promote the isomerization of linear unbranched olefins (carbon number greater than or equal to 4) to form highly branched unsaturates. This is particularly relevant to the Koch reaction since by proper control of reaction conditions it is possible to carboxylate linear olefins to form iso acids. The use of more severe reaction conditions promotes isomerization of the carbon backbone which, followed by carboxylation, results in the formation of neo acids.

Temperature and pressure are disclosed by Bahrmann to affect the reactants, intermediates and final products in the Koch reaction. An increase in reaction temperature generally has a favorable effect on neo acid yield. The magnitude of the temperature effect on selectivity depends on the acid strength of the catalyst with the weaker the catalyst the stronger the temperature effect. It is disclosed that the position and rate of attainment of equilibrium of the following reactions are determined by the temperature: dehydration/hydration esterification/saponification (with alcoholic starting materials); isomerization of the carbenium ions; oligomerization/depolymerization of carbenium ions; and carboxylation/decarboxylation.

Bahrmann et al. disclose that, generally higher yields and more uniform products are achieved at high CO pressures. This is due to the trapping of the carbenium ion (via transformation into acyl complexes) which supresses the isomerization and oligomerization thereby preventing the formation of a series of by-products.

High levels of CO and sulfuric acid can be obtained by the addition of anhydrous formic acid to the reaction median. Formic acid decomposes in strong acid at room temperature to form CO and water. The rate of decomposition of formic acid is acid strength dependent.

The amount of stirring can affect the yield of carboxylic acids in a Koch-type reaction mechanism using formic acid as a CO source. Less stirring results in more secondary carbenium ions resulting in iso-carboxylic acids. It has also been reported that the conversion of 1-hexene in the presence of $BF_3.H_2O$ resulted in increased neo acid content in the product increased on raising temperature from 20° C. to 100° C. and on decreasing CO pressure from 85 to 27 bar (Gushcin, et al.; Neftekhimiya 12 (3) 383 (1972), Chem. Inf. 41 (1972) which was referred to in Bahrmann).

Other considerations reported by Bahrmann et al. which can determine the outcome of a Koch reaction include the catalyst to olefin mole ratio, the product and catalyst recovery, and the reactor throughput and residence time.

The use of a solvent can affect product/catalyst recovery. However, Onopchenko, A. et al., DE2811867 (Mar. 18, 1978) disclose that with higher alpha olefins (greater than 16 carbons in length), higher yields of carboxylic acids were obtained in the absence of a solvent. Disclosed solvents for use in Koch systems include saturated hydrocarbons such as n-heptane, cyclohexane, methylcyclohexane, isooctane, benzene, chlorobenzene, chloroform, trichloroethylene, tetrachloroethylene, methylene chloride, trifluoro and trichloro ethane, carbon tetrachloride, fluorobenzene or mixtures thereof.

European Patent Publication No. 0,148,592 relates to the production of carboxylic acid esters and/or carboxylic acids by catalyzed reaction of a polymeric hydrocarbon having carbon-carbon double bonds, carbon monoxide and either water or an alcohol, optionally in the presence of oxygen. The catalysts can be selected from metals such as palladium, rhodium, ruthenium, iridium, and cobalt in combination with a copper compound. The reaction is conducted in the presence of a protonic acid which can include hydrochloric acid, sulfuric acid or an organic acid which can be a carboxylic acid. The reaction using transition metal catalysts is described as an oxycarbonylation, (see, for example, Wender, I, Organic Synthesis via Metal Carbonyls, Volume 2). Useful alcohols are disclosed in '592 to include $R_2CHOH$, wherein R is independently hydrogen, alkyl, aryl, or hydroxyalkyl or the two groups R together form a ring. The carbon monoxide pressure may be the autogeneous pressure at the reaction temperature of 2 to 250 psig above autogeneous pressure. The reaction can be conducted in the presence or absence of oxygen with oxygen preferred for improved yields. Optionally, and preferably, hydrocarbon solvents are used. The reaction is conducted at from 20° to 150° C. for 30 minutes to 8 hours. A preferred polymer is indicated to have at least 30% of its carbon-carbon double bonds in the form of terminal double bonds. Example polymers include butene polymers, ethylene copolymers and terpolymers, and vinyl aromatic diene copolymers. The polymeric compound containing a carbon-carbon double bond can be a hydrocarbon polymer containing greater than 20, for example, greater than 30 carbon atoms. A disclosed polymer is butene polymer, a preferred butene polymer is known as polyisobutylene, sometimes referred to as polyisobutene (PIB) which can be a low to medium molecular weight liquid product obtained from polymerization of at least partially purified isobutylene feeds. Examples of suitable polyisobutylenes include liquid polyisobutylenes having a number average molecular weight in the range of from 200 to 2,500, preferably up to 1,000.

U.S. Pat. No. 4,681,707 relates to a process for the production of carboxylic acid ester and/or a carboxylic acid which process comprises reacting an unsaturated hydrocarbon with carbon monoxide and either an alcohol or water in the presence of a protonic acid and a catalyst. The catalyst system and the alcohol are the same as disclosed in EP No. 0,148,592 referred to above. The carboxylic acid is produced from an unsaturated compound containing 2 to 30 carbon atoms.

U.S. Pat. No. 4,902,822 discloses a process for the preparation of carboxylic acids or of esters thereof by contacting an olefinic unsaturated compound with carbon monoxide in the presence of water or an alcohol, respectively, and of a catalytic system prepared by combining a ruthenium compound and a compound having a non-coordinating ion of an acid with a $pK_a$ below 0.5. The olefinic compounds are disclosed to have from 2 to 30 carbon atoms. The non-coordinating anion is of an acid which can include sulfuric acid, sulfonic acid, or of an acid that can be formed by interaction of a Lewis acid with a Broensted acid. Examples of such Lewis acids include $BF_3$. The alcohols which are used are disclosed to include aliphatic, cycloaliphatic or aromatic and may be substituted with one or more substituents. The alcohol may include a phenol, including alkyl substituted phenol.

U.S. Pat. No. 4,927,892 relates to reacting a polymer or copolymer of a conjugated diene at least part of which is formed by 1,2 polymerization wherein the α-carbon to the carboxyl group is unsubstituted with carbon monoxide and water and/or alcohol in the presence of a catalyst prepared by combining a palladium compound, certain ligands and/or acid except hydrohalogenic acids having a $pk_a$ of less than 2. Useful Lewis acids include $BF_3$.

U.S. Pat. No. 4,312,965 relates to a process of forming polymeric polyamines/amides by reacting an olefinic polymer derived from monomers having multiple olefinic double bond, with carbon monoxide, water and ammonia or amine in the presence of a rhodium catalyst.

The reaction at olefinic sites on hydrocarbons with carbon monoxide and water has been addressed in U.S. Pat. No. 3,059,007. This reference relates to improvements in the production of carboxylic acids from monoolefins, carbon monoxide and water. The reaction is conducted at a temperature of −25° C. to 100° C., at a pressure of 20 to 150 atmosphere in the presence of a highly acidic inorganic catalyst. The only disclosed catalyst was a mixture of $H_3PO_4$, $BF_3$ and water in a molar ratio of 1:1:1. The olefins are disclosed to have at least three carbons. The acid formed is secondary or tertiary. Available unsaturated charge materials comprise unsaturated hydrocarbons, particularly monoolefins such as propylene, butylene-1, butylene-2, isobutylene, branched or unbranched pentenes, hexenes, heptenes, octenes, nonenes, decanenes and high alkenes. Diisobutylene, propylene tetramer; cycloalkenes such as cyclopentenes and cyclohexenes are characterized as useful polymers and copolymers.

U.S. Pat. No. 3,992,423 is directed to the production of carboxylic acids from olefins with a catalyst comprising a zeolite in an aluminum hydrosol. In particular, carboxylic acids are prepared by a process which comprises the treatment of an unsaturated hydrocarbon with a compound containing a hydroxy group and carbon monoxide in the presence of the zeolite catalyst.

Puzitskii et al., Carbonylation of Olefins and Alcohols With Carbon Monoxide in the Presence of a Catalyst System: $BF_3.H_2O$-liquid $SO_2$, N. D. Zielinski, Institute of Organic Chemistry, Academy of Sciences of the U.S.S.R., Moscow, translated from Izvestiya Academii Nauk SSR, Seriya Khimicheskaya, No. 10, pp. 2331–2334, October, 1977. Original article submitted Jan. 4, 1977, published by the Plenum Publishing Company, 1978. This article discloses that it was known that olefins, with branching at the double bond, and tertiary alcohols in a mixture with methanol or ethanol are selectively carbonylated to esters under mild conditions (−70° C., atmospheric pressure) in the presence of the catalyst system $SbCl_3$-HCl-liquid $SO_2$. The Puzitskii paper discloses that branched hydrocarbon olefins and tertiary alcohols are easily carbonylated under mild conditions (−30° C., atmospheric pressure) in the presence of the catalyst system $BF_3.H_2O$-liquid $SO_2$. Liquid $SO_2$, as a solvent with a high dielectric constant facilitates the formation of carbenium and acylium ions from olefins or alcohols and CO. Liquid $SO_2$ has been found to have an effect on CO by facilitating its polarization and activity.

U.S. Pat. No. 4,262,138 discloses a process wherein ethylene or propylene are carbonylated with carbon monoxide to form carboxylic acid esters in the presence of a catalyst complex of one mole of $BF_3$ and one mole of alcohol.

U.S. Pat. No. 4,256,913 discloses that propylene and ethylene may be carbonylated to form carboxylic acids or carboxylic esters in the presence of a catalyst complex containing one mole of $BF_3$ and one mole of a second complexing component. In the case of the formation of the ester, the second complexing component is an alcohol, while in the case of the preparation of carboxylic acid, the second complexing component is water. It is disclosed that isobutyric acid and propionic acid formed from propylene and ethylene, respectively, in the presence of $BF_3.H_2O$ catalyst may be dehydrogenated to prepare methacrylic acid and acrylic acid respectively.

U.S. Pat. No. 4,717,755 describes production of a propylene homopolymer or copolymer having a terminal carboxyl group by polymerizing with $V(aceylacetonate)_3$ and $Al(C_2H_5)_2Cl$ and terminating the polymerization with carbon monoxide.

U.S. Pat. No. 4,704,427 teaches a method of modifying a rubber including subjecting the rubber to a carboxylation with, inter alia, carbon monoxide in the presence of a metal carbonyl compound. Chemical Abstracts '77 (12) 76298 likewise discloses a method of reacting a rubber with carbon monoxide in the presence of a metal carbonyl compound to introduce carboxyl groups into the rubber.

U.S. Pat. No. 4,980,422 teaches functionalizing a polymerized conjugated diene by contacting it with carbon monoxide and an alcohol in the presence of a catalyst comprising an amine ligand and a cobalt compound. The polymers formed having appended ester groups or terminal carboxyl groups when the α-carbon carboxyl group is unsubstituted.

U.S. Pat. No. 4,798,873 relates to carboxylic acid functionalized polyolefins prepared by olefin polymerization using organometallic catalysts followed by carbonylation with $CO_2$.

Other disclosures of interest include U.S. Pat. Nos. 4,929,689; 4,539,654; 3,910,963; 4,323,698; 4,224,232; 3,870,734; 4,717,755; 4,518,798; 2,586,070 and Japanese Ref. 51-41320.

Polymers functionalized with carboxylic acid, ester and the like groups, are useful for a variety of purposes. For example, U.S. Pat. No. 3,903,003 teaches the use of a terminally carboxylated, substantially completely hydrogenated polyisoprene which is reacted with a polyalkylene amine or hydroxyl polyalkylene amine and formed into a lubricating composition. There is particularly disclosed a polymerization of isoprene using a lithium based initiator.

The polymer produced is referred to as a living polymer with the end of the polymer chain associated with the lithium radical. The lithium polymer is subjected to carboxylation such as by reaction with carbon dioxide to form a polyisoprene having a terminal carboxyl group.

U.S. Pat. No. 4,857,217 teaches a dispersant additive which is an adduct of (a) a polyolefin substituted with dicarboxylic acid producing moieties and (b) an amidoamine or thioamidoamine. A functionalized polymer which was used in the foregoing dispersant and lubricant compositions is an alkenyl succinic anhydride produced by reacting maleic anhydride and polyisobutylene. The polymer to be substituted with the dicarboxylic acid is described as a polyolefin polymer or copolymer which can be made by a variety of means and reacted with a $C_4$ to $C_{10}$ unsaturated dicarboxylic acid, anhydride or ester. The olefin and dicarboxylic acid material can be reacted by simply heating together, as disclosed in U.S. Pat. Nos. 3,361,673 and 3,401,118, to cause a thermal "ene" reaction to take place. Alternatively, the olefin polymer can first be halogenated, for example, chlorinated or brominated at a temperature of from 60° C. to 250° C. The halogenated polymer can then be reacted with sufficient unsaturated acid or anhydride so that the product obtained will contain the desired number of moles of unsaturated acid per mole of halogenated polymer. There is no disclosure of reacting an unsaturated polymer in accordance with Koch-type chemistry to incorporate a carboxyl group.

SUMMARY OF THE INVENTION

The present invention relates to a polymer or copolymer functionalized with at least one carboxylic acid, carboxylic ester or thiol ester functional group. The functionalized polymer is derived from a polymer comprising at least one non-aromatic carbon-carbon double bond, also referred to as an olefinically unsaturated bond, or an ethylenically unsaturated bond. The polymer is functionalized at the point of olefin unsaturation via a Koch reaction to form the carboxylic acid, carboxylic ester or thiol ester.

Koch reactions are known in the art as presented by Bahrmann et al. referred to in the Background. However, this reaction has not heretofore been applied to polymers having number average molecular weights greater than 500 and preferably greater than 1,000. In accordance with the present invention, a Koch process comprises contacting a polymer composition comprising at least one polymer having at least one carbon-carbon double bond, with an acid catalyst and carbon monoxide in the presence of water or alcohol. The catalyst is preferably a classical Broensted acid or Lewis acid catalyst. These catalysts which are useful for Koch reactions, are distinguishable from transition metal catalysts of the type useful in hydroformylation as described above. The Koch reaction is conducted in a manner and under conditions sufficient to form a carbenium ion at the site of said carbon-carbon double bond. The carbenium ion is reacted with carbon monoxide to form an acylium cation, which in turn is reacted with at least one nucleophilic trapping agent selected from the group consisting of water or at least one hydroxyl or one thiol group containing compound. The Koch reaction as applied to polymers in accordance with the present invention has resulted in yields of functionalized polymer of at least 40, preferably at least 50, more preferably at least 80, yet more preferably at least 90 mole % of the polymer reacting to form acylium cations which form functional groups, e.g. carbonyl functional groups.

The composition of the present invention comprises functionalized polymer of the formula:

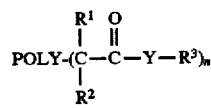

POLY represents polymer functionalized by the parenthetical substituent and having a number average molecular weight of at least about 500, and in specific embodiments the following number average molecular weight ranges, at least about 2,500; at least about 2,800; at least about 3,000; from 500 to 15,000,000; 500 to 20,000; 500 to 10,000; 1,000 to 10,000; 1,500 to 5,000; 20,000 to 200,000; 20,000 to 100,000; 25,000 to 80,000; and 25,000 to 60,000.

POLY- is derived from unsaturated polymer. Preferred unsaturated polymers include those selected from the group consisting of polyalkenes derived from monoolefinic monomers, diolefinic monomers and copolymers thereof.

The letter n is greater than 0 and represents the functionality (F) of the functionalized polymer wherein the functional group is represented by the formula:

which functional group contains the acyl group

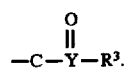

Specific embodiments of n include $1 \geq n > 0$; $2 \geq n > 1$; and $n > 2$. n can be determined by $C^{13}$ NMR. The number of functional groups needed for desired performance will typically increase with number average molecular weight of the polymer. In effect, there can be a controlled number of functional groups per total molecular weight of polymer. The maximum value of n will be determined by the number of double bonds per polymer chain in the unfunctionalized polymer.

$R^1$ and $R^2$ can be the same or different and are selected from —H, a hydrocarbyl group and a polymeric group.

Y is selected from the group consisting of O, and S.

$R^3$ is selected from H, hydrocarbyl, and a polymeric groups, wherein the hydrocarbyl group can include alkyl groups, hetero-substituted hydrocarbyl groups, aromatic groups, substituted aromatic groups and hetero-substituted aromatic groups.

In specific and preferred embodiments the "leaving group" (—$YR^3$) has a pKa of less than or equal to 12, preferably less than 10, and more preferably less than 8. The pKa is determined from the corresponding acidic species HY—$R^3$ in water at room temperature.

Where the leaving group is a simple acid or alkyl ester, the system is very stable especially when the % neo substitution increases. However, as will be described below, when the leaving groups are more stable, these compounds are more difficult to derivatize.

The present invention is especially useful to make "neo" functionalized polymer which are generally more stable and less labile than iso structures. By neo structure, it is meant that $R^1$ and $R^2$ are selected such that at least 50 mole % of the

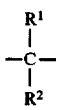

groups of Formula I do not have both $R^1$ and $R^2$ represented by hydrogen, but preferably a group such as a hydrocarbyl group. In more specific embodiments the polymer can be at least 50, more specifically at least 60, yet more specifically at least 80 mole percent neo. The polymer can be greater than 90, or 99 and even about 100 mole percent neo.

In one preferred composition the polymer defined by formula (I), Y is O (oxygen), $R^1$ and $R^2$ can be the same or different and are selected from H, a hydrocarbyl group, and a polymeric group.

In another preferred embodiment Y is O or S, $R^1$ and $R^2$ can be the same or different and are selected from H, a hydrocarbyl group a substituted hydrocarbyl group and a polymeric group, and $R^3$ is selected from a substituted hydrocarbyl group, an aromatic group and a substituted aromatic group. This embodiment is generally more reactive towards derivatization with amines and alcohol compounds especially where the $R^3$ substituent contains electron withdrawing species. It has been found that in this embodiment, a preferred leaving group, $HYR^3$, has a pKa of less than 12, preferably less than 10 and more preferably 8 or less. The pKa of the leaving group determines how readily the system will react with derivatizing compounds to produce derivatized product.

In a particularly preferred composition, $R^3$ is represented by the formula:

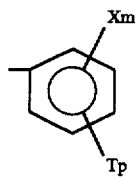

wherein X, which may be the same or different, is an electron withdrawing substituent, T, which may be the same or different, represents a non-electron withdrawing substituent (e.g. electron donating), and m and p are from 0 to 5 with the sum of m and p being from 0 to 5. More preferably, m is from 1 to 5 and preferably 1 to 3. In a particularly preferred embodiment X is selected from a halogen, preferably F, Cl and $CF_3$, cyano groups and nitro groups and p=0. A preferred $R^3$ is derived from 2,4-dichlorophenol.

The composition of the present invention includes derivatized polymer which is the reaction product of the Koch functionalized polymer and a derivatizing compound. Preferred derivatizing compounds include nucleophilic reactant compounds including amines, alcohols, amino-alcohols, metal reactant compounds and mixtures thereof. Derivatized polymer will typically contain at least one of the following groups: amide, imide, oxazoline, and ester, and metal salt. The particular end use of the derivatized polymer will control the polymer Mn and functionality.

The Koch reaction permits controlled functionalization of unsaturated polymers. When a carbon of the carbon-carbon double bond is substituted with hydrogen, it will result in an "iso" functional group, i.e. one of $R^1$ or $R^2$ of Formula I is H; or when a carbon of the double bond is fully substituted with hydrocarbyl groups it will result in a "neo" functional group, i.e. both $R^1$ or $R^2$ of Formula I are non-hydrogen groups.

Polymers produced by processes which result in a terminally unsaturated polymer chain can be functionalized to a relatively high yield in accordance with the process of the present invention. In particular, it has been found that the neo acid functionalized polymer can be derivatized to a relatively high yield. This makes possible the use of relatively inexpensive materials i.e., carbon monoxide at relatively low temperatures and pressures. The leaving group $-YR^3$ can be removed and recycled upon derivatizing the Koch functionalized polymer with amines or alcohols.

The present invention includes oleaginous compositions comprising the above functionalized, and/or derivatized polymer. Such compositions include lubricating oil compositions and concentrates.

The process of the present invention relates to a polymer having at least one olefinic unsaturation reacted via a Koch mechanism to form the carbonyl or thiol carbonyl group-containing compounds as well as derivatives thereof. The polymers react with carbon monoxide in the presence of an acid catalyst or a catalyst complexed with a nucleophilic trapping agent. A preferred catalyst is $BF_3$ and preferred catalyst complexes include $BF_3 \cdot H_2O$ and $BF_3$ complexed with 2,4-dichlorophenol. The starting polymer reacts with carbon monoxide at points of unsaturation to form either iso- or neo-acyl groups with the nucleophilic trapping agent, e.g. water, alcohol (preferably a substituted phenol) or thiol to form respectively a carboxylic acid, carboxylic ester group, or thio ester.

Without wishing to be bound by any particular theory, it is believed that when at least one polymer having at least one carbon-carbon double bond, is contacted with an acid catalyst or catalyst complex having a Hammett Scale acidity value of less than −7, preferably from −8.0 to −11.5, a carbenium ion will form at the site of one of the carbon-carbon double bonds. The carbenium ion then reacts with carbon monoxide to form an acylium cation. The acylium cation reacts with at least one nucleophilic trapping agent as defined herein. At least 40 mole %, preferably at least 50 mole %, more preferably at least 80 mole %, and most preferably 90 mole % of the polymer double bonds will react to form acyl groups wherein the non-carboxyl portion of the acyl group is determined by the identity of the nucleophilic trapping agent, i.e. water forms acid, alcohol forms acid ester and thiol forms thio ester.

The polymer functionalized by the recited process of the present invention can be isolated using fluoride salts. The fluoride salt can be selected from the group consisting of ammonium fluoride, and sodium fluoride.

Preferred nucleophilic trapping agents are selected from the group consisting of water, monohydric alcohols, polyhydric alcohols, hydroxyl-containing aromatic compounds and hetero substituted phenolic compounds. The catalyst and nucleophilic trapping agent can be added separately or combined to form a catalytic complex.

The functionalized or derivatized polymers of the present invention are useful as lubricant additives such as dispersants, viscosity improvers and multifunctional viscosity improvers.

Although there are disclosures in the art of olefinic hydrocarbons functionalized at the carbon-carbon double bond to form a carboxylic acid or derivative thereof via Koch-type chemistry, there is no disclosure that polymers containing carbon-carbon double bonds, including terminal olefinic bonds, either secondary or tertiary type olefinic bonds, could be successfully reacted via the Koch mechanism. Additionally, it has been found that the process of the present invention is particularly useful to make neo acid and neo ester functionalized polymer. Known catalysts used to carboxylate low molecular weight olefinic hydrocarbons by the Koch mechanism were found to be unsuitable for use with polymeric material. Specific catalysts have been found which can result in the formation of a carboxylic acid or ester at a carbon-carbon double bond of a polymer. While Koch chemistry affords the advantage of the use of moderate temperatures and pressures, it requires highly acidic catalysts and careful control of concentrations.

DESCRIPTION OF THE PREFERRED EMBODIMENTS

In accordance with the present invention, polymers comprising at least one non-aromatic carbon-carbon double bond, also referred to as an ethylenic or olefinic bond are reacted via a Koch mechanism with carbon monoxide to form a carboxylic acid, carboxylic ester or thiol ester functional group at the carbon-carbon double bond. The functional group can have an iso or neo type.

As used herein the term "hydrocarbyl" denotes a group having a carbon atom directly attached to the remainder of the molecule and having predominantly hydrocarbon character within the context of this invention. Such radicals include the following:

(1) Hydrocarbon groups; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, the two indicated substituents may together form a cyclic radical). Such radicals are known to those skilled in the art; examples include methyl, ethyl, butyl, hexyl, octyl, decyl, dodecyl, tetradecyl, octadecyl, eicosyl, cyclohexyl, phenyl and naphthyl (all isomers being included).

(2) Substituted hydrocarbon groups; that is, radicals containing non-hydrocarbon substituents which, in the context of this invention, do not alter the predominantly hydrocarbon character of the radical. Those skilled in the art will be aware of suitable substitutents (e.g., halo, hydroxy, alkoxy, carbalkoxy, nitro, alkylsulfoxy).

(3) Hetero groups; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen particularly non-basic nitrogen which would not deactivate the Koch catalyst, oxygen and sulfur.

In general, no more than about three substituents or hetero atoms, and preferably no more than one, will be present for each 10 carbon atoms in the hydrocarbon-based radical.

According to the present invention, the Koch reaction has been applied to polymers comprising at least one non-aromatic carbon-carbon double bond. Carbon monoxide, or carbon monoxide from a carbon monoxide source, is reacted with a carbon atom of a carbon-carbon double bond in the presence of a specifically selected acidic catalyst. In accordance with classical proposed Koch mechanistic theory the addition of the acidic catalyst results in the formation of a carbenium ion at the carbon-carbon double bond. A proton from the acidic catalyst combines with the double bond. There is subsequent addition of carbon monoxide to the carbenium ion to result in an acylium cation. Where the carbenium ion is secondary an iso acylium cation is formed. Where the olefinic unsaturation is such that a tertiary carbonation is generated a neo acylium cation forms. The iso and neo acylium cations are then reacted with what is referred to herein as a nucleophilic trapping agent, such as, water, a hydroxyl group-containing compound, such as an alcohol or a phenolic compound, and/or a thiol, to form carboxylic acid, carboxyl ester, or thioester, respectively. The neo acid or esters which form are particularly stable.

Following is an example of a terminally unsaturated polymer reacted via the Koch mechanism to form an acid or an ester. The polymer is contacted with carbon monoxide or a suitable carbon monoxide source such as formic acid in the presence of an acidic catalyst. The catalyst contributes a proton to the carbon-carbon double bond to form a carbenium ion. This is followed by addition of CO to form an acylium ion which reacts with the nucleophilic trapping agent. (POLY), $R^1$, $R^2$ and $R^3$ are defined as above.

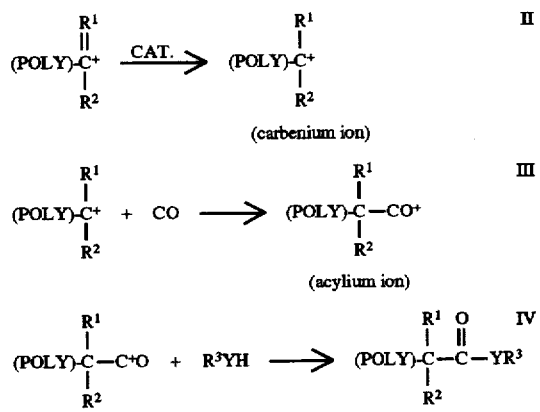

The Koch reaction is particularly useful to functionalize poly(alpha olefins) and ethylene alpha olefin copolymers formed using metallocene-type catalysts. These polymers contain terminal vinylidene groups. There is a tendency for such terminal groups to predominate and result in neo-type (tertiary) carbenium. ions. In order for the carbenium ion to form the acid catalysts must be relatively strong. However, the strength of the acid catalyst must be balanced against detrimental side reactions which can occur when the acid is too strong.

The Koch catalyst can be employed by preforming a catalyst complex with the proposed nucleophilic trapping agent or by adding the catalyst and trapping agent separately to the reaction mixture. This latter embodiment has been found to be a particular advantage since it eliminates the steep of making the catalyst complex.

It has been determined that the Koch catalyst or catalyst complex of the present invention should have a Hammett Scale Value acidity (Ho) of less than −7 in order to be sufficiently active to react with a polymer, particularly to form neo structures. However, Hammett acidities of less than −12 can cause undesirable side reactions. Therefore, a preferred range of Hammett acidity is from −8 to −11.5 and most preferably −10 to −11.5.

The following are acidic catalyst and catalyst complex materials and their respective Hammett Scale Value acidity: 60% $H_2SO_4$, −4.32; $BF_3.3H_2O$, −4.5; $BF_3.2H_2O$, −7.0; $WO_3/Al_2O_3$, less than −8.2; $SiO_2/Al_2O_3$, less than −8.2; HF, −10.2; $BF_3.H_2O$, −11.4; −11.94; $ZrO_2$ less than −12.7; $SiO_2/Al_2O_3$, −12.7 to −13.6; $AlCl_3$, −13.16 to −13.75; $AlCl_3/CuSO_4$ −13.75 to −14.52.

It has been found that $BF_3.2H_2O$ is ineffective at functionalizing polymer through a Koch mechanism ion with polymers. In contrast, $BF_3.H_2O$ resulted in high yields of carboxylic acid for the same reaction.

The use of $H_2SO_4$ as a catalyst involves control of the acid concentration to achieve the desired Hammett Scale Value range. Catalysts which are particularly useful for forming neo acids, are in the preferred Hammett Scale Value range of −8 to −11.5, with preferred catalysts being $H_2SO_4$ and $BF_3$.

Suitable $BF_3$ catalyst complexes for use in the present invention can be represented by the formula:

wherein R can represent hydrogen, hydrocarbyl (as defined below in connection with R')

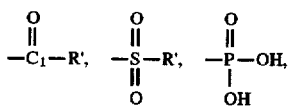

and mixtures thereof wherein R' is hydrocarbyl, typically alkyl, e.g., C, to $C_{20}$ alkyl, and, e.g., $C_6$ to $C_{14}$ aryl, aralkyl, and alkaryl.

The carbenium ion reacts with CO to form acylium cation. The acylium cation can be further reacted with water or another nucleophilic trapping agent such as an alcohol or phenolic, or thiol compound. The use of water releases the catalyst to form an acid. The use of hydroxy trapping agents releases the catalyst to form an ester, the use of a thiol releases the catalyst to form a thio ester.

Koch product, also referred to herein as functionalized polymer, typically will be derivatized as described hereinafter. Derivatization reactions involving ester functionalized polymer will typically have to displace the alcohol derived moiety therefrom. Consequently, the alcohol derived portion of the Koch functionalized polymer is sometimes referred to herein as a leaving group. The ease with which a leaving group is displaced during derivatization will depend on its acidity, i.e. the higher the acidity the more easily it will be displaced. The acidity in turn of the alcohol is expressed in terms of its pKa.

Preferred nucleophilic trapping agents include water and hydroxy group containing compounds. Useful hydroxy trapping agents include aliphatic compounds such as monohydric and polyhydric alcohols or aromatic compounds such as phenols and naphthols. The aromatic hydroxy compounds from which the esters of this invention may be derived are illustrated by the following specific example: phenol, -naphthol, cresol, resorcinol, catechol, 2-chlorophenol. Particularly preferred is 2,4-dichlorophenol.

The alcohols preferably can contain up to about 40 aliphatic carbon atoms. They may be monohydric alcohols such as methanols, ethanol, isooctanol, dodecanol, cyclohexanol, cyclopentanol, neopentyl alcohol, isobutyl alcohol, benzyl alcohol, 2-methylcyclohexanol, beta-chloroethanol, monomethyl ether of ethylene glycol. The polyhydric alcohols preferably contain from 2 to about 5 hydroxy radicals. They are illustrated by, for example, ethylene glycol, diethylene glycol. Other useful polyhydric alcohols include glycerol, monomethyl ether of glycerol,and pentaerythritol.

Useful unsaturated alcohols include allyl alcohol, and propargyl alcohol.

Particularly preferred alcohols include those having the formula $R_2*CHOH$ where an R* is independently hydrogen, an alkyl, aryl, hydroxyalkyl, or cycloalkyl. Specific alcohols include alkanols such as methanol, ethanol, propanol, butanol, pentanol, hexanol as well as 2-ethyl hexanol. Also preferred useful alcohols include aromatic alcohols, phenolic compounds and polyhydric alcohols as well as monohydric alcohols such as 1,4-butanediol.

It has been found that neo-acid ester functionalized polymer, is extremely stable, due, it is believed to steric hindrance. Consequently, the yield of derivatized polymer obtainable therefrom will vary depending on the ease with which a derivatizing compound can displace the leaving group of the functionalized polymer.

Accordingly, it has been found that the yield of derivatized polymer can be significantly enhanced by controlling the acidity of the leaving group, e.g., the alcohol derived portion of the ester functionalized polymer. Thus, while any acidity which is effective to enable the leaving group —$YR^3$ of Formula (I) to be displaced during derivatization can be employed, it is contemplated that such effective acidities, expressed as the pKa of the compound $HYR^3$, be typically not greater than about 12, preferably not greater than about 10, and most preferably not greater than about 8, which pKa values can range typically from about 5 to about 12, preferably from about 6 to about 10, and most preferably from about 6 to about 8.

The most preferred alcohol trapping agents can be obtained by substituting a phenol with at least one electron withdrawing substituent such that the substituted phenol possesses a pKa within the above described pKa ranges. In addition, phenol can also be substituted with at least one non-electron withdrawing substituent (e.g., electron donating), preferably at positions meta to the electron withdrawing substituent to block undesired alkylation of the phenol by the polymer during the Koch reaction. This further improves yield to desired ester functionalized polymer.

Accordingly, and in view of the above, the most preferred trapping agents are phenolic and substituted phenolic compounds represented by the formula:

(V)

wherein X, which may be the same or different, is an electron withdrawing substituent, and T which may be the same or different is a non-electron withdrawing group; m and p are from 0 to 5 with the sum of m and p being from 0 to 5, and m is preferably from 1 to 5, and more preferably, m is 1 or 2. X is preferably a group selected from halogen, cyano, and nitro, preferably located at the 2- and/or 4-position, and T is a group selected from hydrocarbyl, and hydroxy groups and p is 1 or 2 with T preferably being located at the 4 and/or 6 position. More preferably X is selected from Cl, F, Br, cyano or nitro groups and m is preferably from 1 to 5, more preferably from 1 to 3, yet more preferably 1 to 2, and most preferably 2 located at the 2 and 4 locations relative to —OH.

The relative amounts of reactants and catalyst, and the conditions are controlled in a manner sufficient to functionalize typically at least about 40, preferably at least about 80, more preferably at least about 90 and most preferably at least about 95 mole % of the carbon-carbon double bonds initially present in the unfunctionalized polymer.

The amount of $H_2O$, alcohol, or thiol used should be at least the stoichiometric amount required to react with the acylium cations. It is preferred to use an excess of alcohol over the stoichiometric amount. The alcohol performs the dual role of reactant and diluent for the reaction. However, the amount of the alcohol or water used should be sufficient to provide the desired yield yet at the same time not dilute the acid catalyst so as to increase the Hammett Scale Value acidity above −7.

The polymer added to the reactant system can be in a liquid phase. Optionally, the polymer can be dissolved in an inert solvent. The yield can be determined upon completion of the reaction by separating polymer molecules which contain acyl groups which are polar and hence can easily be separated from unreacted non-polar compounds. Separation can be performed using absorption techniques which are known in the art. The amount of initial carbon-carbon double bonds and carbon-carbon double bonds remaining after the reaction can be determined by $C^{13}$ NMR techniques.

In accordance with the process, the polymer is heated to a desired temperature range which is typically between −20° C. to 200° C., preferably from 0° C. to 80° C. and more preferably from 40° C. to 65° C. Temperature can be controlled by heating and cooling means applied to the reactor. Since the reaction is exothermic usually cooling means are required.

Mixing is conducted throughout the reaction to assure a uniform reaction medium.

The catalyst (and nucleophilic trapping agent) can be prereacted to form a catalyst complex or are charged separately in one step to the reactor to form the catalyst complex in situ at a desired temperature and pressure, preferably under nitrogen. The nucleophilic trapping agent, preferably is a substituted phenol used in combination with $BF_3$. The reactor contents are continuously mixed and then rapidly brought to a desired operating pressure using a high pressure carbon monoxide source. Useful pressures can be up to 20,000 psig, and typically will be at least 300, preferably at least 800, and most preferably at least 1,000 psig, and typically will range from 500 to 5,000 psig preferably from 650 to 3,000 and most preferably from 650 to 2000 psig. The carbon monoxide pressure may be reduced by adding a catalyst such as a copper compound.

The catalyst to polymer molar ratio can range from 0.25 to 4, preferably 0.5 to 2 and most preferably 0.75 to 1.3.

Preferably, the polymer, catalyst, nucleophilic trapping agent and CO are fed to the reactor in a single step. The reactor contents are then held for a desired amount of time under the pressure of the carbon monoxide. The reaction time can range up to 5 hours and typically 0.5 to 4 and more typically from 1 to 2 hours. The reactor contents can then be discharged and the product which is a Koch functionalized polymer comprising either a carboxylic acid or carboxylic ester or thiol ester functional groups separated. Upon discharge, any unreacted CO can be vented off. Nitrogen can be used to flush the reactor and the vessel to receive the polymer.

Depending on the particular reactants employed, the functionalized polymer containing reaction mixture may be a single phase, a combination of a partitionable polymer and acid phase or an emulsion with either the polymer phase or acid phase being the continuous phase.

Upon completion of the reaction, the polymer is recovered by suitable means.

When the mixture is an emulsion, a suitable means can be used to separate the polymer. A preferred means is the use of fluoride salts, such as sodium or ammonium fluoride in combination with an alcohol such as butanol or methanol to neutralize the catalyst and phase separate the reaction complex. The fluoride ion helps trap the $BF_3$ complexed to the functionalized polymer and helps break emulsions generated when the crude product is washed with water. Alcohols such as methanol and butanol and commercial demulsifiers also help to break emulsions especially in combination with fluoride ions. Preferably, nucleophilic trapping agent is combined with the fluoride salt and alcohols when used to separate polymers. The presence of the nucleophilic trapping agent as a solvent minimizes tranesterification of the functionalized polymer.

Where the nucleophilic trapping agent has a pKa of less than 12 the functionalized polymer can be separated from the nucleophilic trapping agent and catalyst by depressurization and distillation. It has been found that where the nucleophilic trapping agent has lower pKa's, the catalyst, i.e. $BF_3$ releases more easily from the reaction mixture.

As indicated above, polymer which has undergone the Koch reaction is also referred to herein as functionalized polymer. Thus, a functionalized polymer is chemically modified to have at least one functional group present within its structure, which functional group is capable of: (1) undergoing further chemical reaction (e.g. derivatization) with other material/or (b) imparting desirable properties, not otherwise possessed by the polymer alone, absent such chemical modification.

It will be observed from the discussion of formula I that the functional group is characterized as being represented by the parenthetical expression

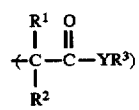

which expression contains the acyl group

It will be understood that while the

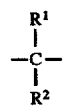

moiety is not added to the polymer in the sense of being derived from a separate reactant it is still referred to as being part of the functional group for ease of discussion and description. Strictly speaking, it is the acyl group which constitutes the functional group, since it is this group which is added during chemical modification. Moreover, $R^1$ and $R^2$ represent groups originally present on, or constituting part of, the 2 carbons bridging the double bond before functionalization. However, $R^1$ and $R^2$ were included within the parenthetical so that neo acyl groups could be differentiated from iso acyl groups in the formula depending on the identity of $R^1$ and $R^2$.

Characterization of the degree to which the polymer has been functionalized is referred to herein as "functionality". Functionality refers generally to the average number of functional groups present within the polymer structure per polymer chain. Thus, functionality can be expressed as the average number of moles of functional groups per "mole of polymer". When said "mole of polymer" in the functionality ratio includes both functionalized and unfunctionalized polymer, functionality is referred to herein as F which corresponds to n of Formula (I). When said "mole of polymer" includes only functionalized polymer, functionality is referred to herein as F*.

The distinction between F and F* arises when not all the polymer chains present in the reaction mixture are functionalized, e.g., because they have no unsaturation. In this instance typical analytical techniques employed to determine F* will normally necessitate identification of the weight fraction of functionalized polymer, based on the total weight of polymer (functionalized+unfunctionalized) in the sample being analyzed for functionality. This weight fraction is commonly referred to as Active Ingredient or A.I. Since the determination of A.I is a separate analytical step, it can be more convenient to express functionality as F rather than F*. In any event, both F and F* are alternate ways of characterizing the functionality.

As a general proposition, the polymer of the present invention can be functionalized to any functionality effective to impart properties suitable for the end use contemplated.

Typically, where the end use of the polymer is for making dispersant, e.g. as derivatized polymer, the polymer will possess dispersant range molecular weights ($\overline{Mn}$) as defined hereinafter and the functionality will typically be significantly lower than for polymer intended for making derivatized multifunctional V.I. improvers, where the polymer will possess viscosity modifier range molecular weights ($\overline{Mn}$) as defined hereinafter.

Accordingly, while any effective functionality can be imparted to functionalized polymer intended for subsequent derivatization, it is contemplated that such functionalities, expressed as F, can be for dispersant end uses, typically not greater than about 3, preferably not greater than about 2, and typically can range from about 0.5 to about 3, preferably from about 0.8 to about 2.0 ( e.g. 0.8 to about 1) .

Similarly, effective functionalities F for viscosity modifier end uses of derivatized polymer are contemplated to be typically greater than about 3, preferably greater than about 5, and typically will range from about 5 to about 10.

F and F* values can be interconnected using the AI which for polymers of the present invention typically are at least about 0.50, preferably from 0.65 to 0.99, more preferably from 0.75 to 0.99, yet more preferably 0.85 to 0.99. However, the upper limit of AI is typically from 0.90 to 0.99, and more typically 0.90 to 0.95. Where AI is 1.0, F=F*.

End uses involving very high molecular weight polymers contemplate functionalities which can range typically greater than about 20, preferably greater than about 30, and most preferably greater than about 40, and typically can range from about 20 to about 60, preferably from about 25 to about 55 and most preferably from about 30 to about 50.

Polymers

The polymers which are useful in the present invention are polymers containing at least one carbon-carbon double bond (olefinic or ethylenic) unsaturation. Thus, the maximum number of functional groups per polymer chain is limited by the number of double bonds per chain. Such polymers have been found to be receptive to Koch mechanisms to form carboxylic acids or derivatives thereof, using the catalysts and nucleophilic trapping agents of the present invention.

Useful polymers in the present invention include polyalkenes including homopolymer, copolymer (used interchangably with interpolymer) and mixtures. Homopolymers and interpolymers include those derived from polymerizable olefin monomers of 2 to about 16 carbon atoms; usually 2 to about 6 carbon atoms. The interpolymers are those in which two or more olefin monomers are interpolymerized according to well-known conventional procedures to form polyalkenes having units within their structure derived from each of said two or more olefin monomers. Thus, "interpolymer(s)" as used herein is inclusive of terpolymers, tetrapolymers and the like. As will be apparent to those of ordinary skill in the art, the polyalkenes from which the poly-substituent of Formula I are derived are often conventionally referred to as "polyolefin(s)".

Useful polymers include those described in U.S. Pat. Nos. 4,234,435, 5,017,299 and EP 0,462,319-A1, all hereby incorporated by reference. Particular reference is made to the alpha olefin polymers disclosed to be made using organo metallic coordination compounds. A particularly preferred class of polymers are ethylene alpha olefin copolymers such as those disclosed in U.S. Pat. No. 5,017,299, hereby incorporated by reference.

The polymers for use in this invention possess at least one carbon-carbon unsaturated double bond. The unsaturation can be terminal, internal or both. Preferred polymers have terminal unsaturation. The polymers of the present invention preferably comprise a high degree of terminal unsaturation. Terminal unsaturation is the unsaturation provided by the last monomer unit located in the polymer. The unsaturation can be located anywhere in this terminal monomer unit. Terminal olefinic groups include vinylidene unsaturation, $R^aR^bC{=}CH_2$; trisubstituted olefin unsaturation, $R^aR^bC{=}CR^cH$; vinyl unsaturation, $R^aHC{=}CH_2$; 1,2-disubstituted terminal unsaturation, $R^aHC{=}CHR^b$; and tetra-substituted terminal unsaturation, $R^aR^bC{=}CR^cR^d$. At least one of $R^a$ and $R^b$ is a polymeric group of the present invention, and the remaining $R^b$, $R^c$ and $R^d$ are hydrocarbon groups as defined with respect to R, $R^1$, $R^2$, and $R^3$ above.

The homopolymers and copolymers of the present invention can be conveniently characterized based on molecular weight range. Polymers and copolymers of low, intermediate and high molecular weights can be prepared.

Low molecular weight polymers, also referred to herein as dispersant range molecular weight polymers, are considered to be polymers having a number average molecular weight of less than 20,000, preferably from about 500 to about 20,000 (e.g. 1,000 to 20,000), more preferably from about 1,500 to about 10,000 (e.g. 2,000 to 8,000) and most preferably from 1,500 to 5,000. The low molecular weights are number average molecular weights measured by vapor phase osmometry. Low molecular weight polymers are useful in forming dispersants for lubricant additives Medium molecular weight polymers, also referred to herein as viscosity modifier range molecular weight polymers, have number average molecular weights ranging from 20,000 to 200,000, preferably 25,000 to 100,000; and more preferably, from 25,000 to 80,000 are useful for viscosity index improvers for lubricating oil compositions, adhesive coatings, tackifiers and sealants. The medium number average molecular weights can be determined by membrane osmometry.

The higher molecular weight materials have a number average molecular weight of greater than about 200,000 and can range from 201,000 to 15,000,000, and specific embodiment of 300,000 to 10,000,000 and more specifically 500,000 to 2,000,000. These polymers are useful in polymeric compositions and blends including elastomeric compositions. Higher molecular weight materials having number average molecular weights of from 20,000 to 15,000,000 can be measured by gel permeation chromatography with universal calibration, or by light scattering as recited in Billmeyer, Textbook of Polymer Science, Second Edition, pp. 81–84 (1971).

The values of the ratio Mw/Mn, also referred to as molecular weight distribution, (MWD) are not critical. However, a typical minimum Mw/Mn value of about 1.1–2.0 is preferred with typical ranges of about 1.1 up to about 4.

Useful olefin monomers from which the polyalkenes can be derived are polymerizable olefin monomers characterized by the presence of one or more unsaturated double bonds (i.e., >C=C<); that is, they are monoolefinic monomers such as ethylene, propylene, butene-1, isobutene, and octene-1 or polyolefinic monomers (usually diolefinic monomers) such as butadiene-1,3 and isoprene.

The polymer used in the invention can be derived from the polymerization of monomers selected from the group consisting of olefin, diolefin and mixtures to form homopolymers or copolymers.

These olefin monomers are preferably polymerizable terminal olefins; that is, olefins characterized by the presence in their structure of the group —$R^1$—C=$CH_2$, where R' is H or a hydrocarbon group. However, polymerizable internal olefin monomers (sometimes referred to in the patent literature as medial olefins) characterized by the presence within their structure of the group:

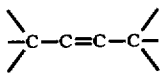

can also be used to form the polyalkenes. When internal olefin monomers are employed, they normally will be employed with terminal olefins to produce polyalkenes which are interpolymers. For purposes of this invention, when a particular polymerized olefin monomer can be classified as both a terminal olefin and an internal olefin, it will be deemed to be a terminal olefin. Thus, pentadiene-1,3 (i.e., piperylene) is deemed to be a terminal olefin for purposes of this invention.

While the polyalkenes generally are hydrocarbon polyalkenes, they can contain substituted hydrocarbon groups such as lower alkoxy, lower alkyl mercapto, hydroxy, mercapto, and carbonyl, provided the non-hydrocarbon moieties do not substantially interfere with the functionalization or derivatization reactions of this invention. When present, such substituted hydrocarbon groups normally will not contribute more than about 10% by weight of the total weight of the polyalkenes. Since the polyalkene can contain such non-hydrocarbon substituent, it is apparent that the olefin monomers from which the polyalkenes are made can also contain such substituents. Normally, however, as a matter of practicality and expense, the olefin monomers and the polyalkenes will be free from non-hydrocarbon groups. (As used herein, the term "lower" when used with a chemical group such as in "lower alkyl" or "lower alkoxy" is intended to describe groups having up to seven carbon atoms.)

Although the polyalkenes may include aromatic groups (especially phenyl groups and lower alkyl- and/or lower alkoxy-substituted phenyl groups such as para-(tert-butyl) phenyl) and cycloaliphatic groups such as would be obtained from polymerizable cyclic olefins or cycloaliphatic substituted-polymerizable acyclic olefins, the polyalkenes usually will be free from such groups. Again, because aromatic and cycloaliphatic groups can be present, the olefin monomers from which the polyalkenes are prepared can contain aromatic and cycloaliphatic groups.

There is a general preference for polyalkenes free from aromatic and cycloaliphatic groups (other than the diene styrene interpolymer exception already noted). Within this general preference, there is a further preference for polyalkenes which are derived from the group consisting of homopolymers and interpolymers of terminal hydrocarbon olefins of 2 to about 16 carbon atoms. This further preference is qualified by the proviso that, while interpolymers of terminal olefins are usually preferred, interpolymers optionally containing up to about 40% of polymer units derived from internal olefins of up to about 16 carbon atoms are also within a preferred group. A more preferred class of polyalkenes are those selected from the group consisting of homopolymers and interpolymers of terminal olefins of 2 to about 6 carbon atoms, more preferably 2 to 4 carbon atoms. However, another preferred class of polyalkenes are the latter, more preferred polyalkenes optionally containing up to about 25% of polymer units derived from internal olefins of up to about 6 carbon atoms.

Specific examples of terminal and internal olefin monomers which can be used to prepare the polyalkenes according to conventional, well-known polymerization techniques include ethylene; propylene; butene-1; butene-2; isobutene; pentene-1; hexene-1; heptene-1; octene-1; nonene-1; decene-1; pentene-2; propylene-tetramer; diisobutylene; isobutylene trimer; butadiene-1,2; butadiene-1,3; pentadiene-1,2; pentadiene-1,3; pentadiene-1,3; isoprene; hexadiene-1,5; 2-chlorobutadiene-1,2; 2-methyl-heptene-1; 3-cyclohexylbutene-1; 2-methyl-5-propyl-hexene-1; pentene-3; octene-4; 3,3-dimethyl-pentene-1; styrene; 2,4-dichlorostyrene; divinylbenzene; vinyl acetate; allyl alcohol; 1-methylvinyl acetate; acrylonitrile; ethyl acrylate; methyl methacrylate; ethyl vinyl ether; and methyl vinyl ketone. Of these, the hydrocarbon polymerizable monomers are preferred and of these hydrocarbon monomers, the terminal olefin monomers are particularly preferred.

Useful polymers include alpha-olefin homopolymers and interpolymers, and ethylene alpha-olefin copolymers and terpolymers. Specific examples of polyalkenes include polypropylenes, polybutenes, ethylene-propylene copolymers, ethylene-butene, propylene-butene copolymers, styrene-isobutene copolymers, isobutene-butadiene-1,3 copolymers, propene-isoprene copolymers, isobutenechloroprene copolymers, isobutene(paramethyl) styrene copolymers, copolymers of hexene-1 with hexadiene-1,3, copolymers of octene-1, copolymers of 3,3-dimethyl-pentene-1 with hexene-1, and terpolymers of isobutene, styrene and piperylene. More specific examples of such interpolymers include copolymer of 95% (by weight) of isobutene with 5% (by weight) of styrene; terpolymer of 98% of isobutene with 1% of piperylene and 1% of chloroprene; terpolymer of 95% of isobutene with 2% of butene-1 and 3% of hexene-1; terpolymer of 60% of isobutene with 20% of pentene-1; and 20% of octene-1; terpolymer of 90% of isobutene with 2% of cyclohexene and 8% of propylene; and copolymer of 80% of ethylene and 20% of propylene. A useful source of polyalkenes are the poly(isobutene)s obtained by polymerization of $C_4$ refinery stream having a butene content of about 35 to about 75% by wt and an isobutene content of about 30 to about 60% by wt in the presence of a Lewis acid catalyst such as aluminum trichloride or boron trifluoride.

Useful ethylene alpha-olefin copolymers include copolymers of ethylene, alpha-olefin and a nonconjugated polyene. Illustrative of such nonconjugated polyenes are aliphatic dienos such as 1,4-hexadiene, 1,5-hexadiene, 1,4-pentadiene, 2-methyl-1,4-pentadiene, 3-methyl-1,4-hexadiene, 4-methyl-1,3-hexadiene, 1,7-octadiene, 1,9-decadiene, exo and endodicyclopentadiene and the like; exo- and endo-alkenylnorbornenes, such as 5-propenyl-, 5-(buten-2-yl)-, and 5-(2-methylbuten-[2']-yl)norbornene and the like; alkylalkenylnorbornenes, such as 5-methylene-, 5-ethylidene-, and 5-isopropylidene-2-norbornene, vinylnorbornene, cyclohexenylnorbornene and the like; alkylnorbornadienes, such as methyl-, ethyl-, and propylnorbornadiene and the like; and cyclodienes such as 1,5-cyclooctadiene, 1,4-cyclooctadiene and the like.

Also useful are high molecular weight poly-n-butenes. Reference is made to commonly assigned copending U.S. Ser. No. 992,871, filed Dec. 17, 1992 (Docket No. PT-915) entitled, "Amorphous Olefin Polymers, Copolymers, Methods of Preparation and Derivatives Thereof"; herein incorporated by reference.

A preferred source of monomer for making poly-n-butenes is petroleum feedstreams such as Raffinate II. These feedstocks are disclosed in the art such as in U.S. Pat. No. 4,952,739, hereby incorporated by reference.

Preparing polyalkenes as described above which meet the various criteria for Mn and Mw/Mn is within the skill of the art and does not comprise part of the present invention. Techniques readily apparent to those skilled in the art include controlling polymerization temperatures, regulating the amount and type of polymerization initiator and/or catalyst, employing chain terminating groups in the polymerization procedure, and the like. Other conventional techniques such as stripping (including vacuum stripping) a very light end and/or oxidatively or mechanically degrading high molecular weight polyalkene to produce lower molecular weight polyalkenes can also be used.

Ethylene Alpha-Olefin Copolymer

Preferred polymers are polymers of ethylene and at least one alpha-olefin having the formula $H_2C=CHR^4$ wherein $R^4$ is straight chain or branched chain alkyl radical comprising 1 to 18 carbon atoms and wherein the polymer contains a high degree of terminal ethenylidene unsaturation. Preferably $R^4$ in the above formula is alkyl of from 1 to 8 carbon atoms and more preferably is alkyl of from 1 to 2 carbon atoms. Therefore, useful comonomers with ethylene in this invention include propylene, 1-butene, hexene-1, octene-1, 4-methylpentene-1, decene-1, dodecene-1, tridecene-1, tetradecene-1, pentadecene-1, hexadecene-1, heptadecene-1, octadecene-1, nonadecene-1 and mixtures thereof (e.g. mixtures of propylene and 1-butene, and the like). Preferred polymers are copolymers of ethylene and propylene and ethylene and butene-1.

The molar ethylene content of the polymers employed is preferably in the range of between about 20 and about 80%, and more preferably between about 30 and about 70%. When butene-1 is employed as comonomer with ethylene, the ethylene content of such copolymer is most preferably between about 20 and about 45 wt %, although higher or lower ethylene contents may be present.

The most preferred ethylene-butene-1 copolymers are disclosed in commonly assigned U.S. Ser. No. 992,192, filed Dec. 17, 1992, titled POLYMERS DERIVED FROM ETHYLENE AND 1-BUTENE FOR USE IN THE PREPARATION OF LUBRICANT DISPERSANT ADDITIVES (Docket No. PT-944).

The preferred method for making low molecular weight ethylene/α-olefin copolymer is described in commonly assigned U.S. Ser. No. 992,690, filed Dec. 17, 1992, titled DILUTE FEED PROCESS FOR THE POLYMERIZATION OF ETHYLENE/α-OLEFIN USING METALLOCENE CATALYST SYSTEMS (Docket No. PT-937). The disclosure of the above two patent applications are herein incorporated by reference.

The ethylene alpha-olefin polymers generally possess a number average molecular weight as recited. Preferred ranges of molecular weights of polymer for use as precursors for dispersants of from about 500 to about 10,000, preferably of from about 1,000 to about 8,000, most preferably of from about 2,500 to about 6,000. The number average molecular weight for such polymers can be determined by several known techniques. A convenient method for such determination is by size exclusion chromatography (also known as gel permeation chromatography (GPC)) which additionally provides molecular weight distribution information, see W. W. Yau, J. J. Kirkland and D. D. Bly, "Modern Size Exclusion Liquid Chromatography", John Wiley and Sons, New York, 1979. Such polymers generally possess an intrinsic viscosity (as measured in tetralin at 135° C.) of between about 0.025 and about 0.6 dl/g, preferably of between about 0.05 and about 0.5 dl/g, most preferably of between about 0.075 and about 0.4 dl/g. These polymers preferably exhibit a degree of crystallinity such that, when grafted, they are essentially amorphous.

The preferred ethylene alpha-olefin polymers are further characterized in that up to about 95% and more of the polymer chains possess terminal vinylidene-type unsaturation. Thus, one end of such polymers will be of the formula $POLY-C(R^e)=CH_2$ wherein $R^e$ is $C_1$ to $C_{18}$ alkyl, preferably $C_1$ to $C_8$ alkyl, and more preferably $C_1$ to $C_2$ alkyl, (e.g., methyl or ethyl) and wherein POLY represents the polymer chain. The chain length of the $R^{11}$ alkyl group will vary depending on the comonomer(s) selected for use in the polymerization. A minor amount of the polymer chains can contain terminal ethenyl unsaturation, i.e. $POLY-CH=CH_2$, and a portion of the polymers can contain internal monounsaturation, e.g. $POLY-CH=CH(R^e)$, wherein $R^e$ is as defined above.

The ethylene alpha-olefin polymer comprises polymer chains, at least about 30% of which possess terminal vinylidene unsaturation. Preferably at least about 50%, more preferably at least about 60%, and most preferably at least about 75% (e.g. 75 to 98%), of such polymer chains exhibit terminal vinylidene unsaturation. The percentage of polymer chains exhibiting terminal vinylidene unsaturation may be determined by FTIR spectroscopic analysis, titration, HNMR, or $C^{13}$NMR.

The ethylene alpha-olefin polymer and the compositions employed in this invention may be prepared as described in U.S. Pat. No. 4,668,834, in European Patent Publications 128,046 and 129,368, and in co-pending Ser. No. 728,111, filed Apr. 29, 1985, and copending Ser. No. 93,460, filed Sep. 10, 1987, the disclosures all of which are hereby incorporated by reference in their entirety.

The polymers can be prepared by polymerizing monomer mixtures comprising ethylene in combination with other monomers such as alpha-olefins having from 20 carbon atoms (and preferably from 3 to 4 carbon atoms, i.e., propylene, butene-1, and mixtures thereof) in the presence of a metallocene catalyst system comprising at least one metallocene (e.g., a cyclopentadienyl-transition metal compound) and an activator, e.g. alumoxane compound. The comonomer content can be controlled through the selection of the metallocene catalyst component and by controlling the partial pressure of the various monomers.

The polymer for use in the present invention can include block and tapered copolymers derived from monomers comprising at least one conjugated diene with at least monovinyl aromatic monomer, preferably styrene. Useful polymers include polymers of the type disclosed in U.S. Pat. Nos. 4,073,737 and 3,795,615, both hereby incorporated by reference.

Such polymers should not be completely hydrogenated so that the polymeric composition contains olefinic double bonds, preferably at least one bond per molecule. Useful polymers include an oil soluble copolymer of the following general formula:

$$(A)_x(B)_y \qquad (4)$$

wherein:

A is a conjugated diene of the formula:

$$CH_2=CH-\underset{\underset{R'}{|}}{C}=CH_2$$

wherein $R'$ is a H or $C_1$ to $C_8$ alkyl group, preferably H or $CH_3$, i.e. isoprene, and present in mole % proportion as indicated by x which may vary from 45 to 99 mole %;

B is a $C_8$ to $C_{20}$ monovinyl aromatic compound and/or aromatic substituted diene and present in weight % proportion as indicated by y which may vary from 1 to 55 mole %; preferably 5 to 40 mole %, and optionally 25 to 30 mole % whereby the most useful composite properties of oxidative stability and $-18°$ C. viscosity of the lubricating oil blend is realized.

The copolymers and block copolymers may be conveniently prepared with known metallic or organometallic catalysts such as lithium metal or sodium metal and organo-lithium or organo-sodium catalysts.

The solution copolymerization may be carried out at any desired temperature in the range from $-50°$ C. to $+150°$ C., and is preferably effected at a temperature between $-20°$ C. and $+80°$ C. The solvents used in polymerization are, in preferred form, hydrocarbon solvents such as pentane, hexane, heptane, cyclohexane, benzene, toluene, xylene and ethyl benzene, with benzene and hexane being the preferred species.

The molecular weight of the copolymers of the mixed conjugated dienes and the monovinyl aromatic monomer may vary between wide limits, as described above depending on intended end use.

The ($\overline{M}n$) is regulated by the ratio of the number of moles of catalyst (e.g., butyllithium) to the number of moles of monomers present during polymerization; the number of units originating from the monomers in a polymer molecule is substantially equal to the ratio of the number of moles of monomer to the number of moles of catalyst (assuming that each catalyst molecule contains one alkali metal atom) present during polymerization, provided that no contaminants which give rise to side reactions with the catalyst (such as oxygen, water, carbon dioxide) are present. If single block copolymers are coupled together, the multiple block copolymers formed have molecular weights which can be calculated from the molecular weight of the single block copolymers (determined as above) and the number thereof which are coupled together.

When the copolymerization has been completed, the block copolymer thus obtained can be partially hydrogenated either immediately or after recovery.

Methods of hydrogenation well known to one skilled in the art are applicable.

Block copolymers as used herein includes "multiple block copolymers" which term denotes copolymers consisting of two or more of the single block copolymers described above, which are bound to each other. A multiple block copolymer may, for example, be prepared by first copolymerizing to completion a mixture of butadiene and isoprene, thereafter polymerizing styrene onto said copolymer and subsequently sequentially copolymerizing a mixture of butadiene and isoprene followed by said styrene onto the "living" block copolymer. For purposes of this disclosure, a "living" copolymer is one which remains stable over an extended period of time during which additional monomers can be added to it.

Multiple block copolymers can also be obtained in other ways such as by coupling of two or more "living" block copolymer molecules. This can be achieved by addition of a compound which reacts with two or more "living" single block copolymer molecules. Examples of this type of compound include compounds containing two or more ester groups, compounds with more than one active halogen atom, e.g., di- and tri-chloromethyl-benzene, phosgene, dichlorosilane, carbon tetrachloride, dimethyldichlorosilane, 1,2-dichloroethane, 1,2-dibromomethane, and the like. Another possible method for preparing multiple block copolymers consists in the preparation of single block copolymer containing a reactive group in the molecule (e.g., a carboxyl group, which is, for example, obtained by bringing the polymerization of a single copolymer to an end by addition of carbon dioxide) and coupling of two or more of the molecules, e.g., by esterifying them with a di- or polyvalent alcohol. Multiple block copolymers have the further advantage that they can be tailored to provide the most useful additive properties while masking one or more undesirable properties inherent in any polymer block.

The present invention can also include star polymers as disclosed in patents such as U.S. Pat. Nos. 5,070,131; 4,108,945 and 3,711,406 as well as U.S. Pat. No. 5,049,294. Particularly useful star polymers are disclosed in U.S. Pat. No. 5,070,131.

Useful star polymers can be produced by the process comprising the following reaction steps:

(a) polymerizing one or more conjugated dienes and, optionally, one or more monoalkenyl arene compounds, in solution, in the presence of an ionic initiator to form a living polymer;

(b) reacting the living polymer with a polyalkenyl coupling agent to form a star-shaped polymer; and (c) partially hydrogenating the star-shaped polymer. The living polymers produced in reaction step (a) are the precursors of the partially hydrogenated polymer chains which extend outwardly from the poly (polyalkenyl coupling agent) nucleus.

Living polymers may be prepared by anionic solution polymerization of congugated dienes and, optionally, monoalkenyl arene compounds in the presence of an alkali metal or an alkali-metal hydrocarbon, e.g. sodium naphthalene, as an ionic initiator. The preferred initiator is lithium or a monolithium hydrocarbon.

The living polymers obtained by reaction step (a), which are linear unsaturated living polymers, are prepared from one or more conjugated dienes, e.g. $C_4$ to $C_{12}$ conjugated dienes and, optionally, one or more monoalkenyl arene compounds.

Examples of suitable conjugated dienes include butadiene (1,3-butadiene); isoprene; 1,3-pentadiene (piperylene); 2,3-dimethyl-1,3-butadiene; 3-butyl-1,3-octadiene; 1-phenyl-1,3-butadiene; 1,3-hexadiene; and 4-ethyl-1,3-hexadiene with butadiene and/or isoprene being preferred. Apart from the one or more conjugated dienes the living polymers may also be partly derived from one or more monoalkenyl arene compounds.

Preferred monoalkenyl arene compounds are the monovinyl aromatic compounds such as styrene, monovinylnaphthalene as well as the alkylated derivatives thereof such as o-, m- and p-methylstyrene, alphamethylstyrene and tertiary-butylstyrene. Styrene is the preferred monoalkenyl arene compound due to its wide availability at a reasonable cost. If a monoalkenyl arene compound is used in the preparation of the living polymers it is preferred that the amount thereof be below about 50% by weight, preferably about 3% to about 50%.

The living polymers may also be partly derived from small amounts of other monomers such as monovinylpyridines, alkyl esters of acrylic and methacrylic acids (e.g. methyl methacrylate, dodecyclmethacrylate, octadecyclmethacrylate), vinyl chloride, vinylidene chloride, monovinyl chloride, vinylidene chloride, monovinyl esters of carboxylic acids (e.g. vinyl acetate and vinyl stearate).

The living polymers may be living homopolymers, living copolymers, living terpolymers, living tetrapolymers, etc. The living homopolymers may be represented by the formula A—M, wherein M is a carbanionic group, e.g. lithium, and A is polybutadiene or polyisoprene. Living polymers of isoprene are the preferred living homopolymers. The living copolymers may be represented by the formula A—B—M, wherein A—B is a block, random or tapered copolymer such as poly(butadiene/isoprene), poly(butadiene/styrene) or poly(isoprene/styrene). Such formulae, without further restriction, do not place a restriction on the arrangement of the monomers within the living polymers. For example, living poly(isoprene/styrene) copolymers may be living polyisoprene-polystyrene block copolymers, living polystyrene-polyisoprene block copolymers, living poly(isoprene/styrene) random copolymers, living poly(isoprene/styrene)tapered copolymers or living poly(isoprene/styrene/isoprene) block copolymers. Living poly(butadiene/styrene/isoprene) terpolymer is an example of a living terpolymer which is acceptable.

The living copolymers may be living block copolymers, living random copolymers or living tapered copolymers. The living block copolymer may be prepared by the stepwise polymerization of the monomers e.g. styrene, to form a living block copolymer having the formula polyisoprene-polystyrene-M, or styrene may be polymerized first to form living polystyrene followed by addition of isoprene to form a living block copolymer having the formula Polystyrene-polyisoprene-M.

In one embodiment, the arms are diblock arms having conjugated diolefin outer blocks and monoalkenyl arene inner blocks. The arms are therefore polymerized by polymerizing blocks of conjugated diolefins, and then polymerizing blocks of monoalkenyl arenes. The arms would then be coupled at the end of the monoalkenyl arene blocks.

Increasing the number of arms employed in star polymers significantly improves both the thickening efficiency and the shear stability of the polymer since it is then possible to prepare additives having a relatively high molecular weight (resulting in increased thickening efficiency) without the necessity of excessively long arms (resulting in an acceptable shear stability).

Star-shaped polymers which are still "living" may then be deactivated or "killed", in known matter, by the addition of a compound which reacts with the carbanionic end group. As examples of suitable deactivators may be mentioned, compounds with one or more active hydrogen atoms such as water, alcohols (e.g. methanol, ethanol isopropanol, 2-ethylhexanol) or carboxylic acids (e.g. acetic acid), compounds with one active halogen atoms, e.g. a chlorine atom (e.g. benzyl chloride, chloromethane), compounds with one ester group and carbon dioxide. If not deactivated in this way, the living star-shaped polymers may be killed by hydrogenation.

Before being killed, the living star-shaped polymers may be reacted with further amounts of monomers such as the same or different dienes and/or monoalkenyl arene compounds of the types discussed above. The effect of this additional step, apart from increasing the number of polymer chains, is to produce a further living star-shaped polymer having at least two different types of polymer chains. For example, a living star-shaped polymer derived from living polyisoprene may be reacted with further isoprene monomer to produce a further living star-shaped polymer having polyisoprene chains of different number average molecular weights. Alternatively, the living star-shaped polyisoprene homopolymer may be reacted with styrene monomer to produce a further living star-shaped copolymer having both polyisoprene and polystyrene homopolymer chains. Thus it can be seen that by different polymer chains is meant chains of different molecular weights and/or chains of different structures.

The star-shaped polymers can be hydrogenated by any suitable technique. Suitably not greater than 80%, of the original olefinic unsaturation is hydrogenated. If the star-shaped polymer is partly derived from a monoalkenyl arene compound, then the amount of aromatic unsaturation which is hydrogenated, if any, will depend on the hydrogenation conditions used. However, preferably less than 10%, more preferably less than 5% of such aromatic unsaturation is hydrogenated.

A preferred hydrogenation process is the selective hydrogenation process shown in U.S. Pat. No. 3,595,942, incorporated herein by reference.

Derivatized Polymers

The Koch or functionalized polymer can be used as a dispersant multifunctional viscosity modifier if the functional group contains the requisite polar group. The functional group can also enable the polymer to participate in a variety of chemical reactions. Derivatives of functionalized polymers can be formed through reaction of the functional group. These derivatized polymers have the requisite properties for a variety of uses including use as dispersants and viscosity modifiers.

A derivatized polymer is one which has been chemically modified to perform one or more functions in a significantly improved way relative to the unfunctionalized polymer and/or the functionalized polymer. Representative of such functions, are dispersancy and/or viscosity modification in lubricating oil compositions.

More specifically, the functionalized polymer can be derivatized by reaction with at least one derivatizing compound to form derivatized polymers. The derivatizing compound typically contains at least one reactive derivatizing group. The reactive derivatizing group is typically selected to render it capable of reacting with the functional groups of the functionalized polymers by the various reactions described below. Representative of such reactions are nucleophilic substitution, transesterification, salt formation, and the like. The derivatizing compound preferably also contains at least one additional group suitable for imparting the desired properties to the derivatized polymer, e.g., polar groups. Thus, such derivatizing compounds typically will contain one or more groups including amine, hydroxy, ester, amide, imide, thio, thioamido, oxazoline, or carboxylate groups or form such groups at the completion of the derivatization reaction.

Thus, the derivatized polymers can include the reaction product of the above recited functionalized polymer with a nucleophilic reactant which include amines, alcohols, amino-alcohols and mixtures thereof to form oil soluble salts, amides, oxazoline, and esters. Alternatively, the functionalized polymer can be reacted with basic metal salts to form metal salts of the polymer. Preferred metals are Ca, Mg, Cu, Zn, Mo, and the like.

Suitable properties sought to be imparted to the derivatized polymer include one or more of dispersancy, multifunctional viscosity modification, antioxidancy, friction modification, antiwear, antirust, seal swell, and the like.

The preferred properties sought to be imparted to the derivatized polymer include dispersancy (both mono- and multifunctional) viscosity modification (e.g. primarily viscosity modification with attendant secondary dispersant properties). A multifunctional dispersant typically will function primarily as a dispersant with attendant secondary viscosity modification.

As indicated above, dispersants are made from polymer having dispersant range molecular weights and viscosity modifiers are made from polymer having viscosity modifier range molecular weights which are higher than dispersant range molecular weights.

Multifunctional dispersants rely on polymers having number average molecular weights of greater than about 2,000 to less than about 20,000. In short, the higher the Mn of the polymer within the dispersant range molecular weight, the higher the contribution of the polymer to the high temperature viscosity properties of the formulation containing the dispersant.

Multifunctional viscosity modifiers possess attendant dispersant properties when the polymer from which they are derived is functionalized and derivatized with groups which contribute to dispersancy as described hereinafter in connection with ashless dispersants.

However, while the Koch functionalization and derivatization techniques for preparing multifunctional viscosity modifiers (also referred to herein as multifunctional viscosity index improvers or MFVI) are the same as for ashless dispersants, the functionality of a functionalized polymer intended for derivatization and eventual use as an MFVI will be controlled to be higher than functionalized polymer intended for eventual use as a dispersant. This stems from the difference in Mn of the MFVI polymer backbone vs. the Mn of the dispersant polymer backbone.

Accordingly, it is contemplated that an MFVI will be derived from functionalized polymer composition having typically up to about one and at least about 0.5 functional group F, (i.e. "n" of formula (I)) for each 20,000, preferably for each 30,000, most preferably for each 5,000 Mn molecular weight segment in the backbone polymer. For example, the functionality of a functionalized polymer having an Mn of 30,000 will typically be controlled to have a functionality, F of about 6 (i.e. n=6). Consequently, the stoichiometry of the derivatization reactions is adjusted accordingly in view of the higher functionality relative to the stoichiometrics described below for dispersant derivatization.

Moreover, it will be observed that to achieve the higher functionality for MFVI end use the functionalization technique is also adjusted accordingly. For example, to increase the functionality it may be necessary to incorporate additional sites of unsaturation into the polymer. This can be achieved by incorporation of dienes into the polymer.

Accordingly, while the following discussion relates primarily to derivatization for dispersant end use, the ashless dispersant portion thereof is also applicable to derivatization for MFVI end use subject to the above caveats.

Dispersants

Dispersants maintain oil insolubles, resulting from oxidation during use, in suspension in the fluid thus preventing sludge flocculation and precipitation. Suitable dispersants include, for example, dispersants of the ash-producing (also known as detergent/inhibitors) and ashless type, the latter type being preferred.

The derivatized polymer compositions of the present invention, can be used as ashless dispersants and multifunctional viscosity index improvers in lubricant and fuel compositions. Ashless dispersants and viscosity index improvers are referred to as being ashless despite the fact that, depending on their constitution, the dispersants may, upon combustion, yield a non-volatile material such as boric oxide or phosphorus pentoxide. The compounds useful as ashless dispersants generally are characterized by a "polar" group attached to a relatively high molecular weight hydrocarbon chain supplied by the polymer of the present invention. The "polar" group generally contains one or more of the elements nitrogen, oxygen and phosphorus. The solubilizing chains are generally higher in molecular weight than those employed with the metallic based dispersants, but in some instances they may be quite similar.

Various types of ashless dispersants can be made by derivatizing the polymer of the present invention and are suitable for use in the lubricant compositions.

Reaction products of functionalized polymer of the present invention derivatized with nucleophilic reagents such as amine compounds, organic hydroxy compounds such as polyols and/or basic inorganic materials.

At least one functionalized polymer is mixed with at least one of amine, alcohol, including polyol, aminoalcohol, etc., to form the dispersant additives. One class of particularly preferred dispersants includes those derived from the functionalized polymer of the present invention reacted with (i) hydroxy compound, e.g., a polyhydric alcohol or polyhydroxy-substituted aliphatic primary amine, e.g., pentaerythritol or trismethylolaminomethane (ii) polyoxyalkylene polyamine, e.g. polyoxypropylene diamine, and/or (iii) polyalkylene polyamine, e.g., polyethylene diamine or tetraethylene pentamine referred to herein as TEPA.

Derivatized Polymer From Amine Compounds

Useful amine compounds for derivatizing functionalized polymers comprise at least one amine and can comprise one or more additional amine or other reactive or polar groups. Where the functional group is a carboxylic acid, carboxylic ester or thiol ester, it reacts with the amine to form an amide.

Amine compounds useful as nucleophilic reactants for reaction with the functionalized polymer of the present invention include those disclosed in U.S. Pat. Nos. 3,445, 441, 5,017,299 and 5,102,566, all hereby incorporated by reference. Preferred amine compounds include mono- and (preferably) polyamines, of about 2 to 60, preferably 2 to 40 (e.g. 3 to 20), total carbon atoms of about 1 to 12, preferably 3 to 12, and most preferably 3 to 9 nitrogen atoms in the molecule. These amines may be hydrocarbyl amines or may be hydrocarbyl amines including other groups, e.g., hydroxy groups, alkoxy groups, amide groups, nitriles, imidazoline groups, and the like. Hydroxy amines with 1 to 6 hydroxy groups, preferably 1 to 3 hydroxy groups, are particularly useful. Preferred amines are aliphatic saturated amines, including those of the general formulas:

and

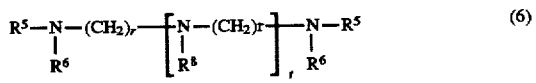

wherein $R^5$, $R^6$, $R^7$ and $R^8$ are independently selected from the group consisting of hydrogen; $C_1$ to $C_{25}$ straight or branched chain alkyl radicals; $C_1$ to $C_{12}$ alkoxy; $C_2$ to $C_6$ alkylene radicals; $C_2$ to $C_{12}$ hydroxy amino alkylene radicals; and $C_1$ to $C_{12}$ alkylamino $C_2$ to $C_6$ alkylene radicals;

and wherein $R^8$ can additionally comprise a moiety of the formula:

 (7)

wherein $R^6$ is as defined above, and wherein r and r' can be the same or a different number of from 2 to 6, preferably 2 to 4; and t and t' can be the same or different and are numbers of from 0 to 10, preferably 2 to 7, and most preferably about 3 to 7. Preferably that the sum of t and t' is not greater than 15. To assure a facile reaction, it is preferred that $R^5$, $R^6$, $R^7$, $R^8$, r, r', t and t' be selected in a manner sufficient to provide the compounds of Formula (5) and (6) with typically at least 1 primary or secondary amine group, preferably at least 2 primary or secondary amine groups. This can be achieved by selecting at least 1 of said $R^5$, $R^6$, $R^7$ and $R^8$ groups to be hydrogen or by letting t in Formula 6 be at least 1 when $R^8$ is H or when the Formula (7) moiety possesses a secondary amino group. The most preferred amine of the above formulas are represented by Formula (6) and contain at least 2 primary amine groups and at least 1, and preferably at least 3, secondary amine groups.

Non-limiting examples of suitable amine compounds include: 1,2-diaminoethane; 1,3-diaminopropane; 1,4-diaminobutane; 1,6-diaminohexane; polyethylene amines such as diethylene triamine; triethylene tetramine; tetraethylene pentamine; polypropylene amines such as 1,2-propylene diamine; di-(1,2-propylene)triamine; di-(1,3-propylene)triamine; N,N-dimethyl-1,3-diaminopropane; N,N-di-(2-aminoethyl) ethylene diamine; N,N-di-(2-hydroxyethyl)-1,3-propylene diamine; 3-dodecyloxypropylamine; N-dodecyl-1,3-propane diamine; tris hydroxymethylaminomethane (THAM); diisopropanol amine; diethanol amine; triethanol amine; mono-, di-, and tri-tallow amines; amino morpholines such as N-(3-aminopropyl)morpholine; and mixtures thereof. Monoamines include methyl ethyl amine, methyl octadecyl amines, anilines, diethylol amine, dipropyl amine, etc.

Other useful amine compounds include: alicyclic diamines such as 1,4-di(aminomethyl)cyclohexane, and heterocyclic nitrogen compounds such as imidazolines, and N-aminoalkyl piperazines of the general formula (8):

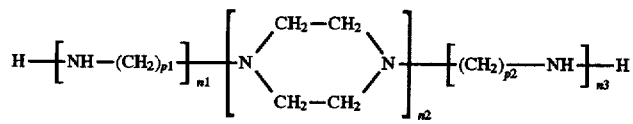 (8)

wherein $P_1$ and $P_2$ are the same or different and are each integers of from 1 to 4, and $n_1$, $n_2$ and $n_3$ are the same or different and are each integers of from 1 to 3. Non-limiting examples of such amines include 2-pentadecyl imidazoline; N-(2-aminoethyl) piperazine; etc.

Commercial mixtures of amine compounds may advantageously be used. For example, one process for preparing alkylene amines involves the reaction of an alkylene dihalide (such as ethylene dichloride or propylene dichloride) with ammonia, which results in a complex mixture of alkylene amines wherein pairs of nitrogens are joined by alkylene groups, forming such compounds as diethylene triamine, triethylenetetramine, tetraethylene pentamine and isomeric piperazines. Low cost poly(ethyleneamine) compounds averaging about 5 to 7 nitrogen atoms per molecule are available commercially under trade names such as "Polyamine H", "Polyamine 400", "Dow Polyamine E-100", etc.

Useful amines also include polyoxyalkylene polyamines such as those of the formula:

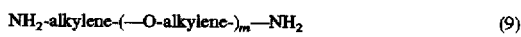 (9)

where m has a value of about 3 to 70 and preferably 10 to 35; and the formula:

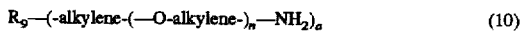 (10)

where n has a value of about 1 to 40 with the provision that the sum of all the n values is from about 3 to about 70 and preferably from about 6 to about 35, and $R^9$ is a polyvalent saturated hydrocarbon radical of up to 10 carbon atoms wherein the number of substituents on the $R^9$ group is represented by the value of "a", which is a number of from 3 to 6. The alkylene groups in either formula (9) or (10) may be straight or branched chains containing about 2 to 7, and preferably about 2 to 4 carbon atoms.

The polyoxyalkylene polyamines of formulas (9) or (10) above, preferably polyoxyalkylene diamines and polyoxyalkylene triamines, may have average molecular weights ranging from about 200 to about 4,000 and preferably from about 400 to about 2,000. The preferred polyoxyalkylene polyamines include the polyoxyethylene and polyoxypropylene diamines and the polyoxypropylene triamines having average molecular weights ranging from about 200 to 2,000. The polyoxyalkylene polyamines are commercially available and may be obtained, for example, from the Jefferson Chemical Company, Inc. under the trade name "Jeffamines D-230, D-400, D-1000, D-2000, T-403, etc.

A particularly useful class of amines are the polyamido and related amines disclosed in U.S. Pat. Nos. 4,857,217; 4,963,275 and 4,956,107, the disclosures of which are herein incorporated by reference, which comprise reaction products of a polyamine and an alpha, beta unsaturated compound of the formula:

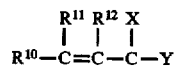

wherein X is sulfur or oxygen, Y is $-OR^{13}$, $SR^{13}$, or $-NR^{13}(R^{14})$, and $R^{10}$, $R^{11}$, $R^{12}$, $R^{13}$ and $R^{14}$ are the same or different and are hydrogen or substituted or unsubstituted hydrocarbyl. Any polyamine, whether aliphatic, cycloaliphatic, aromatic, heterocyclic, etc., can be employed provided it is capable of adding across the acrylic double bond and amidifying with, for example, the carbonyl group ($-C(O)-$) of the acrylate-type compound of formula (11), or with the thiocarbonyl group ($-C(S)-$) of the thioacrylate-type compound of formula (11).

When $R^{10}$, $R^{11}$, $R^{12}$, $R^{13}$ or $R^{14}$ in Formula (11) are hydrocarbyl, these groups can comprise alkyl, cycloalkyl, aryl, alkaryl, aralkyl or heterocyclic, which can be substituted with groups which are substantially inert to any component of the reaction mixture under conditions selected for preparation of the amido-amine. Such substituent groups include hydroxy, halide (e.g., Cl, Fl, I, Br), $-SH$ and alkylthio. When one or more of $R^{10}$ through $R^{14}$ are alkyl, such alkyl groups can be straight or branched chain, and will generally contain from 1 to 20, more usually from 1 to 10, and preferably from 1 to 4, carbon atoms. Illustrative of such alkyl groups are methyl, ethyl, propyl, butyl, pentyl, hexyl, heptyl, octyl, nonyl, decyl, dodecyl, tridecyl, hexadecyl, octadecyl and the like. When one or more of $R^{10}$ through $R^{14}$ are aryl, the aryl group will generally contain from 6 to 10 carbon atoms (e.g., phenyl, naphthyl).

For convenience, the following discussion is directed to the preparation and use of amido-amines, although it will be understood that such discussion is also applicable to the thioamido-amines.

The type of amido-amine formed varies with reaction conditions. For example, a more linear amido-amine is formed where substantially equimolar amounts of the unsaturated carboxylate and polyamine are reacted. The presence of excesses of the ethylenically unsaturated reactant of formula (11) tends to yield an amido-amine which is more cross-linked than that obtained where substantially equimolar amounts of reactants are employed. Where, for economic or other reasons, a cross-linked amido-amine using excess amine is desired, generally a molar excess of the ethylenically unsaturated reactant of about at least 10%, such as 10 to 300%, or greater, for example, 25 to 200%, is employed. For more efficient cross-linking an excess of carboxylated material should preferably be used since a cleaner reaction ensues. For example, a molar excess of about 10 to 100% or greater such as 10 to 50%, but preferably an excess of 30 to 50%, of the carboxylated material. Larger excess can be employed if desired.

In summary, without considering other factors, equimolar amounts of reactants tend to produce a more linear amido-amine whereas excess of the formula reactant tends to yield a more cross-linked amido-amine. It should be noted that the higher the polyamine (i.e., in greater the number of amino groups on the molecule) the greater the statistical probability of cross-linking since, for example, a tetraalkylenepentamine, such as tetraethylene pentamine

has more labile hydrogens than ethylene diamine.

These amido-amine adducts so formed are characterized by both amido and amino groups. In their simplest embodiments they may be represented by units of the following idealized formula:

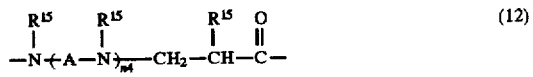

wherein the $R^{15}$'s, which may be the same or different, are hydrogen or a substituent group, such as a hydrocarbon group, for example, alkyl, alkenyl, alkynyl, aryl, etc., and A is a moiety of the polyamine which, for example, may be aryl, cycloalkyl, alkyl, etc., and n4 is an integer such as 1 to 10 or greater. The above simplified formula represents a linear amido-amine polymer. However, cross-linked polymers may also be formed by employing certain conditions since the polymer has labile hydrogens which can further react with either the unsaturated moiety by adding across the double bond or by amidifying with a carboxylate group.

Preferably, however, the amido-amines are not cross-linked to any substantial degree, and more preferably are substantially linear.

Preferably, the polyamine reactant contains at least one primary amine, and more preferably from 2 to 4 primary amines, group per molecule, and the polyamine and the unsaturated reactant of formula (11) are contacted in an amount of from about 1 to 10, more preferably from about 2 to 6, and most preferably from about 3 to 5, equivalents of primary amine in the polyamine reactant per mole of the unsaturated reactant of formula (11).

As an example of the amido-amine adducts, the reaction of tetraethylene pentaamine (TEPA) with methyl methacrylate can be illustrated as follows:

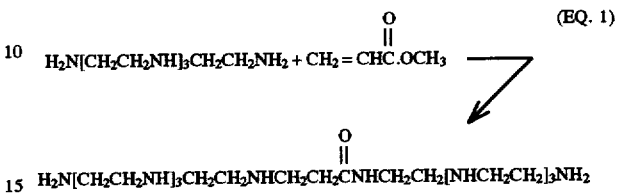

The amine compound can be reacted with the functionalized polymer by heating an oil solution containing 5 to 95 wt. % of functionalized polymer material to about 100° C. to 200° C., preferably 125° C. to 175° C., generally for 1 to 10, e.g. 2 to 6 hours until the desired amount of water is removed. Generally from 0.1 to 1.0, preferably about 0.2 to 0.6, e.g. 0.4 to 0.6, moles of functional groups present in the functionalized polymer is used, per equivalent of nucleophilic reactant, e.g. amine.

Tris(hydroxymethyl) amino methane (TMAM) can be reacted with the aforesaid functionalized polymers to form amides or ester type additives as taught by U.K. 984,409, or to form oxazoline compounds and borated oxazoline compounds as described, for example, in U.S. Pat. Nos. 4,102,798; 4,116,876 and 4,113,639.

Derivatization of Polymer From Alcohols

The functionalized polymers of the present invention can be reacted with alcohols, e.g. to form esters. The alcohols may be aliphatic compounds such as monohydric and polyhydric alcohols or aromatic compounds such as phenols and naphthols.

The aromatic hydroxy compounds from which the esters may be derived are illustrated by the following specific examples: phenol, beta-naphthol, alpha-naphthol, cresol, resorcinol, catechol, p,p'di-hydroxybiphenyl, 2-chlorophenol, 2,4-dibutylphenol, propene tetramer-substituted phenol, didodecylphenol, 4,4'-methylene-bis-phenol, alpha-decyl-beta-naphthol, polyisobutene (molecular weight of 1000)-substituted phenol, the condensation product of heptylphenol with 0.5 mole of formaldehyde, the condensation product of octyl-phenol with acetone, di(hydroxyphenyl)-oxide, di(hydroxyphenyl) sulfide, di(hydroxyphenyl)disulfide, and 4-cyclohexylphenol. Phenol and alkylated phenols having up to three alkyl substituents are preferred.

The alcohols from which the esters may be derived preferably contain up to about 40 aliphatic carbon atoms. They may be monohydric alcohols such as methanols, ethanol, isooctanol, dodecanol, cyclohexanol, cyclopentanol, behenyl alcohol, hexatriacontanol, neopentyl alcohol, isobutyl alcohol, benzyl alcohol, beta-phenyl-ethyl alcohol, 2-methylcyclohexanol, betachloroethanol, monomethyl ether of ethylene glycol, monobutyl ether of ethylene glycol, monopropyl ether of diethylene glycol, monododecyl ether of triethylene glycol, monooleate of ethylene glycol, monostearate of diethylene glycol, secpentyl alcohol, tertbutyl alcohol, 5-bromo-dodecanol, nitro-octadecanol and dioleate of glycerol. The polyhydric alcohols preferably contain from 2 to about 10 hydroxy radicals. They are illustrated by, for example, ethylene glycol, diethylene glycol, triethylene glycol, tetraethylene glycol, dipropylene glycol, tripropylene glycol, dibutylene glycol, tributylene glycol, and other alkylene glycols in which the alkylene radical contains from 2 to about 8 carbon atoms. Other useful polyhydric alcohols include glycerol, monooleate of glycerol, monostearate of glycerol, monomethyl ether of glycerol, pentaerythritol, 9,10-dihydroxy stearic acid, methyl ester of 9,10-dihydroxy stearic acid, 1,2-butanediol, 2,3-hexanediol, 2,4-hexanediol, penacol, erythritol, arabitol, sorbitol, mannitol, 1,2-cyclo-hexanediol, and xylene glycol. Carbohydrates such as sugars, starches, cellulose, etc., likewise may yield the esters of this invention. The carbohydrates may be exemplified by a glucose, fructose, sucrose, rhamnose, mannose, glyceraldehyde, and galactose. Heterocyclic polyols such as described in U.S. Pat. No. 4,797,219, the disclosure of which is herein incorporated by reference may also be employed. Such polyols include tetrahydro-3, 3,5,5-tetrakis(hydroxymethyl)-4-pyranol also known as anhydroennea-heptitol (AEH).

A useful class of polyhydric alcohols are those having at least three hydroxy radicals, some of which have been esterified with a monocarboxylic acid having from about 8 to about 30 carbon atoms, such as octanoic acid, oleic acid, stearic acid, linoleic acid, dodecanoic acid, or tall oil acid. Examples of such partially esterified polyhydric alcohols are the monooleate of sorbitol, distearate of sorbitol, monooleate of glycerol, monostearate of glycerol, di-dodecanoate of erythritol.

The esters may also be derived from unsaturated alcohols such as allyl alcohol, cinnamyl alcohol, propargyl alcohol, 1-cyclohexene-3-ol, an oleyl alcohol. Still another class of the alcohols capable of yielding the esters of this invention comprise the ether-alcohols and amino-alcohols including, for example, the oxyalkylene-, oxyarylene-, aminoalkylene-, and amino-arylene-substituted alcohols having one or more oxyalkylene, amino-alkylene or amino-arylene oxyarylene radicals. They are exemplified by Cellosolve, carbitol, phenoxyethanol, heptylphenyl-(oxypropylene)6-H, octyl-(oxyethylene)30-H, phenyl-(oxyoctylene)2-H, mono (heptylphenyl-oxypropylene)-substituted glycerol, poly (styrene oxide), aminoethanol, 3-amino ethyl-pentanol, di(hydroxyethyl) amine, p-amino-phenol, tri (hydroxypropyl)amine, N-hydroxyethyl ethylene diamine, N,N,N',N'-tetrahydroxy-trimethylene diamine, and the like. For the most part, the ether-alcohols having up to about 150 oxyalkylene radicals in which the alkylene radical contains from 1 to about 8 carbon atoms are preferred.

The esters may be prepared by one of several methods. The method which is preferred because of convenience and superior properties of the esters it produces, involves the reaction of a suitable alcohol or phenol with the acid. The esterification is usually carried out at a temperature above about 100° C., preferably between 150° C. and 300° C.

The water formed as a by-product is removed by distillation as the esterification proceeds. A solvent may be used in the esterification to facilitate mixing and temperature control. It also facilitates the removal of water from the reaction mixture. The useful solvents include xylene, toluene, diphenyl ether, chlorobenzene, and mineral oil.

The relative proportions of the acid functionalized polymer and the hydroxy reactant which are to be used depend to a large measure upon the type of the product desired, the functionality of the functionalized polymer, and the number of hydroxyl groups present in the molecule of the hydroxy reactant.

In some instances, it is advantageous to carry out the esterification in the presence of a catalyst such as sulfuric acid, pyridine hydrochloride, hydrochloric acid, benzenesulfonic acid, p-toluenesulfonic acid, phosphoric acid, or any other known esterification catalyst. The amount of the catalyst in the reaction may be as little as 0.01% (by weight of the reaction mixture), more often from about 0.1% to about 5%.

Ester derivatives likewise may be obtained by the reaction of a acid functionalized polymer with epoxide or a mixture of an epoxide and water. Such reaction is similar to one involving the acid functionalized polymer with a glycol. Epoxides which are commonly available for use in such reaction include, for example, ethylene oxide, propylene oxide, styrene oxide, 1,2-butylene oxide, 2,3-butylene oxide, epichlorohydrin, cyclohexene oxide, 1,2-octylene oxide, epoxidized soya bean oil, methyl ester of 9,10-epoxy-stearic acid, and butadiene monoepoxide. Preferred epoxides are the alkylene oxides in which the alkylene radical has from 2 to about 8 carbon atoms; or the epoxidized fatty acid esters in which the fatty acid radical has up to about 30 carbon atoms and the ester radical is derived from a lower alcohol having up to about 8 carbon atoms.

In lieu of the acid functionalized polymer, a polymer functionalized with lactone acid or an acid halide may be used in the processes illustrated above for preparing the ester derivatives of this invention. Such acid halides may be acid bromides and acid chlorides.

In view of the above, the derivative compositions produced by reacting functionalized polymer with alcohols are esters including both acidic esters and neutral esters. Acidic esters are those in which less than all of the functional groups in functionalized polymer are esterified, and hence possess at least one free functional group. Obviously, acid esters are easily prepared by using an amount of alcohol insufficient to esterify all of the functional groups in the functionalized polymer.

The functionalized polymer of this invention is reacted with the alcohols according to conventional esterification, or transesterification techniques. This normally involves heating the functionalized polymer with the alcohol, optionally in the presence of a normally liquid, substantially inert, organic liquid solvent/diluent and/or in the presence of esterification catalyst. Temperatures of at least about 100° C. up to the decomposition point are used (the decomposition point having been defined hereinbefore). This temperature is usually within the range of about 100° C. up to about 300° C. with temperatures of about 140° C. to 250° C. often being employed.

Many issued patents disclose procedures for reacting high molecular weight carboxylic acids with alcohols to produce acidic esters and neutral esters. These same techniques are applicable to preparing esters from the functionalized polymer of this invention and the alcohols described above. All that is required is that the functionalized polymer of this invention are substituted for the high molecular weight carboxylic acid acylating agents discussed in these patents, usually on an equivalent weight basis. The following U.S. Patents are expressly incorporated herein by reference for their disclosure of suitable methods for reacting the acylating reagents of this invention with the alcohols described above: U.S. Pat. Nos. 3,331,776; 3,381,022; 3,522,179; 3,542,680; 3,697,428 and 3,755,169.

Derivatized Polymer From Reactive Metals/Metal Compounds

Useful reactive metals or reactive metal compounds are those which will form metal salts of the functionalized polymer or metal-containing complexes with the functionalized polymer. Metal complexes are typically achieved by reacting the functionalized polymers with amines and/or alcohols as discussed above and also with complex forming reactants either during or subsequent to amination.

Reactive metal compounds for use in the formation of complexes with the reaction products of functionalized polymer and amines include those disclosed in U.S. Pat. No. 3,306,908. Complex-forming metal reactants include the nitrates, nitrites, halides, carboxylates, phosphates, phosphites, sulfates, sulfites, carbonates, borates, and oxides of cadmium as well as metals having atomic numbers from 24 to 30 (including chromium, manganese, iron, cobalt, nickel, copper and zinc). These metals are the so-called transition or coordination metals, i.e., they are capable of forming complexes by means of their secondary or coordination valence. Specific examples of the complex-forming metal compounds useful as the metal reactant are copper oxide, copper nitrate, cobaltous nitrate, cobaltous oxide, cobaltic oxide, cobalt nitrite, cobaltic phosphate, cobaltous chloride, cobaltic chloride, cobaltous carbonate, chromous acetate, chromic acetate, chromic bromide, chromous chloride, chromic fluoride, chromous oxide, chromium dioxide, chromic oxide, chromic sulfite, chromous sulfate heptahydrate, chromic sulfate, chromic formate, chromic hexanoate, chromium oxychloride, chromic phosphite, manganous acetate, manganous benzoate, manganous carbonate, manganese dichloride, manganese trichloride, manganous citrate, manganous formate, manganous nitrate, manganous oxalate, manganese monooxide, manganese dioxide, manganese trioxide, manganese heptoxide, manganic phosphate, manganous pyrophosphate, manganic metaphosphate, manganous hypophosphite, manganous valerate, ferrous acetate, ferric benzoate, ferrous bromide, ferrous carbonate, ferric formate, ferrous lactate, ferrous nitrate, ferrous oxide, ferric oxide, ferric hypophosphite, ferric sulfate, ferrous sulfite, ferric hydrosulfite, nickel dibromide, nickel dichloride, nickel nitrate, nickel dioleate, nickel stearate, nickel sulfite, cupric propionate, cupric acetate, cupric metaborate, cupric benzoate, cupric formate, cupric laurate, cupric nitrite; cupric oxychloride, cupric palmitate, cupric salicylate, zinc benzoate, zinc borate, zinc bromide, zinc chromate, zinc dichromate, zinc iodide, zinc lactate, zinc nitrate, zinc oxide, zinc stearate, zinc sulfite, cadmium benzoate, cadmium carbonate, cadmium butyrate, cadmium chloroacetate, cadmium fumarate, cadmium nitrate, cadmium dihydrogenphosphate, cadmium sulfite, and cadmium oxide. Hydrates of the above compounds are especially convenient for use in the process of this invention.

U.S. Pat. No. 3,306,908 is expressly incorporated herein by reference for its discussion of reactive metal compounds suitable for forming such complexes and its disclosure of processes for preparing the complexes. Basically, those processes are applicable to the carboxylic derivative compositions of the functionalized polymer of this invention with the amines as described above by substituting, or on an equivalent basis, the functionalized polymer of this invention with the high molecular weight carboxylic acid functionalized polymer disclosed in U.S. Pat. No. 3,306,908.

U.S. Pat. No. Re. 26,433 discloses metals useful in preparing salts from acid functionalized polymer and/or an amine derivatized polymer as described hereinabove. Metal salts are prepared, according to this patent, from alkali metals, alkaline earth metals, zinc, cadmium, lead, cobalt and nickel. Examples of a reactive metal compound suitable for use are sodium oxide, sodium hydroxide, sodium carbonate, sodium methylate, sodium propylate, sodium pentylate, sodium phenoxide, potassium oxide, potassium hydroxide, potassium carbonate, potassium methylate, potassium pentylate, potassium phenoxide, lithium oxide, lithium hydroxide, lithium carbonate, lithium pentylate, calcium oxide, calcium hydroxide, calcium carbonate, calcium methylate, calcium ethylate, calcium propylate, calcium chloride, calcium fluoride, calcium pentylate, calcium phenoxide, calcium nitrate, barium oxide, barium hydroxide, barium carbonate, barium chloride, barium fluoride, barium methylate, barium propylate, barium pentylate, barium nitrate, magnesium oxide, magnesium hydroxide, magnesium carbonate, magnesium ethylate, magnesium propylate, magnesium chloride, magnesium bromide, barium, iodide, magnesium phenoxide, zinc oxide, zinc hydroxide, zinc carbonate, zinc methylate, zinc propylate, zinc pentylate, zinc chloride, zinc fluoride, zinc nitrate trihydrate, cadmium oxide, cadmium hydroxide, cadmium carbonate, cadmium methylate, cadmium propylate, cadmium chloride, cadmium bromide, cadmium fluoride, lead oxide, lead hydroxide, lead carbonate, lead ethylate, lead pentylate, lead chloride, lead fluoride, lead iodide, lead nitrate, nickel oxide, nickel hydroxide, nickel carbonate, nickel chloride, nickel bromide, nickel fluoride, nickel methylate, nickel pentylate, nickel nitrate hexahydrate, cobalt oxide, cobalt hydroxide, cobaltous bromide, cobaltous chloride, cobalt burylate, cobaltous nitrate hexahydrate, etc. The above metal compounds are merely illustrative of those useful in this invention and the invention is not to be considered as limited to such.

U.S. Pat. No. Re. 26,433 is expressly incorporated herein by reference for its disclosure of useful reactive metal compounds as, and processes for, utilizing these compounds in the formation of salts. Again, in applying the teachings of this patent to the present invention, it is only necessary to substitute the functionalized polymer of this invention on an equivalent weight basis for the high molecular weight carboxylic acylating agents disclosed in this reissue patent.

U.S. Pat. No. 3,271,310 is expressly incorporated herein by reference for its disclosure of suitable reactive metal compounds suitable for forming salts of functionalized polymer as well as illustrative processes for preparing salts of these reagents. As will be apparent, the processes of U.S. Pat. No. 3,271,310 are applicable to this invention merely by substituting on an equivalent weight basis, the functionalized polymer of this invention for the high molecular weight carboxylic acids of the patent.

Derivatization Reactant Ratios

From the foregoing description, it is apparent that the appropriate functionalized polymer of this invention can be reacted with any individual derivatizing compound such as amine, alcohol, reactive metal, reactive metal compound or any combination of two or more of any of these; that is, for example, one or more amines, one or more alcohols, one or more reactive metals or reactive metal compounds, or a mixture of any of these. The mixture can be a mixture of two or more amines, a mixture of two or more alcohols, a mixture of two or more metals or reactive metal compounds, or a mixture of two or more components selected from amines and alcohols, from amines and reactive metals or reactive metal compounds, from alcohols and reactive metal compounds, or one or more components from each of the amines, alcohols, and reactive metals or reactive metal compounds. Furthermore, the appropriate functionalized polymer of this invention can be reacted with the amines, alcohols, reactive metals, reactive metal compounds, or mixtures thereof, as described above, simultaneously (concurrently) or sequentially in any order of reaction.

In any of the foregoing derivatizing reactions involving the use of the functionalized polymer of this invention, substantially inert organic liquid diluents may be used to facilitate mixing, temperature control, and handling of the reaction mixture. Suitable diluents include aliphatic, cyctoaliphatic, and aromatic hydrocarbons as well as the corresponding halogenated hydrocarbons, particularly chlorinated hydrocarbons. These diluents are exemplified by benzene, toluene, xylene, chlorobenzenes, hexane, heptane, cyclohexane, or mixtures of these. Mineral oils particularly low viscosity mineral oils are very good diluents. Other organic solvents can also be employed such as ethers, sulfoxide, sulfones, and the like. Where one or more of the reactants themselves are liquid at the reaction temperature, the reactant itself functions as a diluent and it may be convenient sometimes to employ an excess amount of the reactant to serve this purpose.

The following discussion is intended to explain and illustrate what is meant by the term "equivalent" with respect to various classes of reactants as the term is used herein. As will be shown a "derivatization ratio" defined as the molar equivalent ratios of the functionalized polymer to derivatizing compound.

The number of equivalents which characterize the functionalized polymer of the invention depends upon the number of functional groups present within the structure thereof as expressed by its functionality (F or N of Formula I).

Thus, a functionalized polymer having a functionality of 3 has an average of three equivalents per mole. Alternatively, 6,000 Mn polymer functionalized with acid to a functionality of 3 possesses an equivalent weight of 2000 per mole.

A nitrogen-containing derivatizing compound such as an amine reactant, is regarded as having a number of equivalents per mole corresponding to the average number of reactive amine groups, i.e., primary or secondary amine groups, per molecule. Thus, ammonia has one equivalent per mole; urea, hydrazine, ethylenediamine, and piperazine have two equivalents per mole; and tetraethylene pentamine has five equivalents per mole. Mixtures of nitrogen-containing reactants such as mixtures of alkylene polyamines are regarded as having an equivalent weight equal to the weight of the mixture divided by the number of reactive nitrogen atoms present. For example, 1,000 parts of a polyethylene polyamine mixture containing 37 percent by weight nitrogen has an equivalent weight of about 38.

In like manner, hydroxyaromatic compounds and alcohols have equivalent weights equal to their molecular weights divided by the number of functional —OH groups per molecule. Or, from another viewpoint, they possess a number of equivalents per mole equal to the number of —OH groups. Thus, pentaerythritol has four equivalents per mole and an equivalent weight of 34. Phenol has one equivalent per mole so that its equivalent weight equals its molecular weight.

Metal reactants have an equivalent weight equal to their molecular weight divided by the product of the number of metal atoms per molecule of reactant times the valence of the metal. Since most of the metal reactants have only one metal per atom per molecule, the equivalent weight of the metal reactant is normally the molecular weight divided by the valence of the metal. Stated differently, a metal reactant normally has a number of equivalents per mole equal to the valence of the metal. For example, calcium hydroxide, zinc chloride, and barium oxide have two equivalents per mole; sodium hydroxide and lithium hydroxide have one equivalent per mole.

From what has been said hereinabove, it will be apparent to those skilled in the art that the reaction products produced by reacting functionalized polymer of this invention with derivatizing compounds such as alcohols, nitrogen-containing reactants, metal reactants, and the like will, in fact, be mixtures of various reaction products. This is especially apparent in view of the fact that the functionalized polymers themselves can be mixtures of materials. For example, if acid functionalized polymer is reacted with a polyol, the esterification product can contain esters wherein only one hydroxyl group has been esterified, esters wherein two or more of the hydroxy groups have been esterified by the same or different functionalized polymer, esters where all of the carboxyl groups of an acid functionalized polymer have been esterified, esters where less than all of the carboxyl groups of functionalized polymer have been esterified, and the like. However, for purposes of the present invention it is not necessary to know the specific structure of each derivatized component of the reaction mixtures produced, since it is not necessary to isolate these components in order to use them as additives, e.g., in lubricants and fuels.

While the functionalized polymers themselves possess some dispersant characteristics and can be used dispersant additives in lubricants and fuels, best results are achieved when at least about 30, preferably, at least about 50, most preferably 100% of the functional groups are derivatized. Furthermore, it is not necessary that all the functional groups of the functionalized polymer be derivatized to the same product or even the same type of product. Thus, functionalized polymer may be first reacted with one or more alcohols to convert a portion of acid functional groups to ester groups and thereafter this ester product can be reacted with one or more amines and/or one or more metal reactants to convert all or a portion of the remaining carboxyl functions to a derivatized amine groups such as amides, imides, amidines, amine salt groups, and the like or metal salt groups.

In view of the above, the "derivatization ratio" can vary considerably, depending, e.g., on the reactants and type of bonds sought to be formed. Thus, while any derivatization ratio effective to impart the desired properties to the derivatized polymer can be employed, it is contemplated that such effective ratios will range typically from about 0.05:1 to about 4:1, preferably 0.5:1 to about 2.0:1 (e.g. 0.6.1 to about 1.5:1) and most preferably 0.7:1 to about 1:1 (e.g. 0.8:1 to 0.9:1). As can be seen from the above ratios it is preferred to employ an excess of derivatizing compound from an equivalents standpoint, particularly where the unreacted excess thereof can be easily stripped from the reaction mixture.

Post Treatment

Another aspect of this invention involves the post treatment of derivatized polymer. The processes for post-treating derivatized polymer are analogous to the post-treating processes used with respect to conventional dispersants and MFVI's of the prior art. Accordingly, the same reaction conditions, ratio of reactants and the like can be used. Reference is made to U.S. Pat. No. 5,017,199.

Accordingly, derivatized polymer can be post-treated with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos. 3,036,003; 3,200,107; 3,254,025; 3,278,550; 3,281,428; 3,282,955; 3,366,569; 3,373,111; 3,442,808; 3,455,832; 3,493,520; 3,513,093; 3,539,633; 3,579,450; 3,600,372; 3,639,242; 3,649,659; 3,703,536 and 3,708,522 which are herein incorporated by reference.

The amine derivatized polymers of the present invention as described above can be post-treated, particularly for use as dispersants and viscosity index improvers by contacting said polymers with one or more post-treating reagents selected from the group consisting of boron oxide, boron oxide hydrate, boron halides, boron acids, esters of boron acids, carbon disulfide, sulfur, sulfur chlorides, alkenyl cyanides, aldehydes, ketones, urea, thiourea, guanidine, dicyanodiamide, hydrocarbyl phosphates, hydrocarbyl phosphites, hydrocarbyl thiophosphate, hydrocarbyl thiophosphites, phosphorus sulfides, phosphorus oxides, phosphoric acid, hydrocarbyl thiocyanates, hydrocarbyl isocyanates, hydrocarbyl isothiocyanates, epoxides, episulfides, formaldehyde or formaldehyde-producing compounds plus phenols, and sulfur plus phenols, and $C_1$ to $C_{30}$ hydrocarbyl substituted succinic acids and anhydrides (e.g., succinic anhydride, dodecyl succinic anhydride and the like), fumaric acid, itaconic acid, maleic acid, maleic anhydride, chloromaleic acid, chloromaleic anhydride, acrylic acid, methacrylic acid, crotonic acid, cinnamic acid, and lower alkyl (e.g., $C_1$ to $C_4$ alkyl) acid esters of the foregoing, e.g., methyl maleate, ethyl fumarate, methyl fumarate, and the like.

For example, the amine derivatized polymers can be treated with a boron compound selected from the class consisting of boron oxide, boron halides, boron acids and esters of boron acids in an amount to provide from about 0.1 atomic proportion of boron for each mole of said nitrogen composition to about 20 atomic proportions of boron for each atomic proportion of nitrogen of said nitrogen composition. Borated derivatized polymer useful as dispersants can contain from about 0.05 to 2.0 wt. %, e.g. 0.05 to 0.7 wt. % boron based on the total weight of said borated nitrogen-containing dispersant compound. The boron, which appears to be in the product as dehydrated boric acid polymers (primarily $(HBO_2)_3$), is believed to attach to the derivatized polymer as amine salts, e.g., the metaborate salt of said amine derivatized polymers.

Treating is readily carried out by adding from about 0.05 to 4, e.g. 1 to 3 wt. % (based on the weight of said derivatized polymer) of said boron compound, preferably boric acid which is most usually added as a slurry to said nitrogen compound and heating with stirring at from about 135° C. to 190° C., e.g. 140° C. to 170° C., for from 1 to 5 hours followed by nitrogen stripping at said temperature ranges.

Since post-treating processes involving the use of these post-treating reagents is known insofar as application to high molecular weight nitrogen-containing dispersants of the prior art, further descriptions of these processes herein is unnecessary. In order to apply the prior art processes to the compositions of this invention, all that is necessary is that reaction conditions, ratio of reactants, and the like as described in the prior art, be applied to the novel compositions of this invention. The following U.S. patents are expressly incorporated herein by reference for their disclosure of post-treating processes and post-treating reagents applicable to the compositions of this invention: U.S. Pat. Nos. 3,087,936; 3,200,107; 3,254,025; 3,256,185; 3,278,550; 3,281,428; 3,282,955; 3,284,410; 3,338,832; 3,344,069; 3,366,569; 3,373,111; 3,367,943; 3,403,102; 3,428,561; 3,502,677; 3,513,093; 3,533,945; 3,541,012; 3,639,242; 3,708,522; 3,859,318; 3,865,813; 3,470,098; 3,369,021; 3,184,411; 3,185,645; 3,245,908; 3,245,909; 3,245,910; 3,573,205; 3,692,681; 3,749,695; 3,865,740; 3,954,639; 3,458,530; 3,390,086; 3,367,943; 3,185,704; 3,551,466; 3,415,750; 3,312,619; 3,280,034; 3,718,663; 3,652,616; UK Patent No. 1,085,903; UK Patent No. 1,162 436; U.S. Pat. No. 3,558,743. Particularly preferred for post-treating is the process disclosed in commonly assigned U.S. Ser. No. 992,413, filed Dec. 17, 1992 entitled Improved Low Sediment Process for Forming Borated Dispersant, Docket No. PT-849 which application is now abandoned in favor of U.S. Ser. No. 156,342, a continuation-in-part filed Nov. 22, 1993.

The derivatized polymers of the present invention can also be treated with polymerizable lactones (such as epsilon-caprolactone) to form dispersant adducts having the moiety $—[C(O)(C_2)_z O]_m H$, wherein z is a number of from 4 to 8 (e.g., 5 to 7) and m has an average value of from about 0 to 100 (e.g., 0.2 to 20). The derivatized polymers of this invention, particularly for use as a dispersant, can be post-treated with a $C_5$ to $C_9$ lactone, e.g., epsilon-caprolactone, by heating a mixture of the polymers and lactone in a reaction vessel in the absence of a solvent at a temperature of about 50° C. to about 200° C., more preferably from about 75° C. to about 180° C., and most preferably from about 90° C. to about 160° C., for a sufficient period of time to effect reaction. Optionally, a solvent for the lactone, dispersant material and/or the resulting adduct may be employed to control viscosity and/or the reaction rates.

In one preferred embodiment, the $C_5$ to $C_9$ lactone, e.g., epsilon-caprolactone, is reacted with a nitrogen containing polymer (i.e., dispersant) in a 1:1 mole ratio of lactone to dispersant material. In practice, the ratio of lactone to polymer may vary considerably as a means of controlling the length of the sequence of the lactone units in the adduct. For example, the mole ratio of the lactone to the dispersant material may vary from about 10:1 to about 0.1:1, more preferably from about 5:1 to about 0.2:1, and most preferably from about 2:1 to about 0.4:1. It is preferable to maintain the average degree of polymerization of the lactone monomer below about 00, with a degree of polymerization on the order of from about 0.2 to about 50 being preferred, and from about 0.2 to about 20 being more preferred. For optimum dispersant performance the nitrogen containing polymer as a dispersant, sequences of from about 1 to about 5 lactone units in a row are preferred.

Catalysts useful in the promotion of the lactone-post-treatment reactions are selected from the group consisting of stannous octanoate, stannous hexanoate, tetrabutyl titanate, a variety of organic-based acid catalysts and amine catalysts, as described on page 266, and forward, in a book chapter authored by R. D. Lundberg and E. F. Cox, entitled "Kinetics and Mechanisms of Polymerization: Ring Opening Polymerization", edited by Frisch and Reegen, published by Marcel Dekker in 1969, wherein stannous octanoate is an especially preferred catalyst. The catalyst is added to the reaction mixture at a concentration level of about 50 to about 10,000 parts per weight of catalyst per one million parts of the total reaction mixture.

The reactions of such lactones with dispersant materials containing nitrogen or ester groups is more completely described in U.S. Pat. Nos. 4,906,394; 4,866,141; 4,866,135; 4,866,140; 4,866,142; 4,866,139 and 4,963,275, the disclosure of each of which is hereby incorporated by reference in its entirety.

Lubricating Compositions

The above discussions relate to a variety of materials including the Koch functionalized polymer, the derivatized polymer, and post-treated derivatized polymer.

The Koch functionalized polymer, in addition to acting as intermediates for dispersant and MFVI manufacture, can be used as molding release agents, molding agents, metal working lubricants, point thickeners and the like.

The primary utility for all the above-described material, from functionalized polymer all the way through post-treated derivatized polymer, is as and additive for oleaginous compositions. For ease of discussion the above-mentioned materials are collectively and individually referred to herein as additives when used in the context of an oleaginous composition containing such "additives".

Accordingly, the additives of the present invention may be used by incorporation and dissolution into an oleaginous material such as fuels and lubricating oils. When the additives of this invention are used in normally liquid petroleum fuels such as middle distillates boiling from about 65° C. to 430° C., including kerosene, diesel fuels, home heating fuel oil, jet fuels, etc., a concentration of the additives in the fuel in the range of typically from about 0.001 to about 0.5, and preferably 0.005 to about 0.15 wt. %, based on the total weight of the composition, will usually be employed.

The additives of the present invention find their primary utility in lubricating oil compositions which employ a base oil in which the additives are dissolved or dispersed therein. Such base oils may be natural or synthetic. Base oils suitable for use in preparing the lubricating oil compositions of the present invention include those conventionally employed as crankcase lubricating oils for spark-ignited and compression-ignited internal combustion engines, such as automobile and truck engines, marine and railroad diesel engines, and the like. Advantageous results are also achieved by employing the additive mixtures of the present invention in base oils conventionally employed in and/or adapted for use as power transmitting fluids, universal tractor fluids and hydraulic fluids, heavy duty hydraulic fluids, power steering fluids and the like. Gear lubricants, industrial oils, pump oils and other lubricating oil compositions can also benefit from the incorporation therein of the additives of the present invention.

These lubricating oil formulations conventionally contain several different types of additives that will supply the characteristics that are required in the formulations. Among these types of additives are included viscosity index improvers, antioxidants, corrosion inhibitors, detergents, dispersants, pour point depressants, antiwear agents, friction modifiers, etc.

The additives of the present invention, particularly those adapted for use as dispersants or viscosity modifiers, can be incorporated into a lubricating oil in any convenient way. Thus, they can be added directly to the oil by dispersing or dissolving the same in the oil at the desired level of concentrations of the additive. Such blending into the additional lube oil can occur at room temperature or elevated temperatures. Alternatively, the additives can be blended with a suitable oil-soluble solvent and base oil to form a concentrate, and then blending the concentrate with a lubricating oil basestock to obtain the final formulation. Such dispersant concentrates will typically contain (on an active ingredient (AI) basis) from about 10 to about 80 wt. %, typically about 20 to about 60 wt. %, and preferably from about 40 to about 50 wt. %, additive, and typically from about 40 to 80 wt. %, preferably from about 40 to 60 wt. %, base oil, i.e., hydrocarbon oil based on the concentrate weight. MFVI concentrates typically will contain from about 5 to about 50 wt. % AI.

The lubricating oil basestock for the additive typically is adapted to perform a selected function by the incorporation of additional additives therein to form lubricating oil compositions (i.e., formulations).

Usually these concentrates may be diluted with 3 to 100, e.g., 5 to 40 parts by weight of lubricating oil, per part by weight of the additive package, in forming finished lubricants, e.g. crankcase motor oils. The purpose of concentrates, of course, is to make the handling of the various materials less difficult and awkward as well as to facilitate solution or dispersion in the final blend. Thus, the additives of the present invention and formulations containing them would usually be employed in the form of a 40 to 50 wt. % concentrate, for example, in a lubricating oil fraction.

The additives of the present invention will be generally used in admixture with a lube oil basestock, comprising an oil of lubricating viscosity, including natural and synthetic lubricating oils and mixtures thereof. Useful oils are described in U.S. Pat. Nos. 5,017,299 and 5,084,197.

Natural oils include animal oils and vegetable oils (e.g., castor, lard oil) liquid petroleum oils and hydrorefined, solvent-treated or acid-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils and halosubstituted hydrocarbon oils such as polymerized and interpolymerized olefins (e.g., polybutylenes, polypropylenes, propylene-isobutylene copolymers, chlorinated polybutylenes, etc.) poly(hexenes), poly(1-octenes), poly(1-decenes), etc. and mixtures thereof; alkylbenzenes (e.g., dodecyl-benzenes, tetradecylbenzenes, dinonylbenzenes, di-(2-ethylhexyl)-benzenes, etc.); polyphenyls (e.g., biphenyls, terphenyls, alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methylpoly isopropylene glycol ether having an average molecular weight of 1000, diphenyl ether of polyethylene glycol having a molecular weight of 500 to 1,000, diethyl ether of polypropylene glycol having a molecular weight of 1,000 to 1,500; and mono- and polycarboxylic esters thereof, for example, the acetic acid esters, mixed $C_3$ to $C_8$ fatty acid esters and $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebasic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl)sebacate, di-n-hexyl fumarate, dioctyl sebacate, diisooctyl azelate, diisodecyl azelate, dioctyl phthalate didecyl phthalate, dieicosyl sebacate, the 2-ethylhexyl diester of linoleic acid dimer, and the complex ester formed by reacting 1 mole of sebacic acid with 2 moles of tetraethylene glycol and 2 moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol and tripentaerythritol.

Silicon-based oils such as the polyalkyl-, polyaryl-, polyalkoxy-, or polyaryloxysiloxane oils and silicate oils comprise another useful class of synthetic lubricants; they include tetraethyl silicate, tetraisopropyl silicate, tetra-(2-ethylhexyl)silicate, tetra-(4-methyl-2-ethylhexyl)silicate, tetra-(p-tert-butylphenyl)silicate, hexa-(4-methyl-2-pentoxy)disiloxane, poly(methyl)siloxanes and poly (methylphenyl)siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

Unrefined, refined and rerefined oils can be used in the lubricants of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oil breakdown products.

Additional Formulation Components

As indicated above, the additives of the present invention may be mixed with other types of additives selected to perform at least one desired function. Typical of such formations are detergent/inhibitor, viscosity modification, wear inhibitor, oxidation inhibitor, corrosion inhibitor, friction modifier, foam inhibitor, rust inhibitor, demulsifier, lube oil flow improvers, and seal swell control. Each class of such additional additions is discussed in more detail below.

Detergent/Inhibitor

Metal-containing detergents which can also act as rust inhibitors hence the term "detergent/inhibitor" or simply "DI", include the metal salts of sulphonic acids, alkyl phenols, sulphurized alkyl phenols, alkyl salicylates, naphthenates, and other oil soluble mono- and dicarboxylic acids as well as metal-containing complexes thereof. Usually these metal-containing detergent/inhibitors are used in lubricating oil in amounts of about 0.01 to 10, e.g. 0.1 to 5 wt. %, based on the weight of the total lubricating composition. Marine diesel lubricating oils typically employ such metal-containing rust inhibitors and detergents in amounts of up to about 20 wt. %.

Metal detergent/inhibitors are generally basic (viz, overbased) alkali or alkaline earth metal salts (or mixtures thereof, e.g. mixtures of Ca and Mg salts) of one or more organic sulfonic acid (generally a petroleum sulfonic acid or a synthetically prepared alkaryl sulfonic acid), petroleum naphthenic acids, alkyl benzene sulfonic acids, alkyl phenols, alkylene-bis-phenols, oil soluble fatty acids and the like, such as are described in U.S. Pat. Nos. 2,501,731; 2,616,904; 2,616,905; 2,616,906; 2,616,911; 2,616,924; 2,616,925; 2,617,049; 2,777,874; 3,027,325; 3,256,186; 3,282,835; 3,384,585; 3,373,108; 3,350,308; 3,365,396; 3,342,733; 3,320,162; 3,312,618; 3,318,809 and 3,562,159, the disclosures of which are herein incorporated by reference. Among the petroleum sulfonates, the most useful products are those prepared by the sulfonation of suitable petroleum fractions with subsequent removal of acid sludge and purification. Synthetic alkaryl sulfonic acids are usually prepared from alkylated benzenes such as the Friedel-Crafts reaction product of benzene and a polymer such as tetrapropylene, $C_{18}$ to $C_{24}$ hydrocarbon polymer, etc. Suitable acids may also be obtained by sulfonation of alkylated derivatives of such compounds as diphenylene oxide thianthrene, phenolthioxine, diphenylene sulfide, phenothiazine, diphenyl oxide, diphenyl sulfide, diphenylamine, cyclohexane, decahydro naphthalene and the like.

The terms "basic salt" and "overbased salt" are used to designate metal salts wherein the metal is present in stoichiometrically larger amounts than the acid radical.

As used in this discussion, the term "complex" refers to basic metal salts which contain metal in an amount in excess of that present in a neutral or normal metal salt. The "base number" of a complex is the number of milligrams of KOH to which one gram of the complex is equivalent as measured by titration.

The commonly employed methods for preparing the basic salts involve heating a mineral oil solution of the normal metal salt of the acid with a metal neutralizing agent. The use of a "promoter" in the neutralization step to aid the incorporation of a large excess of metal is known and is preferred for the preparation of such compositions.

Examples of compounds useful as the promoter include phenolic substances such as phenol, naphthol, alkyl phenols, thiophenol, sulfurized alkyl phenols, and condensation products of formaldehyde with a phenolic substance; alcohols such as methanol, 2-propanol, octanol, cellosolve, carbitol, ethylene glycol, stearyl alcohol and cyclohexanol; and amines such as aniline, phenylene diamine, phenothiazine, phenol beta-naphthylamine and dodecylamine.

The alkali and alkaline earth metal compounds which may be used in neutralizing these acids to provide the metal salts include the oxides and hydroxides, alkoxides, carbonates, carboxylate, sulfide, hydrosulfide, nitrate, borates and ethers of magnesium, calcium, and barium. Examples are calcium oxide, calcium hydroxide, magnesium acetate and magnesium borate. As noted, the alkaline earth metal compound is used in excess of that required to complete neutralization of the alkaryl sulfonic acids. Generally, the amount ranges from about 100 to 220%, although it is preferred to use at least 125%, of the stoichiometric amount of metal required for complete neutralization.

Various other preparations of basic alkaline earth metal alkaryl sulfonates are known, such as U.S. Pat. Nos. 3,150,088 and 3,150,089 wherein overbasing is accomplished by hydrolysis of an alkoxide-carbonate complex with the alkaryl sulfonate in a hydrocarbon solvent-diluent oil.

An example of a convenient process for the preparation of the metal-containing complexes employs an oil-soluble sulfonic acid, such as a synthetically prepared didodecylbenzene sulfonic acid, which is mixed with an excess of lime (e.g., 10 equivalents per equivalent of the acid) and a promoter such as methanol, heptylphenol, or mixture thereof, and a solvent such as mineral oil, at 50° C. to 150° C. and the process mass is then carbonated until a homogeneous mass is obtained. Complexes of sulfonic acids, carboxylic acids, and mixtures thereof are obtainable by processes such as are described in U.S. Pat. No. 3,312,618. Another example is the preparation of a magnesium sulfonate normal magnesium salt thereof, an excess of magnesium oxide, water, and preferably also an alcohol such as methanol.

The carboxylic acids useful for preparing sulfonate carboxylate complexes, and carboxylate complexes, i.e., those obtainable from processes such as the above wherein a mixture of sulfonic acid and carboxylic acid or a carboxylic acid alone is used in lieu of the sulfonic acid, are oil-soluble acids and include primarily fatty acids which have at least about 12 aliphatic carbon atoms and not more than about 24 aliphatic carbon atoms. Examples of these acids include: palmitic, stearic, myristic, oleic, linoleic, dodecanoic, behenic, etc. Cyclic carboxylic acids may also be employed. These include aromatic and cycloaliphatic acids. The aromatic acids are those containing a benzenoid structure (i.e., benzene, naphthalene, etc.) and an oil-solubilizing radical or radicals having a total of at least about 15 to 18 carbon atoms, preferably from about 15 to about 200 carbon atoms. Examples of the aromatic acids include: stearyl-benzoic acid, phenyl stearic acid, mono- or polywax-substituted benzoic or naphthoic acids wherein the wax group consists of at least about 18 carbon atoms, cetyl hydroxybenzoic acids, etc. The cycloaliphatic acids contemplated have at least about 12, usually up to about 30 carbon atoms. Examples of such acids are petroleum naphthenic acids, cetyl cyclohexane carboxylic acids, dilauryl decahydro naphthalene carboxylic acids, dioctyl cyclopentane carboxylic acids, etc. The thiocarboxylic acid analogs of the above acids, wherein one or both of the oxygen atoms of the carboxyl group are replaced by sulfur, are also contemplated.

The ratio of the sulfonic acid to the carboxylic acid in mixtures is typically at least 1:1 (on a chemical equivalent basis) and is usually less than 5:1, preferably from 1:1 to 2:1.

Usually, the basic composition obtained according to the above-described method is treated with carbon dioxide until its total base number (TBN) is less than about 50, as determined by ASTM procedure D-2896. In many instances, it is advantageous to form the basic product by adding a Ca or Mg base portionwise and carbonating after the addition of each portion. Products with very high metal ratios (10 or above) can be obtained by this method. As used herein, the term "metal ratio" refers to the ratio of total equivalents of alkaline earth metal in the sulfonate complex to equivalents of sulfonic acid anion therein. For example, a normal sulfonate has a metal ratio of 1.0 and a calcium sulfonate complex containing twice as much calcium as the normal salt has a metal ratio of 2.0. The overbased metal detergent compositions usually have metal ratios of at least about 1.1, for example, from about 1.1 to about 30, with metal ratios of from about 2 to 20 being preferred.

Neutral metal sulfonates are frequently used as rust inhibitors. Polyvalent metal alkyl salicylate, naphthenate and phenate materials are known additives for lubricating oil compositions to improve their high temperature performance and to counteract deposition of carbonaceous matter on pistons (U.S. Pat. No. 2,744,069). They can be methylene bridged or sulfur bridged.

The sulfurized metal phenates represent a preferred class of phenates and can be considered the "metal salt of a phenol sulfide" which thus refers to a metal salt whether neutral or basic. They can be typified by the general formula:

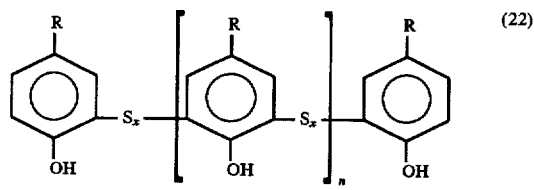

(22)

where x=1 or 2, n=0, 1 or 2; or a polymeric form of such a compound, where R is an alkyl radical, n and x are each integers from 1 to 4, and the average number of carbon atoms in all of the R groups is at least about 9 in order to ensure adequate solubility in oil. The individual R groups may each contain from 5 to 40, preferably 8 to 20, carbon atoms. The metal salt is prepared by reacting an alkyl phenol sulfide with a sufficient quantity of metal containing material to impart the desired alkalinity to the sulfurized metal phenate.

Regardless of the manner in which they are prepared, the sulfurized alkyl phenols which are useful generally contain from about 2 to about 14 wt. %, preferably about 4 to about 12 wt. % sulfur based on the weight of sulfurized alkyl phenol.

The sulfurized alkyl phenol may also be converted by reaction with a metal containing material including oxides, hydroxides and complexes in an amount sufficient to neutralize said phenol and, if desired, to overbase the product to a desired alkalinity by procedures well known in the art. Preferred is a process of neutralization utilizing a solution of metal in a glycol ether.

The neutral or normal sulfurized metal phenates are those in which the ratio of metal to phenol nucleus is about 1:2. The "overbased" or "basic" sulfurized metal phenates are sulfurized metal phenates wherein the ratio of metal to phenol is greater than that of stoichiometric, e.g. basic sulfurized metal dodecyl phenate, has a metal content up to and greater than 100% in excess of the metal present in the corresponding normal sulfurized metal phenates wherein the excess metal is produced in oil-soluble or dispersible form (as by reaction with $CO_2$).

Magnesium and calcium containing detergents although beneficial in other respects can increase the tendency of the lubricating oil to oxidize. This is especially true of the highly basic sulphonates.

The magnesium and/or calcium is generally present as basic or neutral detergents such as the sulphonates and phenates.

Viscosity Modifiers

A viscosity index (V.I.) improver, also referred to as viscosity modifier, is typically employed in multi-grade automobile engine lubricating oils. Viscosity modifiers impart high and low temperature operability to the lubricating oil and permit it to remain relatively viscous at elevated temperatures and also exhibit acceptable viscosity or fluidity at low temperatures. Viscosity modifiers are generally high molecular weight hydrocarbon polymers including polyesters. The viscosity modifiers may include derivatized polymers recited above which include various properties or functions, including dispersancy properties. These oil soluble viscosity modifying polymers will generally have number average molecular weights of from $10^3$ to $10^6$, preferably $10^4$ to $10^6$, e.g., 20,000 to 250,000, as determined by gel permeation chromatography or osmometry.

Examples of suitable hydrocarbon polymers which can be used are viscosity improvers include homopolymers and copolymers of two or more monomers of $C_2$ to $C_{30}$, e.g. $C_2$ to $C_8$ olefins, including both alpha olefins and internal olefins, which may be straight or branched, aliphatic, aromatic, alkyl-aromatic, cycloaliphatic, etc. Frequently they will be of ethylene with $C_3$ to $C_{30}$ olefins, particularly preferred being the copolymers of ethylene and propylene. Other polymers can be used such as polyisobutylenes, homopolymers and copolymers of $C_6$ and higher alpha olefins, atactic polypropylene, hydrogenated polymers and copolymers and terpolymers of styrene, e.g. with isoprene and/or butadiene and hydrogenated derivatives thereof. The polymer may be degraded in molecular weight, for example, by mastication, extrusion, oxidation or thermal degradation, and it may be oxidized and contain oxygen. Also included are derivatized polymers such as post-grafted interpolymers of ethylene-propylene with an active monomer such as maleic anhydride which may be further reacted with an alcohol, or amine, e.g. an alkylene polyamine or hydroxy amine, e.g., see U.S. Pat. Nos. 4,089,794: 4,160,739 and 4,137,185; or copolymers of ethylene and propylene reacted or grafted with nitrogen compounds such as shown in U.S. Pat. Nos. 4,068,056; 4,068,058; 4,146,489 and 4,149,984.

Useful hydrocarbon polymers include ethylene copolymers containing from 15 to 90 wt. % ethylene, preferably 30 to 80 wt. % of ethylene and 10 to 85 wt. %, preferably 20 to 70 wt. % of one or more $C_3$ to $C_{28}$, preferably $C_3$ to $C_{18}$, more preferably $C_3$ to $C_8$, alpha-olefins. While not essential, such copolymers preferably have a degree of crystallinity of less than 25 wt. %, as determined by X-ray and differential scanning calorimetry. Copolymers of ethylene and propylene or ethylene and butene are most preferred. Other alpha-olefins suitable in place of propylene to form the copolymer, or to be used in combination with ethylene and propylene, to form a terpolymer, tetrapolymer, etc., include 1-butene, 1-pentene, 1-hexene, 1-heptene, 1-octene, 1-nonene, 1-decene, etc.; also branched chain alpha-olefins, such as 4-methyl-1-pentene, 4-methyl-1-hexene, 5-methylpentene-1, 4,4-dimethyl-1-pentene, and 6-methylheptene-1, etc., and mixtures thereof.

Terpolymers, tetrapolymer's, etc., of ethylene, said $C_3$ to $C_{28}$ alpha-olefin, and a non-conjugated diolefin or mixtures of such diolefins may also be used. The amount of the non-conjugated diolefin generally ranges from about 0.5 to 20 mole %, preferably from about 1 to about 7 mole %, based on the total amount of ethylene and alpha-olefin present.

The polyester V.I. improvers are generally polymers of esters of ethylenically unsaturated $C_3$ to $C_8$ mono- and dicarboxylic acids such as methacrylic and acrylic acids, maleic acid, maleic anhydride, fumaric acid, etc.

Examples of unsaturated esters that may be used include those of aliphatic saturated mono alcohols of at least 1 carbon atom and preferably of from 12 to 20 carbon atoms, such as decyl acrylate, lauryl acrylate, stearyl acrylate, eicosanyl acrylate, docosanyl acrylate, decyl methacrylate, diamyl fumarate, lauryl methacrylate, cetyl methacrylate, stearyl methacrylate, and the like and mixtures thereof.

Other esters include the vinyl alcohol esters of $C_2$ to $C_{22}$ fatty or mono carboxylic acids, preferably saturated such as vinyl acetate, vinyl laurate, vinyl palmitate, vinyl stearate, vinyl oleate, and the like and mixtures thereof. Copolymers of vinyl alcohol esters with unsaturated acid esters such as the copolymer of vinyl acetate with dialkyl fumarates, can also be used.

The esters may be copolymerized with still other unsaturated monomers such as olefins, e.g. 0.2 to 5 moles of $C_2$ to $C_{20}$ aliphatic or aromatic olefin per mole of unsaturated ester, or per mole of unsaturated acid or anhydride followed by esterification. For example, copolymers or styrene with maleic anhydride esterified with alcohols and amines are known, e.g., see U.S. Pat. No. 3,702,300.

Such ester polymers may be grafted with, or the ester copolymerized with, polymerizable unsaturated nitrogen-containing monomers to impart dispersancy to the V.I. improvers. Examples of suitable unsaturated nitrogen-containing monomers include those containing 4 to 20 carbon atoms such as amino substituted olefins as p-(beta-diethylaminoethyl)styrene; basic nitrogen-containing heterocycles carrying a polymerizable ethylenically unsaturated substituent, e.g. the vinyl pyridines and the vinyl alkyl pyridines such as 2-vinyl-5-ethyl pyridine, 2-methyl-5-vinyl pyridine, 2-vinylpyridine, 4-vinylpyridine, 3-vinyl-pyridine, 3-methyl-5-vinyl-pyridine, 4-methyl-2-vinyl-pyridine, 4-ethyl-2-vinyl-pyridine and 2-butyl-1-5-vinyl-pyridine and the like. N-vinyl lactams are also suitable, e.g. N-vinyl pyrrolidones or N-vinyl piperidones. The vinyl pyrrolidones are preferred and are exemplified by N-vinyl pyrrolidone, N-(1-methylvinyl) pyrrolidone, N-vinyl-5-methyl pyrrolidone, N-vinyl-3, 3-dimethylpyrrolidone, N-vinyl-5-ethyl pyrrolidone, etc.

Such nitrogen- and ester-containing polymeric viscosity index improver dispersants are generally employed in concentrations of from about 0.05 to 10 wt. % in the fully formulated oil, and preferably from about 0.1 to 5 wt. %, and more preferably from about 0.5 to 3 wt. % can reduce (e.g., to about 0.5 wt. %) the amount of the ashless dispersant employed to provide the required dispersancy to the oil formulation.

Antiwear Agents

Antiwear agents, as their name implies, reduce wear of moving metallic parts. Representative of conventional antiwear agents which may be used include, for example, the zinc dialkyl dithiophosphates, and the zinc diaryl dithiophosphates.

Suitable phosphates include dihydrocarbyl dithiophosphates, wherein the hydrocarbyl groups contain an average of at least 3 carbon atoms. Particularly useful are metal salts of at least one dihydrocarbyl dithiophosphoric acid wherein the hydrocarbyl groups contain an average of at least 3 carbon atoms. The acids from which the dihydrocarbyl dithiophosphates can be derived can be illustrated by acids of the formula:

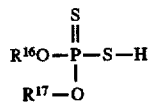

wherein $R^{16}$ and $R^{17}$ are the same or different and are alkyl, cycloalkyl, aralkyl, alkaryl or substituted substantially hydrocarbon radical derivatives of any of the above groups, and wherein the $R^{16}$ and $R^{17}$ groups in the acid each have, on average, at least 3 carbon atoms.

By "substantially hydrocarbon" is meant radicals containing substituent groups (e.g., 1 to 4 substituent groups per radical moiety) such as ether, ester, nitro or halogen which do not materially affect the hydrocarbon character of the radical.

Specific examples of suitable $R^{16}$ and $R^{17}$ radicals include isopropyl, isobutyl, n-butyl, sec-butyl, n-hexyl, heptyl, 2-ethylhexyl, diisobutyl, isooctyl, decyl, dodecyl, tetradecyl, hexadecyl, octadecyl, butylphenyl,o,p-depentylphenyl, octylphenyl, polyisobutene-(molecular weight 350)-substituted phenyl, tetrapropylene-substituted phenyl, beta-octylbutylnaphthyl, cyclopentyl, cyclohexyl, phenyl, chlorophenyl, o-dichlorophenyl, bromophenyl, naphthenyl, 2-methylcyclohexyl, benzyl, chlorobenzyl, chloropentyl, dichlorophenyl, nitrophenyl, dichlorodecyl and xenyl radicals. Alkyl radicals having about 3 to 30 carbon atoms, and aryl radicals having about 6 to 30 carbon atoms, are preferred. Particularly preferred $R^{16}$ and $R^{17}$ radicals are alkyl of 4 to 18 carbons.

The phosphorodithioic acids are readily obtainable by the reaction of phosphorus pentasulfide and an alcohol or phenol. The reaction involves mixing, at a temperature of about 20° C. to 200° C., 4 moles of the alcohol or phenol with one mole of phosphorus pentasulfide. Hydrogen sulfide is liberated as the reaction takes place. Mixtures of alcohols, phenols or both can be employed, e.g., mixtures of $C_3$ to $C_{30}$ alkanols, $C_6$ to $C_{30}$ aromatic alcohols, etc.

The metals useful to make the phosphate salts include Group I metals, Group II metals, aluminum, lead, tin, molybdenum, manganese, cobalt and nickel. Zinc is the preferred metal. Examples of metal compounds which may be reacted with the acid include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin burylate, cobalt oxide, cobalt hydroxide, cobalt carbonate, cobalt pentylate, nickel oxide, nickel hydroxide and nickel carbonate.

In some instances, the incorporation of certain ingredients, particularly carboxylic acids or metal carboxylates such as small amounts of the metal acetate or acetic acid used in conjunction with the metal reactant will facilitate the reaction and result in an improved product. For example, the use of up to about 5% of zinc acetate in combination with the required amount of zinc oxide facilitates the formation of a zinc phosphorodithioate.

The preparation of metal phosphorodithioates is well known in the art and is described in a large number of issued patents, including U.S. Pat. Nos. 3,293,181; 3,397,145; 3,396,109 and 3,442,804, the disclosures of which are hereby incorporated by reference insofar as the preparation of metal salts of organic phosphorodithioic acids useful in this invention are described.

Also useful as antiwear additives are amine derivatives of dithiophosphoric acid compounds, such as are described in U.S. Pat. No. 3,637,499, the disclosure of which is hereby incorporated by reference in its entirety.

The zinc salts are most commonly used as antiwear additives in lubricating oil in amounts of 0.1 to 10, preferably 0.2 to 2 wt. %, based upon the total weight of the lubricating oil composition. They may be prepared in accordance with known techniques by first forming a dithiophosphoric acid, usually by reaction of an alcohol or a phenol with $P_2S_5$ and then neutralizing the dithiophosphoric acid with a suitable zinc compound.

Mixtures of alcohols may be used including mixtures of primary and secondary alcohols, secondary generally for imparting improved antiwear properties, and primary for thermal stability. Mixtures of the two are particularly useful. In general, any basic or neutral zinc compound could be used but the oxides, hydroxides and carbonates are most generally employed. Commercial additives frequently contain an excess of zinc due to use of an excess of the basic zinc compound in the neutralization reaction.

The zinc dihydrocarbyl dithiophosphates are oil soluble salts of dihydrocarbyl esters of dithiophosphoric acids and may be represented by the following formula:

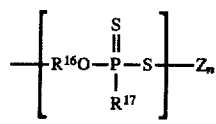

wherein $R^{16}$ and $R^{17}$ are as described in connection with the previous formula.

Suitable antiwear agents also comprise the phosphorous- and sulfur-containing product mixtures described in U.S. application Ser. No. 210,831 filed on Jun. 24, 1988 by Ryer and Gutierrez and the Continuation-in-Part thereof: U.S. Ser. No. 370,315, filed Jun. 22, 1989, the disclosures thereof are incorporated herein by reference.

In a preferred embodiment of the phosphorous- and sulfur-containing product mixtures disclosed in said commonly assigned applications, the following three components, namely: (1) organic phosphite ester, (2) hydrocarbyl thioalkanol, and (3) heterodialkanol are reacted in admixture, preferably in simultaneous admixture.

Preferred hydrocarbyl thioalkanol reactants include $C_8$ to $C_{18}$ thioethanols. The preferred heterodialkanols are thiodialkanols. Representative thiodialkanols include 2,2'-thiodiethanol; 3,3'-thiodipropanol; thio-bis ethoxy-ethanol; thiobisisopropoxyisopropanol; and mixtures thereof.

Oxidation Inhibitors

Oxidation inhibitors reduce the tendency of mineral oils to deteriorate in service, which deterioration can be evidenced by the products of oxidation such as sludge and varnish-like deposits on the metal surfaces and by viscosity growth.

Useful antioxidant materials include oil soluble phenolic compounds, oil soluble sulfurized organic compounds, oil soluble amine antioxidants, oil soluble organo borates, oil soluble organo phosphites, oil soluble organophosphates, oil soluble organo dithiophosphates and mixtures thereof. Preferably such antioxidants are metal-free (that is, free of metals which are capable of generating sulfated ash), and therefore are most preferably ashless (having a sulfated ash value of not greater than 1 wt. % SASH, as determined by ASTMD874).

Illustrative of oil soluble phenolic compounds are alkylated monophenols, alkylated hydroquinones, hydroxylated thiodiphenyl ethers, alkylidenebis phenols, benzyl compounds, acylaminophenols, and esters and amides of hindered phenol-substituted alkanoic acids.

Examples of Phenolic Antioxidants

1. Alkylated monophenols 2,6-di-tert-butyl-4-methylphenol; 2,6-di-tert-butylphenol; 2-tert-butyl-4,6 dimethylphenol; 2,6-di-tertbutyl-4-ethylphenol; 2,6-ditert-butyl-4-ethylphenol; 2,6-di-tert-butyl-4-n-butylphenol; 2,6-di-tertbutyl-4-isobutylphenol; 2,6-dicyclopentyl-4-methylphenol; 2-(alpha-methylcyclohexyl)-4,6-dimethylphenol; 2,6-dioctadecyl-4-methylphenol; 2,4,6-tricyclohexylphenol; 2,6-di-tert-butyl-4-methoxymethylphenol; o-tert-butylphenol.

2. Alkylated hydroquinones 2,6-di-tert-butyl-4-methoxyphenol; 2,5-di-tertbutyl-hydroquinone; 2,5-di-tert-amylhydroquinone; 2,6-di-phenyl-4-octadecyloxyphenol.

3. Hydroxylated thiodiphenyl ethers 2,2'-thiobis(6-tert-butyl-4-methyl-phenol); 2,2'-thiobis(4-octylphenol); 4,4'-thiobis(6-tert-butyl-3-methylphenol); 4,4'-thiobis(6-tert-butyl-2-methylphenol).

4. Alkylidenebisphenols 2,2'-methylenebis(6-tertbutyl-4-methylphenol); 2,2'-methylenebis(6-tert-butyl-4-ethylphenol); 2,2'-methylenebis[4-methyl-6-(alpha-methylcyclohexyl)-phenol]; 2,2'-methylenebis(4-methyl-6- cyclohexylphenol); 2,2'-methylenebis(6-nonyl-4-methylphenol); 2,2'-methylenebis(4,6-di-tert-butylphenol); 2,2'-methylidenebis(4,6-di-tert-butylphenol); 2,2'-ethylidenebis(6-tert-butyl-4-isobutylphenol); 2,2'-methylenebis[6-alpha-methylbenzyl)-4-nonylphenol]; 2,2'-methylenebis[6-(alpha, alpha-dimethylbenzyl)-4-nonylphenol]; 4,4'-methylenebis(2,6-di-tert-butylphenol); 4,4'-methylenebis(6-tert-butyl-2-methylphenol); 1,1-bis-(5-tert-butyl-4-hydroxy-2-methylphenyl)butane; 2,6-di(3-tert-butyl-5-methyl-2-hydroxybenzyl)-4-methylphenol; 1,1,3-tris(5-tert-butyl-4-hydroxy-2-methylphenyl)-3-n-dodecylmercaptobutane; ethylene glycol bis[3,3-bis(3'-tert-butyl-4'-hydroxylphenyl)butyrate]; di(3-tert-butyl-4-hydroxy-5-methylphenyl)dicyclopentadiene; di[2-(3'-tert-butyl-2'-hydroxy-5'-methylbenzyl)-6-tertbutyl-4-methylphenyl]terephthalate.

5. Benzyl compounds 1,3,5-tris(3,5-di-tert-butyl-4-hydroxybenzyl)-2,4,6-trimethyl-benzene; di(3,5-di-tert-butyl-4-hydroxybenzyl)sulfide; 3,5-di-tert-butyl-4-hydroxybenzylmercaptoacetic acid isooctyl ester; bis(4-tert-butyl-3-hydroxy-2,6-dimethyl-benzyl)dithioterephthalate; 1,3,5-tris(3,5-di-tertbutyl-4-hydroxybenzyl)isocyanurate1, 3,5-tris(4-tertbutyl-3-hydroxy-2,6-dimethylbenzyl) isocyanurate; 3,5-di-tert-butyl-4-hydroxybenzylphosphonic acid dioctadecyl ester 3,5-di-tert-butyl-4-hydroxybenzylphosphonic acid mono-ethyl ester calcium salt.

6. Acylaminophenols 4-hydroxylauric acid anilide; 4-hydroxystearic acid anilide; 2,4-bis-octylmercapto-6-(3,5-di-tert-butyl-4-hydroxyaniline)-s-triazine; N-(3,5-di-tert-butyl-4-hydroxyphenyl)carbamic acid octyl ester.

7. Esters of beta-(3,5-di-tert-butyl-4-hydroxyphenyl) propionic acid with mono- or polyhydric alcohols, e.g. with methanol; octadecanol; 1,6-hexanediol; neopentyl glycol; thiodiethylene glycol; diethylene glycol; triethylene glycol; pentaerythritol; tris(hydroxy-ethyl)isocyanurate; and di(hydroxyethyl)oxalic acid diamide.

8. Esters of beta-(5-tert-butyl-4-hydroxy-3-methylphenyl)propionic acid with mono- or polyhydric alcohols, e.g. with methanol; octadecanol; 1,6-hexanediol; neopentyl glycol; thiodiethylene glycol; diethylene glycol; triethylene glycol; pentaerythritol; tris(hydroxyethyl) isocyanurate; and di(hydroxyethyl)oxalic acid diamide.

9. Amides of beta -(3,5-di-tert-butyl-4-hydroxyphenyl) propionic acid, e.g., N,N'-di(3,5-di-tert-butyl-4-hydroxyphenyl-pro-prionyl)hexamethylenediamine; N,N'-di(3,5-di-tert-butyl-4-hydroxyphenylpropionyl) trimethylenediamine; N,N'-di-(3,5-di-tert-butyl-4-hydroxyphenylpropionyl)hydrazine.

Oil soluble sulfurized organic compounds include those represented by the formula:

$$R^{18}S_{x_4}R^{19}$$

wherein S represents sulfur, $x_4$ is a whole number having a value of from 1 to about 10, and $R^{18}$ and $R^{19}$ may be the same or different organic groups. The organic groups may be hydrocarbon groups or substituted hydrocarbon groups containing alkyl, aryl, aralkyl, alkaryl, alkanoate, thiazole, imidazole, phosphorothionate, beta-ketoalkyl groups, etc. The substantially hydrocarbon groups may contain other substituents such as halogen, amino, hydroxyl, mercapto, alkoxy, aryloxy, thio, nitro, sulfonic acid, carboxylic acid, carboxylic acid ester, etc.

Specific examples of types of sulfurized compositions which are useful. Oxidation inhibitors include aromatic, alkyl or alkenyl sulfides and polysulfides, sulfurized olefins, sulfurized carboxylic acid esters, sulfurized ester olefins, sulfurized oil, and mixtures thereof. The preparation of such oil-soluble sulfurized compositions is described in the art, and U.S. Pat. No. 4,612,129 is incorporated herein by reference in its entirety for its disclosure of such preparations; including the type and amount of reactants and catalysts (or promoters), temperatures and other process conditions, and product purification and recovery techniques (e.g., decoloring, filtering, and other solids and impurity removal steps). The sulfurized organic compounds may be aromatic and alkyl sulfides such as dibenzyl sulfide, dixylyl sulfide, dicetylsulfide, diparaffin wax sulfide and polysulfide, cracked wax oleum sulfides, etc.

Examples of dialkenyl sulfides are described in U.S. Pat. No. 2,446,072. Examples of sulfides of this type include 6,6'-dithiobis(5-methyl-4-nonene), 2-butenyl monosulfide and disulfide, and 2-methyl-2-butenyl monosulfide and disulfide.

Representative sulfurized olefins include sulfurized olefins prepared by the reaction of an olefin (preferably containing 3 to 6 carbon atoms) or a lower molecular weight polyolefin derived therefrom, with a sulfur-containing compound such as sulfur, sulfur monochloride and/or sulfur dichloride, hydrogen sulfide, etc. Isobutene, propylene and their dimers, trimers and tetramers, and mixtures thereof are especially preferred olefinic compounds. Of these compounds, isobutylene and diisobutylene are particularly desirable because of their availability and the particularly high sulfur-containing compositions which can be prepared therefrom.

The sulfurized organic compounds may be sulfurized oils which may be prepared by treating natural or synthetic oils including mineral oils, lard oil, carboxylic acid esters derived from aliphatic alcohols and fatty acids or aliphatic carboxylic acids (e.g., myristyl oleate and oleyl oleate) sperm whale oil and synthetic sperm whale oil substitutes and synthetic unsaturated esters or glycerides.

The sulfurized fatty acid esters can be prepared by reacting sulfur, sulfur monochloride, and/or sulfur dichloride with an unsaturated fatty ester at elevated temperatures. Typical esters include $C_1$ to $C_{20}$ alkyl esters of $C_8$ to $C_{24}$ unsaturated fatty acids such as palmitoleic, oleic, ricinoleic, petroselic, vaccenic, linoleic, linolenic, oleostearic, licanic, etc. Sulfurized fatty acid esters prepared from mixed unsaturated fatty acid esters such as are obtained from animal fats and vegetable oils such as tall oil, linseed oil, olive oil, castor oil, peanut oil, rape oil, fish oil, sperm oil, etc. also are useful. Specific examples of the fatty esters which can be sulfurized include lauryl talate, methyl oleate, ethyl oleate, lauryl oleate, cetyl oleate, cetyl linoleate, lauryl ricinoleate, oleolinoleate, oleostearate, and alkyl glycerides.

Another class of organic sulfur-containing compounds includes sulfurized aliphatic esters of an olefinic monodicarboxylic acid. For example, aliphatic alcohols of from 1 to 30 carbon atoms can be used to esterify monocarboxylic acids such as acrylic acid, methacrylic acid, 2,4-pentadienic acid, etc. or fumaric acid, maleic acid, muconic acid, etc. Sulfurization of these esters is conducted with elemental sulfur, sulfur monochloride and/or sulfur dichloride.

Another class of sulfurized organic compounds include diester sulfides. Typical diesters include the butyl, amyl, hexyl, heptyl, octyl, nonyl, decyl, tridecyl, myristyl, pentadecyl, cetyl, heptadecyl, stearyl, lauryl, andeicosyl; diesters of thiodialkanoic acids such as propionic, butanoic, pentanoic and hexanoic acids. Of the diester sulfides, a specific example is dilauryl,3,3'-thiodipropionate.

Other suitable sulfurized organic compound antioxidants include those derived from a particular type of cyclic or bicyclic olefin which is a Diels-Alder adduct of at least one dienophile with at least one aliphatic conjugated diene. The sulfurized Diels-Alder adducts can be prepared by reacting various sulfurizing agents with the Diels-Alder adducts as described more fully below. Typically, the sulfurizing agent is sulfur.

The Diels-Alder adducts are a well-known, art-recognized class of compounds prepared by the diene synthesis of Diels-Alder reaction. A summary of the prior art relating to this class of compounds is found in the Russian monograph, "Dienovyi Sintes", Izdatelstwo Akademii Nauk SSSR, 1963 by A. S. Onischenko. (Translated into the English language by L. Mandel as A. S. Onischenko, "Diene Synthesis", New York, Daniel Davey and Co., Inc., 1964). This monograph and references cited therein are incorporated by reference into the present specification.

Still further sulfurized organic compounds include at least one sulfurized terpene compound or a composition prepared by sulfurizing a mixture comprising at least one terpene and at least one other olefinic compound.

The term "terpene compound" as used in the specification and claims is intended to include the various isomeric terpene hydrocarbons having the empirical formula $C_{10}H_{16}$, such as contained in turpentine, pine oil and dipentenes, and the various synthetic and naturally occurring oxygen-containing derivatives. Mixtures of these various compounds generally will be utilized, especially when natural products such as pine oil and turpentine are used. Pine oil, for example, which is obtained by destructive distillation of waste pinewood with super-heated steam comprises a mixture of terpene derivatives such as alpha-terpineol, beta-terpineol, alpha-fenchol, camphor, borneol/isoborneol, fenchone, estragole, dihydro alpha-terpineol, anethole, and other monoterpene hydrocarbons. The specific ratios and amounts of the various components in a given pine oil will depend upon the particular source and the degree of purification. A group of pine oil-derived products are available commercially from Hercules Incorporated. The pine oil products generally known as terpene alcohols available from Hercules Incorporated are particularly useful in the preparation of this class of sulfurized products. Examples of such products include alpha-Terpineol containing about 95 to 97% of alpha-terpineol, a high purity tertiary terpene alcohol mixture typically containing 96.3% of tertiary alcohols; Terpineol 318 Prime which is a mixture of isomeric terpineols obtained by dehydration of terpene hydrate and contains about 60 to 65 wt. % of alpha-terpineol and 15 to 20% beta-terpineol, and 18 to 20% of other tertiary terpene alcohols. Other mixtures and grades of useful pine oil products also are available from Hercules under such designations as Yarmor 302, Herco pine oil, Yarmor 302W, Yarmor F and Yarmor 60.

The above terpene compounds may be sulfurized terpene compounds, sulfurized mixtures of terpene compounds or mixtures of at least one terpene compound and at least one sulfurized terpene compound. Sulfurized terpene compounds can be prepared by sulfurizing terpene compounds with sulfur, sulfur halides, or mixtures of sulfur dioxide with hydrogen sulfide. Also, the sulfurization of various terpene compounds has been described in the prior art. For example, the sulfurization of pine oil is described in U.S. Pat. No. 2,012,446.

The other olefinic compound which may be combined with the terpene compound and sulfurized may be any of several olefinic compounds such as those described earlier.

The other olefin used in combination with the terpene also may be an unsaturated fatty acid, an unsaturated fatty acid ester, mixtures thereof, mixtures thereof with the olefins described above. The term "fatty acid" as used herein refers to acids which may be obtained by hydrolysis of naturally occurring vegetable or animal fats or oils. These fatty acids usually contain from 16 to 20 carbon atoms and are mixtures of saturated and unsaturated fatty acids. The unsaturated fatty acids generally contained in the naturally occurring vegetable or animal fats and oils may contain one or more double bonds and such acids include palmitoleic acid, oleic acid, linoleic acid, linolenic acid, and erucic acid. The unsaturated fatty acids may comprise mixtures of acids such as those obtained from naturally occurring animal and vegetable oils such as lard oil, tall oil, peanut oil, soybean oil, cottonseed oil, sunflower seed oil, or wheat germ oil. Tall oil is a mixture of rosin acids, mainly abietic acid, and unsaturated fatty acids, mainly oleic and linoleic acids. Tall oil is a by-product of the sulfate process for the manufacture of wood pulp.

The most particularly preferred unsaturated fatty acid esters are the fatty oils, that is, naturally occurring esters of glycerol with the fatty acids described above, and synthetic esters of similar structure. Examples of naturally occurring fats and oils containing unsaturation include animal fats such as Neat's foot oil, lard oil, depot fat, beef tallow, etc. Examples of naturally occurring vegetable oils include cottonseed oil, corn oil, poppyseed oil, safflower oil, sesame oil, soybean oil, sunflower seed oil and wheat germ oil.

The fatty acid esters which are useful also may be prepared from aliphatic olefinic acids of the type described above such as oleic acid, linoleic acid, linolenic acid, and behenic acid by reaction with alcohols and polyols. Examples of aliphatic alcohols which may be reacted with the above-identified acids include monohydric alcohols such as methanol, ethanol, n-propanol, isopropanol, the butanols, etc.; and polyhydric alcohols including ethylene glycol, propylene glycol, trimethylene glycol, neopentyl glycol, glycerol, etc.

The sulfurized derivatives of the other olefin compounds can be prepared by methods known in the art utilizing sulfurizing reagents such as sulfur, sulfur halides or mixtures of sulfur or sulfur dioxide with hydrogen sulfide.

Exemplary of amine antioxidants are phenyl-substituted and phenylene-substituted amines, N-nitro phenylhydroxylamine, isoindoline compounds, phosphin-odithioic acid-vinyl carboxylate adducts, phosphorodithio-ate ester-aldehyde reaction products, phosphorodithioate-alkylene oxide reaction products, silyl esters of terephthalic acid, bis-1,3-alkylamino-2-propanol, anthranilamide compounds, anthranilic acid esters, alpha-methyl styrenated aromatic amines, aromatic amines and substituted benzophenones, aminoguanidines, peroxide-treated phenothiazine, N-substituted phenothiazines and triazines, 3-tertiary alkyl-substituted phenothiazines, alkylated diphenyl-amines, 4-alkylphenyl-1-alkyl-2-naphthylamines, di-benzazepine compounds, fluorinated aromatic amines, alkylated polyhydroxy benzenoid compounds, substituted indans, dimethyl octadecylphosphonate-arylimino di-alkanol copolymers and substituted benzo-diazoborole.

Examples of Amine Antioxidants

N,N'-diisopropyl-p-phenylenediamine; N,N'-di-sec-butyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N,N'-diphenyl-p-phenylenediamine; N,N'-di-(naphthyl-2)-p-phenylenediamine; N-isopropyl-N'-phenyl-p-phenylenediamine; N-(1,3-dimethylbutyl)-N'-phenyl-n-phenylenediamine; N-(1-methylheptyl)-N'- phenyl-p-phenylenediamine; N-cyclohexyl-N'-phenyl-p-phenyl-enediamine; 4-(p-toluenesulfonamido) diphenylamine; N,N'-dimethyl-N,N'-di-sec-butyl-p-phenylenediamine diphenylamine; 4-isopropoxydiphenylamine; N-phenyl-1-naphthylamine; N-phenyl-2-naphthylamine; octylated diphenylamine; 4-n-butylaminophenol; 4-butyrylaminophenol; 4-nonanoylaminophenol; 4-dodecanoylaminophenol; 4-octadecanoylaminophenol; di-(4-methoxyphenyl)amine; di-tert-butyl-4-dimethylaminomethylphenol; 2,4'-diaminodiphenylmethane; 4,4'-diaminophenylmethane; N,N,N',N'-tetramethyl-4,4'-diaminodiphenylmethane; 1,2-di[(2-methylphenyl)amino]ethane; 1,2-di(phenylamino) propane; (o-tolyl)biguanide; di[4-(1',3'-dimethylbutyl) phenyl]amine; tert-octylated N-phenyl-1-napthylamino; and mixture of mono- and dialkylated tert-butyl/tert-octyldiphenylamines.

Oil soluble organo-borate, phosphate and phosphite antioxidants include alkyl- and aryl- (and mixed alkyl, aryl) substituted borates, alkyl- and aryl- (and mixed alkyl, aryl) substituted phosphates, alkyl- and aryl- (and mixed alkyl, aryl) substituted phosphites, and alkyl- and aryl- (and mixed alkyl, aryl) substituted dithiophosphates such as O,O,S-trialkyl dithiophosphates, O,O,S-triaryldithiophosphates and dithiophosphates having mixed substitution by alkyl andaryl groups, phosphorothionyl sulfide, phosphorus-containing silane, polyphenylene sulfide, amine salts of phosphinic acid and quinone phosphates.

A preferred class of antioxidants includes the sulfurized alkyl-substituted hydroxyaromatic compounds. Sulfurized alkyl-substituted hydroxyaromatic compounds and the methods of preparing them are known in the art and are disclosed, for example, in the following U.S. Patents (which are incorporated by reference herein): U.S. Pat. Nos. 2,139,766; 2,198,828; 2,230,542; 2,836,565; 3,285,854; 3,538,166; 3,844,956; 3,951,830 and 4,115,287.

In general, the sulfurized alkyl-substituted hydroxyaromatic compounds may be prepared by reacting an alkyl-substituted hydroxyaromatic compound with a sulfurizing agent such as elemental sulfur, a sulfur halide (e.g., sulfur monochloride or sulfur dichloride), a mixture of hydrogen sulfide and sulfur dioxide, or the like. The preferred sulfurizing agents are sulfur and the sulfur halides, and especially the sulfur chlorides, with sulfur dichloride ($SCl_2$) being especially preferred.

The alkyl-substituted hydroxyaromatic compounds which are sulfurized to produce antioxidant are generally compounds containing at least one hydroxy group (e.g., from 1 to 3 hydroxy groups) and at least one alkyl radical (e.g., from 1 to 3 alkyl radicals) attached to the same aromatic ring. The alkyl radical ordinarily contains about 3 to 100, and preferably about 6 to 20, carbon atoms. The alkyl-substituted hydroxy aromatic compound may contain more than one hydroxy group as exemplified by alkyl resorcinols, hydroquinones and catechols, or it may contain more than one alkyl radical; but normally it contains only one of each. Compounds in which the alkyl and hydroxy groups are ortho, meta and para to each other, and mixtures of such compounds, are within the scope of the invention. Illustrative alkyl-substituted hydroxyaromatic compounds are n-propylphenol, isopropylphenol, n-butylphenol, t-butylphenol, hexylphenol, heptylphenol, octylphenol, nonylphenol, n-dodecylphenol, (propenetetramer)-substituted phenol, octadecylphenol, eicosylphenol, polybutene (molecular weight about 1000)-substituted phenol, n-dodecylresorcinol and 2,4-di-t-butylphenol, and the alkyl-substituted catechols corresponding to the foregoing. Also included are methylene-bridged alkyl-substituted hydroxyaromatic compounds of the type which may be prepared by the reaction of an alkyl-substituted hydroxyaromatic compound with formaldehyde or a formaldehyde-yielding reagent such as trioxane or paraformaldehyde.

The sulfurized alkyl-substituted hydroxy-aromatic compound is typically prepared by reacting the alkyl-substituted hydroxyaromatic compound with the sulfurizing agent at a temperature within the range of about 100° C. to 250° C. The reaction may take place in a substantially inert diluent such as toluene, xylene, petroleum naphtha, mineral oil, Cellosolve or the like. If the sulfurizing agent is a sulfur halide, and especially if no diluent is used, it is frequently preferred to remove acidic materials such as hydrogen halides by vacuum stripping the reaction mixture or blowing it with an inert gas such as nitrogen. If the sulfurizing agent is sulfur, it is frequently advantageous to blow the sulfurized product with an inert gas such as nitrogen or air so as to remove sulfur oxides and the like.

Also useful herein are antioxidants disclosed in the following U.S. Patents, the disclosures of which are herein incorporated by reference in their entirety: U.S. Pat. Nos. 3,451,166; 3,458,495; 3,470,099; 3,511,780; 3,687,848; 3,770,854; 3,850,822; 3,876,733; 3,929,654; 4,115,287; 4,136,041; 4,153,562; 4,367,152 and 4,737,301.

The most preferred antioxidants include oil soluble copper compounds. The copper may be blended into the oil as any suitable oil soluble copper compound. By oil soluble we mean the compound is oil soluble under normal blending conditions in the oil or additive package. The copper compound may be in the cuprous or cupric form. The copper may be in the form of the copper dihydrocarbyl thio- or dithiophosphates wherein copper may be substituted for zinc in the compounds and reactions described above although 1 mole of cuprous or cupric oxide may be reacted with 1 or 2 moles of the dithiophosphoric acid, respectively. Alternatively, the copper may be added as the copper salt of a synthetic or natural carboxylic acid. Examples include $C_{10}$ to $C_{18}$ fatty acids such as stearic or palmitic, but unsaturated acids such as oleic or branched carboxylic acids such as napthenic acids of molecular weight from 200 to 500 or synthetic carboxylic acids are preferred because of the improved handling and solubility properties of the resulting copper carboxylates. Also useful are oil soluble copper dithiocarbamates of the general formula $(RR'NCSS)_nCu$, where n is 1 or 2 and R and R' are the same or different hydrocarbyl radicals containing from 1 to 18 and preferably 2 to 12 carbon atoms and including radicals such as alkyl, alkenyl, aryl, aralkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, amyl, n-hexyl, i-hexyl, n-heptyl, n-octyl, decyl, dodecyl, 2-ethylhexyl, phenyl, butylphenyl, cyclohexyl, octadecyl, methylcyclopentyl, propenyl, butenyl, etc. In order to obtain oil solubility, the total number of carbon atoms (i.e., R and R') will generally be about 5 or greater. Copper sulphonates, phenates, and acetylacetonates may also be used.

Exemplary of useful copper compound antioxidants are copper ($Cu^I$ and/or $Cu^{II}$) salts of alkenyl carboxylic acids or anhydrides such as succinic acids or anhydrides. The salts themselves may be basic, neutral or acidic. They may be formed by reacting (a) any of the functionalized polymers which are useful as dispersants section, which have at least one free carboxylic acid (or anhydride) group with (b) a reactive metal compound. Suitable acid (or anhydride) reactive metal compounds include those such as cupric or cuprous hydroxides, oxides, acetates, borates, and carbonates or basic copper carbonate.

Examples of the metal salts are Cu salts of poly-n-butene succinic anhydride (hereinafter referred to as Cu-PIBSA) polyisobutenyl succinic anhydride (hereinafter referred to as Cu-PIBSA), and Cu salts of poly-n-butene or polyisobutenyl succinic acid. Preferably, the selected metal employed is its divalent form, e.g., Cu+$^2$. The preferred substrates are polyalkenyl carboxylic acids in which the alkenyl group has a molecular weight greater than about 700. The alkenyl group desirably has a $\overline{M}n$ from about 900 to 1,500, and up to 5,000. These materials can be dissolved in a solvent, such as a mineral oil, and heated in the presence of a water solution (or slurry) of the metal bearing material. Heating may take place between 70° C. and about 200° C. Temperatures of 110° C. to 140° C. are entirely adequate. It may be necessary, depending upon the salt produced, not to allow the reaction to remain at a temperature above about 140° C. for an extended period of time, e.g., longer than 5 hours, or decomposition of the salt may occur.

The copper antioxidants (e.g., Cu-PIBSA, Cu-PNB, Cu-oleate, or mixtures thereof) will be generally employed in an amount of from about 50 to 500 ppm by weight of the metal, in the final lubricating or fuel composition.

The copper antioxidants are inexpensive and are effective at low concentrations and therefore do not add substantially to the cost of the product. The results obtained are frequently better than those obtained with previously used antioxidants, which are expensive and used in higher concentrations. In the amounts employed, the copper compounds do not interfere with the performance of other components of the lubricating composition, in many instances, completely satisfactory results are obtained when the copper compound is the sole antioxidant in addition to the ZDDP. The copper compounds can be utilized to replace part or all of the need for supplementary antioxidants. Thus, for particularly severe conditions it may be desirable to include a supplementary, conventional antioxidant. However, the amounts of supplementary antioxidant required are small, far less than the amount required in the absence of the copper compound.

While any effective amount of the copper antioxidant can be incorporated into the lubricating oil composition, it is contemplated that such effective amounts be sufficient to provide said lube oil composition with an amount of the copper antioxidant of from about 5 to 500 (more preferably 10 to 200, still more preferably 10 to 180, and most preferably 20 to 130 (e.g., 90 to 120)) ppm of added copper based on the weight of the lubricating oil composition. Of course, the preferred amount may depend, amongst other factors, on the quality of the basestock lubricating oil.

Corrosion Inhibitors

Corrosion inhibitors, also known as anti-corrosive agents, reduce the degradation of the metallic parts contacted by the lubricating oil composition. Illustrative of corrosion inhibitors are phosphosulfurized hydrocarbons and the products obtained by reaction of a phosphosulfurized hydrocarbon with an alkaline earth metal oxide or hydroxide, preferably in the presence of an alkylated phenol or of an alkylphenol thioester, and also preferably in the presence of carbon dioxide. Phosphosulfurized hydrocarbons are prepared by reacting a suitable hydrocarbon such as a terpene, a heavy petroleum fraction of a $C_2$ to $C_6$ olefin polymer such as polyisobutylene, with from 5 to 30 wt. % of a sulfide of phosphorus for ½ to 15 hours, at a temperature in the range of 65° C. to 315° C. Neutralization of the phosphosulfurized hydrocarbon may be effected in the manner taught in U.S. Pat. No. 2,969,324.

Other suitable corrosion inhibitors include copper corrosion inhibitors comprising hydrocarbyl-thio-distributed derivatives of 1,3,4-thiadiazole, e.g., $C_2$ to $C_{30}$; alkyl, aryl, cycloalkyl, aralkyl and alkaryl-mono-, di-, tri-, tetra- or thio-substituted derivatives thereof.

Representative examples of such materials included 2,5-bis(octylthio)-1,3,4-thiadiazole; 2,5-bis(octyldithio)-1,3,4-thiadiazole; 2,5-bis(octyltrithio)-1,3,4-thiadiazole; 2,5-bis(octyltetrithio)-1,3,4-thiadiazole; 2,5-bis(nonylthio)-1,3,4-thiadiazole; 2,5-bis(dodecyldithio)-1,3,4-thiadiazole; 2-dodecyldithio-5-phenyldithio-1,3,4-thiadiazole; 2,5-bis(cyclohexyldithio)-1,3,4-thiadiazole; and mixtures thereof.

Preferred copper corrosion inhibitors are the derivative of -1,3,4-thiadiazoles such as those described in U.S. Pat. Nos. 2,719,125, 2,719,126 and 3,087,932; especially preferred is the compound 2,5-bis(t-octyldithio)-1,3,4-thiadiazole commercially available as Amoco 150, and 2,5-bis(t-nonyldithio)-1,3,4-thiadiazole, commercially available as Amoco 158.

The preparation of such materials is further described in U.S. Pat. Nos. 2,719,125, 2,719,126, 3,087,932 and 4,410,436, the disclosures of which are hereby incorporated by reference.

Corrosion inhibitors also include copper lead bearing corrosion inhibitors. Typically such compounds are the thiadiazole polysulphides containing from 5 to 50 carbon atoms, their derivatives and polymers thereof. Preferred materials are the derivatives of 1,3,4-thiadiazoles such as those described in U.S. Pat. Nos. 2,719,125; 2,719,126 and 3,087,932; especially preferred is the compound 2,5 bis(t-octadithio)-1,3,4-thiadiazole, commercially available as Amoco 150. Other similar materials also suitable are described in U.S. Pat. Nos. 3,821,236; 3,904,537; 4,097,387; 4,107,059; 4,136,043; 4,188,299 and 4,193,882.

Other suitable corrosion inhibitors are the thio and polythio sulphenamides of thiadiazoles such as those described in U.K. Patent Specification 1,560,830. These compounds can be included in the lubricating composition in an amount from 0.01 to 10, preferably 0.1 to 5.0 wt. % based on the weight of the composition.

Friction Modifiers

Friction modifiers serve to impart the proper friction characteristics to lubricating oil compositions such as automatic transmission fluids. Representative examples of suitable friction modifiers are found in U.S. Pat. No. 3,933,659 which discloses fatty acid esters and amides; U.S. Pat. No. 4,176,074 which describes molybdenum complexes of polyisobutenyl succinic anhydride-amino alkanols; U.S. Pat. No. 4,105,571 which discloses glycerol esters of dimerized fatty acids; U.S. Pat. No. 3,779,928 which discloses alkane phosphonic acid salts; U.S. Pat. No. 3,778,375 which discloses reaction products of a phosphonate with an oleamide; U.S. Pat. No. 3,852,205 which discloses S-carboxy-alkylene hydrocarbyl succinimide, S-carboxy alkylene hydrocarbyl succinamic acid and mixtures thereof; U.S. Pat. No. 3,879,306 which discloses N-(hydroxyalkyl) alkenylsuccinamic acids or succinimides; U.S. Pat. No. 3,932,290 which discloses reaction products of di-(lower alkyl) phosphites and epoxides; and U.S. Pat. No. 4,028,258 which discloses the alkylene oxide adduct of phosphosulfurized N-(hydroxyalkyl) alkenyl succinimides. The disclosures of the above references are herein incorporated by reference. Preferred friction modifiers are include hydroxy amines, as disclosed in U.S. Pat. No. 5,078,893 and the thioether hydroxyamines as disclosed in U.S. Ser. No. 211,428 filed Jun. 24, 1988; glycerol mono and dioleates; succinate esters, or metal salts thereof, of hydrocarbyl substituted succinic acids or anhydrides and thiobis alkanols such as described in U.S. Pat. No. 4,344,853 and amide friction modifiers such as the reaction product of isostearic acid and tetraethylene pentamine as disclosed in commonly assigned U.S. Ser. No. 425,939, filed Oct. 24, 1989 (our file PTF-048), all of which are herein incorporated by reference.

Anti-Foamants

Foam control can be provided by an antifoamant of the polysiloxane type, e.g. silicone oil and polydimethyl siloxane.

Rust Inhibitors

Organic, oil-soluble compounds useful as rust inhibitors comprise nonionic surfactants such as polyoxyalkylene polyols and esters thereof, and anionic surfactants such as salts of alkyl sulfonic acids. Such anti-rust compounds are known and can be made by conventional means. Nonionic surfactants, useful as anti-rust additives in oleaginous compositions usually owe their surfactant properties to a number of weak stabilizing groups such as ether linkages. Nonionic anti-rust agents containing ether linkages can be made by alkoxylating organic substrates containing active hydrogens with an excess of the lower alkylene oxides (such as ethylene and propylene oxides) until the desired number of alkoxy groups have been placed in the molecule.

The preferred rust inhibitors are polyoxyalkylene polyols and derivatives thereof. This class of materials are commercially available from various sources: Pluronic Polyols from Wyandotte Chemicals Corporation; Polyglycol 112-2, a liquid triol derived from ethylene oxide and propylene oxide available from Dow Chemical Co.; and Tergitol, dodecylphenyl or monophenyl polyethylene glycol ethers, and Ucon, polyalkylene glycols and derivatives, both available from Union Carbide Corp. These are but a few of the commercial products suitable as rust inhibitors.

In addition to the polyols per se, the esters thereof obtained by reacting the polyols with various carboxylic acids are also suitable. Acids useful in preparing these esters are lauric acid, stearic acid, succinic acid, and alkyl- or alkenyl-substituted succinic acids wherein the alkyl or alkenyl group contains up to about 20 carbon atoms.

The preferred polyols are prepared as block polymers. Thus, a hydroxy-substituted compound, R—(OH)n (wherein n is 1 to 6, and R is the residue of a mono- or polyhydric alcohol, phenol, naphthol, etc.) is reacted with propylene oxide to form a hydrophobic base. This base is then reacted with ethylene oxide to provide a hydrophylic portion resulting in a molecule having both hydrophobic and hydrophylic portions. The relative sizes of these portions can be adjusted by regulating the ratio of reactants, time of reaction, etc., as is obvious to those skilled in the art. Typically, the ethylene oxide units will comprise from about 10 to about 40%, preferably from about 10 to about 15% by weight of the moleucle. Number average molecular weight of the polyol is from about 2,500 to 4,500. The polyols having a molecule weight of about 4,000 with about 10% attributable to ethylene oxide units are particularly good.

Thus it is within the skill of the art to prepare polyols whose molecules are characterized by hydrophobic and hydrophylic moieties which are present in a ratio rendering rust inhibitors suitable for use in any lubricant composition regardless of differences in the base oils and the presence of other additives.

If more oil-solubility is needed in a given lubricating composition, the hydrophobic portion can be increased and/or the hydrophylic portion decreased. If greater oil-in-water emulsion breaking ability is required, the hydrophylic and/or hydrophobic portions can be adjusted to accomplish this.

Compounds illustrative of R—(OH)n include alkylene polyols such as the alkylene glycols, alkylene triols, alkylene tetrols, etc., such as ethylene glycol, propylene glycol, glycerol, pentaerythritol, sorbitol, mannitol, and the like. Aromatic hydroxy compounds such as alkylated mono- and polyhydric phenols and naphthols can also be used, e.g., heptylphenol, dodecylphenol, etc.

Also useful rust inhibitors are alkoxylated fatty amines, amides, alcohols and the like, including such alkoxylated fatty acid derivatives treated with $C_9$ to $C_{16}$ alkyl-substituted phenols (such as the mono- and di-heptyl, octyl, nonyl, decyl, undecyl, dodecyl and tridecyl phenols), as described in U.S. Pat. No. 3,849,501, which is also hereby incorporated by reference in its entirety.

Demulsifiers

Suitable demulsifiers include the esters disclosed in U.S. Pat. Nos. 3,098,827 and 2,674,619 herein incorporated by reference.

Lube Oil Flow Improvers

Lubricating oil flow improvers (LOFI) include all those additives which modify the size, number, and growth of wax crystals in lube oils or fuels in such a way as to impart improved low temperature handling, pumpability, and/or vehicle operability as measured by such tests as pour point and mini rotary viscometry (MRV). The majority of flow improvers are polymers or contain polymers. These polymers are generally of two types, either backbone or sidechain.

The backbone variety, such as the ethylene-vinyl acetates (EVA), have various lengths of methylene segments randomly distributed in the backbone of the polymer, which associate or cocrystallize with the wax crystals inhibiting further crystal growth due to branches and non-crystallizable segments in the polymer.

The sidechain type polymers, which are the predominant variety used as LOFI's, have methylene segments as the sidechains, preferably as straight side-chains. The polymers work similarly to the backbone type except the sidechains have been found more effective in treating isoparaffins as well as n-paraffins found in lube oils. Representative of this type of polymer are $C_8$ to $C_{18}$ dialkylfumarate/vinyl acetate copolymers, polyacrylates, polymethacrylates, and esterified styrene-maleic anhydride copolymers.

Seal Swell Agents

Seal swellants include mineral oils of the type that provoke swelling of engine seals, including aliphatic alcohols of 8 to 13 carbon atoms such as tridecyl alcohol, with a preferred seal swellant being characterized as an oil-soluble, saturated, aliphatic or aromatic hydrocarbon ester of from 10 to 60 carbon atoms and 2 to 4 linkages, e.g., dihexyl phthalate, as are described in U.S. Pat. No. 3,974,081.

Some of the above numerous additives can provide a multiplicity of effects e.g., a dispersant oxidation inhibitor. This approach is well known and need not be further elaborated herein.

Compositions, when containing these additives, typically are blended into the base oil in amounts which are effective to provide their normal attendant function. Representative effective amounts of such additives are illustrated as follows:

| Compositions | (Broad) Wt % | (Preferred) Wt % |
| --- | --- | --- |
| V.I. Improver | 1–12 | 1–4 |
| Corrosion Inhibitor | 0.01–3 | 0.01–1.5 |
| Oxidation Inhibitor | 0.01–5 | 0.01–1.5 |
| Dispersant | 0.1–10 | 0.1–5 |
| Lube Oil Flow Improver | 0.01–2 | 0.01–1.5 |
| Detergents and Rust | 0.01–6 | 0.01–3 |

| Compositions | (Broad) Wt % | (Preferred) Wt % |
|---|---|---|
| Inhibitors | | |
| Pour Point Depressant | 0.01–1.5 | 0.01–1.5 |
| Anti-Foaming Agents | 0.001–0.1 | 0.001–0.01 |
| Antiwear Agents | 0.001–5 | 0.001–1.5 |
| Seal Swellant | 0.1–8 | 0.1–4 |
| Friction Modifiers | 0.01–3 | 0.01–1.5 |
| Lubricating Base Oil | Balance | Balance |

When other additives are employed, it may be desirable, although not necessary, to prepare additive concentrates comprising concentrated solutions or dispersions of the subject additives of this invention (in concentrate amounts hereinabove described), together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil may be facilitated by solvents and by mixing accompanied with mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of typically from about 2.5 to about 90%, and preferably from about 15 to about 75%, and most preferably from about 25 to about 60% by weight additives in the appropriate proportions with the remainder being base oil.

The final formulations may employ typically about 10 wt. % of the additive-package with the remainder being base oil.

All of said weight percents expressed herein (unless otherwise indicated) are based on active ingredient (AI) content of the additive, and/or upon the total weight of any additive-package, or formulation which will be the sum of the AI weight of each additive plus the weight of total oil or diluent.

The invention is further illustrated by the following examples which are not to be considered as limitative of its scope.

EXAMPLES

The following examples and comparative examples are set forth to illustrate the nature of the invention and the method of carrying it out. However, the invention should not be considered as being limited to the details thereof. Composition parts and percents are by weight unless otherwise indicated. All molecular weights (Mn) are number average molecular weight.

Examples 1–13

Yield of Carboxylic Acid Group (Examples 1–5)

Example 1 (Comparative)

34.5 parts of poly-n-butene polymer (PNB) (Mn=550) dissolved in 36.2 parts of n-heptane ($nC_7$) were charged to an autoclave, mixed and heated to 50° C. 662 parts of $BF_3$ dihydrate ($BF_3.2H_2O$) were then charged followed immediately by CO which brought the total autoclave pressure to 1500 psig. The mixture was stirred for 3 hours at temperature and pressure. Pressure was released, and the reaction product was washed with copious amounts of water and butanol to free the polymer phase from the acid phase. The polymer was dried in an oven. The analysis of the finished polymer showed less than 5% conversion to the carboxylic acid group.

Example 2

The procedure described in Example 1 was then followed except, 37.1 parts of PNB (Mn=550) was dissolved in 40.2 parts of $nC_7$, and 690 parts of $BF_3 \cdot 1.2H_2O$ was substituted for the $BF_3.2H_2O$. The $BF_3.1.2H_2O$ was prepared by bubbling $BF_3$ gas into $BF_3.2H_2O$ until sufficient $BF_3$ was absorbed to give the desired composition. The pressure was brought to 2000 psig with CO. The analysis of the final product showed 85% conversion of the polymer to no-carboxylic acid.

Example 3

The procedure described in Example 1 was followed except that 203.6 parts of ethylene propylene (EP) copolymer (Mn=1800, and about 50 wt. % ethylene) and 159.9 parts of $nC_7$, and 34 parts of $BF_3.1.1 H_2O$ were substituted for the charges of reactants. The pressure was brought to 2000 psi with CO. The conversion to neo-carboxylic acid was 56%.

Example 4

The procedure described in Example 1 was followed except 803 parts of Ethylene Butylene (EB) copolymer (Mn=3700 about 45 wt. % ethylene), 568 parts of iso-octane, and 670 parts of $BF_3.1.1 H_2O$ were used. The pressure was brought to 2000 psig with CO. The reaction product was discharged into an aqueous solution containing 600 parts of sodium fluoride (NaF), 756 parts of water, 302 parts of hexane, and 50 parts of butanol. The polymer product readily separated from the aqueous phase, was recovered, and dried. The analysis showed 85.1% conversion to neo-carboxylic acid.

Example 5

The procedure described in Example 4 was followed except 543 parts of propylene butylene (PB) copolymer (Mn=2800, and about 30 wt. % propylene) 454 parts of iso-octane, and 659 parts of $BF_3.1.1 H_2O$ were used. The reaction product was discharged into 600 parts sodium fluoride, 945 parts water, and 302 parts hexane. The analysis of the final product showed 75.4% conversion to neo-carboxylic acid.

The results of Examples 1–5 are summarized in Table below:

TABLE 1

| Example | Polymer | Mn | Catalyst Complex | Yield (%) |
|---|---|---|---|---|
| Comp. 1 | PNB | 550 | $BF_3.2H_2O$ | <5 |
| 2 | PNB | 550 | $BF_3.1.2H_2O$ | 85 |
| 3 | EP | 1800 | $BF_3.1.1H_2O$ | 56 |
| 4 | EB | 3700 | $BF_3.1.1H_2O$ | 85.1 |
| 5 | PB | 2800 | $BF_3.1.1H_2O$ | 75.4 |

Yield of Alkylester (Examples 6–13)

Example 6 (Comparative)

The procedure described in Example 1 was followed except, 1119.2 parts of PNB (Mn=550) without solvent, and 350 parts of BF$_3$. dibutanol (prepared by bubbling BF$_3$ gas into n-butanol) were used. The pressure was brought to 2000 psig with CO. The analysis of the final product showed less than 5% conversion to neo-alkyl ester.

Example 7

The procedure described in Example 1 was followed except, 153.3 parts of EP polymer (Mn=900, about 50 wt. % ethylene) and 137.9 parts nC$_7$, and 88 parts of BF$_3$• monobutanol was used in the recipe. The polymer was dried, and the conversion to neo-alkyl ester was 86%.

Example 8

The procedure as described in Example 4 was followed except 143 parts of PNB (Mn=550), without solvent, and 37 parts of BF$_3$•monomethanol (prepared by bubbling BF$_3$ gas into methanol) (BF$_3$.CH$_3$OH) was used. The reaction product was discharged into 230 parts of ammonium fluoride and 765 parts methanol. The conversion was 91.3% to the neo-methyl ester.

Yield of Aryl Ester

Example 9

The procedure described in Example 1 was followed except 440 parts of PNB (Mn=550), without solvent, and 244 parts of BF$_3$. tetra (4-chlorophenol) was used. The BF$_3$ complex was prepared by bubbling BF$_3$ gas into melted 4-chlorophenol. The autoclave was pressured to 1485 psig with CO, and the reaction was held at 55° C. for 2 hours. The analysis showed the following results:

| | |
|---|---|
| Yield to 4 chloro phenyl neo-ester/acid | = 60% of polymer |
| to alkyl phenyl ester | = 11.7% of polymer |
| to alkyl phenol | = 10.1% of polymer |
| Total Yield | = 81.8% polymer converted |

Example 10

A complex of BF$_3$ with 4-chlorophenol was prepared by bubbling BF$_3$ into melted 4-chlorophenol. In order to enhance the uptake of BF$_3$ gas to generate BF$_3$.di(4-chlorophenol) the solution was cooled. After several minutes, the solution solidified. Melting the complex resulted in rapid liberation of BF$_3$.

Example 11

An autoclave was charged with 391 psig of BF$_3$ gas at 30° C., followed by an additional 118 psig of CO, to a total pressure of about 500 psig. While stirring the autoclave, a mixture of 440 parts PNB (Mn=550) and 108 parts of 3-fluoro-phenol was charged to the reactor, and the pressure was brought to 1500 psig with CO, and the temperature to 50° C. The reaction was held at these conditions for 2 hours and the autoclave was then depressurized. The reaction product was stripped to remove BF$_3$ gas, and excess substituted phenol. The final product analysis showed 91.5% yield.

Example 12

The procedure of Example 11 was followed, except the autoclave was pressured to 199 psig with BF$_3$ at 50° C., followed by 301 psig of CO, to bring the total pressure to 500 psig and 406 parts of EB copolymer (Mn=4600, 20 wt. % ethylene) and 100.6 parts of 2,4-dichlorophenol (pKa=7.85) at 50° C. were charged to the autoclave and pressured to 1430 psig with CO. The yield was 84.5%.

Example 13

The procedure in Example 11 was followed except the autoclave was pressured to 254 psig with BF$_3$ at 50° C., followed by 254 psig of CO to bring the total pressure to 508 psig; and, 110 parts EB polymer (Mn=2200, about 50% ethylene) 31 parts of dichlorophenol (pKa=7.85) at 50° C. were charged to the autoclave, and pressurized to 2000 psig with CO. The conversion was 85.4%.

The results of Examples 6–9 and 11–13 are summarized in Table 2 below:

TABLE 2

| Example | Polymer | Mn | Catalyst Complex | Yield (%) |
|---|---|---|---|---|
| Comp. 6 | PNB | 550 | BF$_3$.dibutanol | <5 |
| 7 | EP | 900 | BF$_3$.monobutanol | 86 |
| 8 | PNB | 550 | monomethanol | 91.3 |
| 9 | PNB | 550 | BF$_3$.tetra(4-chlorophenol) | 81.8 |
| 11 | PNB | 550 | *BF$_3$ +3-fluorophenol | 91.5 |
| 12 | EB | 4600 | *BF$_3$ 2,4-dichloro- | 84.5 |
| 13 | EB | 2200 | *BF$_3$+dichlorophenol | 85.4 |

*Catalyst and phenolic compound added separately in one step.

Examples 14–18

Amination Reaction of PNB-neo carboxylic with PAM

Example 14

200 parts the PNB neocarboxylic acid prepared by a process similar to that of Example 2 and 31.2 parts of poly(ethyleneamine) averaging 5–8 nitrogens per molecule (PAM) were charged into a reactor with stirring. The reactor contents were purged with nitrogen. The reactor was sealed and the pressure was brought to 60 psig with nitrogen. The reactor was heated to 240° C. for five hours. The contents were then sparged with nitrogen via a dip tube and overhead vent line and cooled at 30° C. The yield of carboxylic acid amide by $^{13}$C-NMR was 45.4%.

Example 15

374 parts of neo acid functionalized EB copolymer of Example 4 dissolved in 700 parts heptane were charged to a reactor vessel. The solution was heated with mixing to 90° C. Then, 70 parts of thionyl chloride was slowly added to the solution, plus an additional 300 parts of heptane. After the reaction to the acid chloride was complete, the solution was heated to 100° C. at atmospheric pressure with N$_2$ sparging followed by high vacuum flashing to remove reaction by products and heptane. The acid chloride product was cooled. Then, fresh, dry heptane was added to the acid chloride product. The acid chloride product was then heated to 90° C. Then, 10 parts of polyamine (PAM) and 17.8 parts of triethylamine were slowly added to the acid chloride. The reaction mixture was filtered and excess triethylamine was stripped to produce the aminated product as shown by infrared analysis.

Example 16

17.8 parts of the 2,4-dichlorophenyl ester of the EB copolymer of Example 12 were charged to a reaction vessel.

The vessel contents were heated to 80° C. with mixing. Then 0.442 parts of polyamine (PAM) was charged to the vessel. The vessel contents were than slowly heated over a period of 8 hours from 150° C. to 220° C. while refluxing the liberated dichlorophenol (pKa=7.85). After complete conversion to the amide, the phenol was removed by $N_2$ sparging. The vessel contents were cooled to ambient temperature. Carbon 13 NMR analysis showed quantitative conversion of ester to amide.

Example 17

The procedure as described in Example 16 was followed, except 20.2 parts of the 2,4-dichlorophenyl ester of Example 13 was used with 0.954 parts of PAM. The carbon[13] NMR analysis showed quantitative conversion of ester to amide.

Example 18

19.4 parts of the aminated polymer described in Example 17 was mixed with 10.0 parts of base oil and heated to 140° C. in a reaction vessel with mixing. Then 1.407 parts of milled 30% boric acid slurry in base oil was slowly added to the vessel contents. The reactor was sparged with $N_2$ at temperature for two hours, then an additional 6.26 parts of base oil was added to the reaction vessel. The vessel contents were cooled to 120° C., and filtered. The analysis of the product showed a 45% active ingredient level (0.73% N, 0.26% B).

What is claimed is:

1. A derivatized polymer composition comprising the reaction product of:

(A) a functionalized polymer of the formula:

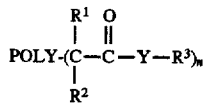  (I)

wherein POLY- is derived from unsaturated polymer, other than gem-structured polyolefin, the unsaturated polymer having a number average molecular weight prior to functionalization of from about 500 to about 20,000, n is a number greater than 0 and represents the functionality of the functionalized polymer, $R^1$ and $R^2$ are the same or different and are selected from the group consisting of hydrogen, hydrocarbyl, and polymeric hydrocarbyl, with the proviso that $R^1$ and $R^2$ are selected such that at least hydrogen, Y is selected from the group consisting of O and S, and $R^3$ is selected from H and hydrocarbyl; and the proviso that $R^1$ and $R^2$ are selected such that at least 50 mole percent of the

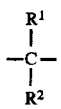

groups have both $R^1$ and $R^2$ not hydrogen,
Y is selected from the group consisting of O and S, and $R^3$ is selected from H and hydrocarbyl; and
(B) a derivatizing compound selected from the group consisting of polyamine, polyol and mixtures thereof.

2. The composition according to claim 1, wherein the unsaturated polymer from which POLY- is derived is selected from the group consisting of ethylene alpha-olefin copolymer, poly(alpha-olefin)homopolymer, and poly(alpha-olefin)copolymer.

3. The composition according to claim 2, wherein the unsaturated polymer comprises ethylene alpha-olefin copolymer of ethylene and at least one alpha-olefin having the formula $H_2C=CHR^4$ wherein $R^4$ is straight chain or branched chain alkyl radical comprising 1 to 18 carbon atoms, and wherein the ethylene alpha-olefin copolymer comprises polymer chains, at least about 30 percent of which possess terminal vinylidene unsaturation.

4. The composition according to claim 3, wherein the ethylene alpha-olefin copolymer has a number average molecular weight of from about 1,000 to about 8,000.

5. The composition according to claim 3, wherein the unsaturated polymer comprises a polymer of ethylene and butane-1.

6. The composition according to claim 1, wherein the derivatizing compound comprises a polyamine having about 2 to 60 total carbon atoms and 3 to 12 nitrogen atoms per molecule.

7. The composition according to claim 1, wherein the amine comprises poly(ethyleneamine) having an average of about 5 to 7 nitrogen atoms per molecule.

8. A lubricating oil composition comprising base oil and a dispersant comprising the reaction product of:

(A) a functionalized polymer of the formula:

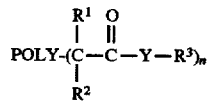

wherein POLY- is derived from unsaturated polymer other than gem-structured polyolefin, the unsaturated polymer having a number average molecular weight prior to functionalization of about 500 to about 20,000, n is a number greater than 0 and represents the functionality of the functionalized polymer, $R^1$ and $R^2$ are the same or different and are selected from the group consisting of hydrogen, hydrocarbyl, and polymeric hydrocarbyl, with the proviso that $R^1$ and $R^2$ are selected such that at least 50 mole percent of the

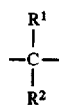

groups have both $R^1$ and $R^2$ not hydrogen, Y is selected from the group consisting of O and S, and $R^3$ is selected from H and hydrocarbyl; and
(B) a derivatizing compound.

9. A lubricating oil composition comprising base oil and a dispersant comprising the reaction product of:

(A) a functionalized polymer of the formula:

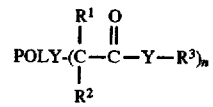

wherein POLY- is derived from unsaturated polymer other than gem-structured polyolefin, the unsaturated polymer having a number average molecular weight prior to functionalization of about 500 to about 20,000, n is a number greater than 0 and represents the functionality of the functionalized polymer, $R^1$ and $R^2$ are the same or different and are selected from the group consisting of hydrogen, hydrocarbyl, and polymeric hydrocarbyl, with the proviso that $R^1$ and $R^2$ are selected such that at least 50 mole percent of the

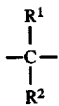

groups have both $R^1$ and $R^2$ not hydrogen, Y is selected from the group consisting of O and S, and $R^3$ is selected from substituted hydrocarbyl, aryl, substituted aryl and mixtures thereof; and (B) a derivatizing compound.

10. The lubricating oil composition according to claim 8 or claim 9, wherein the derivatizing compound is a nucleophilic reagent selected from the group consisting of amine, alcohol, amino-alcohol, reactant metal compound and mixtures thereof.

11. The lubricating oil composition according to claim 10, wherein the derivatizing compound is selected from the group consisting of polyamine, polyol and mixtures thereof.

12. The lubricating oil composition of claim 10, wherein the derivatizing compound is a basic metal salt selected from the group consisting of Ca, Mg, Cu, Zn and Mo.

13. The lubricating oil composition according to claim 8 or claim 9, wherein the dispersant is present in an amount of from about 0.1 to about 10 wt. %.

14. The lubricating oil composition according to claim 8 or claim 9, which is a concentrate comprising from about 10 to about 80 wt. % of the dispersant.

* * * * *